(12) United States Patent
Masiero

(10) Patent No.: US 12,297,273 B2
(45) Date of Patent: May 13, 2025

(54) Fc VARIANT WITH ENHANCED AFFINITY TO Fc RECEPTORS AND IMPROVED THERMAL STABILITY

(71) Applicant: SANOFI, Paris (FR)

(72) Inventor: Alessandro Masiero, Paris (FR)

(73) Assignee: SANOFI, Paris (FR)

( * ) Notice: Subject to any disclaimer, the term of this patent is extended or adjusted under 35 U.S.C. 154(b) by 56 days.

(21) Appl. No.: 17/826,295

(22) Filed: May 27, 2022

(65) Prior Publication Data
US 2023/0077531 A1   Mar. 16, 2023

Related U.S. Application Data

(60) Provisional application No. 63/193,665, filed on May 27, 2021.

(30) Foreign Application Priority Data

Jul. 15, 2021 (EP) .................................. 21315127

(51) Int. Cl.
| | | |
|---|---|---|
| C07K 16/28 | (2006.01) | |
| A61P 35/00 | (2006.01) | |
| A61P 37/04 | (2006.01) | |
| A61K 38/00 | (2006.01) | |

(52) U.S. Cl.
CPC ............ *C07K 16/283* (2013.01); *A61P 35/00* (2018.01); *A61P 37/04* (2018.01); *A61K 38/00* (2013.01); *C07K 2317/31* (2013.01); *C07K 2317/41* (2013.01); *C07K 2317/52* (2013.01); *C07K 2317/569* (2013.01); *C07K 2317/72* (2013.01); *C07K 2317/92* (2013.01); *C07K 2317/94* (2013.01)

(58) Field of Classification Search
CPC .............. C07K 16/283; C07K 2317/31; C07K 2317/41; C07K 2317/52; C07K 2317/569; C07K 2317/72; C07K 2317/92; C07K 2317/94; C07K 2317/53; C07K 2317/71; C07K 2317/73; A61P 35/00; A61P 37/04; A61K 38/00; A61K 2039/505
See application file for complete search history.

(56) References Cited

U.S. PATENT DOCUMENTS

| | | | |
|---|---|---|---|
| 5,837,821 A | 11/1998 | Wu | |
| 5,989,830 A | 11/1999 | Davis et al. | |
| 6,193,980 B1 | 2/2001 | Efstathiou et al. | |
| 7,312,181 B2 | 12/2007 | Lee et al. | |
| 2010/0226923 A1 | 9/2010 | Rao et al. | |
| 2012/0251541 A1 | 10/2012 | Baurin et al. | |
| 2017/0218079 A1 | 8/2017 | Raum et al. | |
| 2018/0208668 A1 | 7/2018 | Lazar et al. | |
| 2018/0258178 A1 | 9/2018 | Tsui et al. | |

FOREIGN PATENT DOCUMENTS

| | | | | |
|---|---|---|---|---|
| CN | 108218998 | * | 6/2018 | ............ C07K 19/00 |
| EP | 2940135 A1 | | 11/2015 | |
| WO | WO 1994/009817 A1 | | 5/1994 | |
| WO | WO 2002/002781 A1 | | 1/2002 | |
| WO | WO 2009/080253 A1 | | 7/2009 | |
| WO | WO 2011/044368 | * | 4/2011 | ............ C12P 21/08 |
| WO | WO 2012/135345 A1 | | 10/2012 | |
| WO | WO 2013/138643 | * | 9/2013 | ............ C07K 16/00 |
| WO | WO 2014/153063 A1 | | 9/2014 | |
| WO | WO 2016/116626 A1 | | 7/2016 | |
| WO | WO 2017/180912 A2 | | 10/2019 | |
| WO | WO 2017/180913 A2 | | 10/2019 | |
| WO | WO 2019/185878 A1 | | 10/2019 | |
| WO | WO-2021046133 A1 | * | 3/2021 | ............ A61K 38/20 |

OTHER PUBLICATIONS

Boyd et al., "The effect of the removal of sialic acid, galactose and total carbohydrate on the functional activity of Campath-1H", Molecular Immunology, Dec. 1995, 32(17-18): 1311-1318.
Davis et al., "Synthesis of Glycoproteins", Chem. Rev., 2002, 102: 579-601.
Estes et al., "Next generation Fc scaffold for multispecific antibodies", iScience, Dec. 17, 2021, 24: 103447.
Gauthier, et al., "Multifunctional Natural Killer Cell Engagers Targeting NKp46 Trigger Protective Tumor Immunity", Cell, Jun. 13, 2019, vol. 177, No. 7, pp. 1701-1713.
Gong et al., "Engineered Human Antibody Constant Domains with Increased Stability", Journal of Biological Chemistry, May 22, 2009, 284(21): 14203-14210.
Harmsen et al., "Properties, production, and applications of camelid single-domain antibody fragments", Applied Microbiol Biotechnol., Nov. 2007, 77(1): 13-22, ePublished Aug. 18, 2007.
International Search Report and Written Opinion for PCT International Patent Application No. PCT/IB2022/055019, dated Oct. 20, 2022.
Jacobsen et al., "Engineering an IgG Scaffold Lacking Effector Function with Optimized Developability", Journal of Biological Chemistry, Feb. 3, 2017, 292(5): 1865-1875, ePublished Dec. 19, 2016.
Labrijn et al., "Bispecific antibodies: a mechanistic review of the pipeline", Nature Reviews Drug Discovery, Jun. 7, 2019, 18(8): 585-608.
Lazar et al., "Engineered antibody Fc variants with enhanced effector function", PNAS USA, 2006, 103: 4005-4010.

(Continued)

*Primary Examiner* — Nelson B Moseley, II
(74) *Attorney, Agent, or Firm* — LATHROP GPM LLP; James H. Velema, Esq.; Michael J. Spellberg

(57) ABSTRACT

The present disclosure provides Fc domain variants, including effector-competent Fc domain variants. The present disclosure also provides nucleic acids encoding Fc domain variants and host cells for making Fc domain variants. Methods for increasing the yield of Fc domain variants, and methods of using Fc domain variants to treat disease, are also provided.

43 Claims, 40 Drawing Sheets

Specification includes a Sequence Listing.

(56) References Cited

OTHER PUBLICATIONS

Leabman et al., "Effects of altered FcyR binding on antibody pharmacokinetics in cynomolgus monkeys", MABS, Nov.-Dec. 2013, 5(6): 896-903.
Lefranc, IMGT unique numbering for immunoglobulin and T cell receptor variable domains and Ig superfamily V-like domains, Dev Comp Immunol. 2003; 27(1): 55-77.
Liu et al., "Fc-Engineering for Modulated Effector Functions—Improving Antibodies for Cancer Treatment", Antibodies, Nov. 17, 2020, 9(4): 64.
Mackness et al., "Antibody Fc engineering for enhanced neonatal Fc receptor binding and prolonged circulation half-life", MABS, Oct. 2019, 11(7): 1276-1288.
Pegoraro et al., "The human myeloma cell line LP-1: a versatile model in which to study early plasma-cell differentiation and c-myc activation", Blood, Mar. 1989, 73(4): 1020-1027.
Peters et al., "Engineering an Improved IgG4 Molecule with Reduced Disulfide Bond Heterogeneity and Increased Fab Domain Thermal Stability", Journal of Biological Chemistry, Jul. 13, 2012, 287(29): 24525-24533.
Roux, et al., "Comparisons of the Ability of Human IgG3 Hinge Mutants, IgM, IgE, and IgA2, to Form Small Immune Complexes: A Role for Flexibility and Geometry", Journal of Immunology, Oct. 15, 1998, vol. 161, No. 8, pp. 4083-4090.
Saunders, "Conceptual Approaches to Modulating Antibody Effector Functions and Circulation Half-Life", Front. Immunol., Jun. 7, 2019, 10: 1296.
Schaefer, et al., "Immunoglobulin Domain Crossover as a Generic Approach for the Production of Bispecific IgG Antibodies", Proceedings of the National academy of Sciences, Jul. 5, 2011, vol. 108, No. 27, pp. 11187-11192.
Sears et al., "Toward Automated Synthesis of Oligosaccharides and Glycoproteins", Science, Mar. 23, 2001, 291(5512): 2344-2350.
Smith, "Mouse model recapitulating human Fcy receptor structural and functional diversity", PNAS, Apr. 2, 2012, 109(16): 6181-6186.
Valente et al., "Pharmacokinetics of novel Fc-engineered monoclonal and multispecific antibodies in cynomolgus monkeys and humanized FcRn transgenic mouse models", Mabs, Jan.-Dec. 2020, 12(1): 1829337.
Wacker et al. "N-linked glycosylation in Campylobacter jejuni and its functional transfer into *E. coli*", Science, 2002, 298: 1790-1793.
Wozniak-Knopp, "Stabilisation of the Fc Fragment of Human IgG1 by Engineered Intradomain Disulfide Bonds", PLOS ONE, Jan. 17, 2012, 7: e30083.
Yang et al., "Engineering of Fc Fragments with Optimized Physicochemical Properties Implying Improvement of Clinical Potentials for Fc-Based Therapeutics", Frontiers in Immunology, Jan. 8, 2018, 8:1860.
Zhang et al. "A New Strategy for the Synthesis of Glycoproteins", Science, 2004, 303: 371-373.

* cited by examiner

FIG. 20

Fc VARIANT WITH ENHANCED AFFINITY TO Fc RECEPTORS AND IMPROVED THERMAL STABILITY

RELATED APPLICATIONS

This application claims priority to U.S. Provisional Patent Application Ser. No. 63/193,665, filed May 27, 2021, and EP Application No. 21315127.7, filed Jul. 15, 2021, the disclosures of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Oct. 25, 2022, is named 728050_SA9-308_ST25.txt and is 56,139 bytes in size.

BACKGROUND

The specific engagement between the fragment crystallizable (Fc) region of an antibody and an Fc gamma receptor (FcγR) is the initial step in effector functions such as antibody-dependent cell-mediated cytotoxicity (ADCC) (Arnold et al., 2007). In humans, activating FcγRIIIa is expressed on the surface of natural killer cells. FcγRIIIa is a low-affinity receptor, and activation of cells results from crosslinking of these surface receptors upon engagement of clustered Fc regions in antibody-antigen immune complexes. The Fc region also interacts with the neonatal Fc receptor (FcRn). This interaction has been shown to extend the half-life of IgG by reducing lysosomal degradation in endothelial cells.

Fc engineering has been extensively pursued to identify Fc domain variants that enhance affinity to the Fc receptors, and to therefore enhance ADCC activity and/or serum half-life. Novel Fc domain variants are needed.

SUMMARY

The present disclosure is directed in part to the discovery that Fc domain variants having altered effector function have decreased thermal stability compared to wild-type Fc domains. Accordingly, the present disclosure is further directed in part to the discovery of novel Fc domain variants having increased thermal stability and unexpectedly increased in vivo stability.

In one aspect, an isolated effector-competent polypeptide, comprising a glycosylated Fc domain comprising a first heavy chain and a second heavy chain, wherein at least one heavy chain comprises an engineered intrachain disulfide bond mediated by a pair of cysteines (C) that substitute for (i) a leucine (L) at amino acid position 242 and a lysine (K) at amino acid position 334; (ii) an alanine (A) at amino acid position 287 and a leucine (L) at amino acid position 306; or (iii) an arginine (R) at amino acid position 292 and a valine (V) at amino acid position 302; wherein the amino acid positions are according to EU numbering; wherein the glycosylated Fc domain is capable of interacting with an antibody effector molecule; and wherein the effector-competent polypeptide has enhanced thermal stability compared to an effector-competent polypeptide having a glycosylated Fc domain capable of interacting with an antibody effector molecule that does not comprise the engineered intrachain disulfide bond, is provided.

In certain exemplary embodiments, the glycosylated Fc domain comprises a native glycan at amino acid position 297, according to EU numbering.

In certain exemplary embodiments, the glycosylated Fc domain comprises an engineered or non-native glycan at amino acid position 297. In certain exemplary embodiments, the engineered or non-native glycan is a modified glycan.

In certain exemplary embodiments, the isolated effector-competent polypeptide is N-glycosylated.

In certain exemplary embodiments, the glycosylated Fc domain comprises a modified glycan conjugated to a therapeutic molecule.

In certain exemplary embodiments, the first heavy chain comprises the pair of cysteines. In certain exemplary embodiments, the first and the second heavy chain each comprise the pair of cysteines.

In certain exemplary embodiments, the Fc domain is an IgG1 Fc domain. In certain exemplary embodiments, wherein the IgG1 Fc domain is a human IgG1 Fc domain.

In certain exemplary embodiments, the antibody effector molecule is a FcRn. In certain exemplary embodiments, the isolated effector-competent polypeptide has enhanced binding affinity to the FcRn compared to a wild-type Fc domain.

In certain exemplary embodiments, the antibody effector molecule is a FcγRIIIa. In certain exemplary embodiments, the isolated effector-competent polypeptide has enhanced binding affinity to the FcγRIIIa compared to a polypeptide comprising a wild-type Fc domain.

In certain exemplary embodiments, the isolated effector-competent polypeptide has altered serum half-life compared to a wild-type Fc domain. In certain exemplary embodiments, the isolated effector-competent polypeptide has enhanced serum half-life compared to a wild-type Fc domain. In certain exemplary embodiments, the isolated effector-competent polypeptide has improved in vivo stability compared to a wild-type Fc domain.

In certain exemplary embodiments, the Fc domain further comprises a substitution at amino acid position 332, according to EU numbering. In certain exemplary embodiments, the substitution at amino acid position 332 is a glutamic acid (E). In certain exemplary embodiments, the Fc domain further comprises one or more substitutions at amino acid positions 236, 239, or 330, according to EU numbering. In certain exemplary embodiments, the substitution at amino acid position 236 is an alanine (A). In certain exemplary embodiments, the substitution at amino acid position 239 is an aspartic acid (D). In certain exemplary embodiments, the substitution at amino acid position 330 is a leucine (L).

In certain exemplary embodiments, the Fc domain further comprises an aspartic acid (D) at amino acid position 239, and a glutamic acid (E) at amino acid position 332, according to EU numbering.

In certain exemplary embodiments, the Fc domain further comprises an alanine (A) at amino acid position 236, an aspartic acid (D) at amino acid position 239, and a glutamic acid (E) at amino acid position 332, according to EU numbering.

In certain exemplary embodiments, the Fc domain further comprises an alanine (A) at amino acid position 236, an aspartic acid (D) at amino acid position 239, a leucine (L) at amino acid position 330, and a glutamic acid (E) at amino acid position 332, according to EU numbering.

In certain exemplary embodiments, wherein the Fc domain further comprises a substitution at amino acid position 256 and/or 307, according to EU numbering.

In certain exemplary embodiments, the substitution at amino acid position 256 is an aspartic acid (D). In certain exemplary embodiments, the substitution at amino acid position 307 is a glutamine (Q).

In certain exemplary embodiments, the Fc domain further comprises an aspartic acid (D) at amino acid position 256 and a glutamine (Q) at amino acid position 307, according to EU numbering.

In certain exemplary embodiments, the Fc domain further comprises an aspartic acid (D) at amino acid position 239, a glutamic acid (E) at amino acid position 332, an aspartic acid (D) at amino acid position 256, and a glutamine (Q) at amino acid position 307, according to EU numbering.

In certain exemplary embodiments, the Fc domain further comprises an alanine (A) at amino acid position 236, an aspartic acid (D) at amino acid position 239, and a glutamic acid (E) at amino acid position 332, an aspartic acid (D) at amino acid position 256, and a glutamine (Q) at amino acid position 307, according to EU numbering.

In certain exemplary embodiments, the Fc domain further comprises an alanine (A) at amino acid position 236, an aspartic acid (D) at amino acid position 239, a leucine (L) at amino acid position 330, a glutamic acid (E) at amino acid position 332, an aspartic acid (D) at amino acid position 256, and a glutamine (Q) at amino acid position 307, according to EU numbering.

In another aspect, an isolated effector-competent polypeptide, comprising: a glycosylated Fc domain comprising a first heavy chain and a second heavy chain, wherein at least one heavy chain comprises an engineered intrachain disulfide bond mediated by a pair of cysteines (C) that substitute for: (i) a leucine (L) at amino acid position 242 and a lysine (K) at amino acid position 334; (ii) an alanine (A) at amino acid position 287 and a leucine (L) at amino acid position 306; or (iii) an arginine (R) at amino acid position 292 and a valine (V) at amino acid position 302; wherein the glycosylated Fc domain is capable of interacting with an antibody effector molecule and comprises a glutamic acid (E) at amino acid position 332; wherein the effector-competent polypeptide has enhanced thermal stability compared to an effector-competent polypeptide having a glycosylated Fc domain capable of interacting with an antibody effector molecule and comprising a glutamic acid (E) at amino acid position 332, that does not comprise the engineered intrachain disulfide bond; and wherein the amino acid positions are according to EU numbering, is provided.

In certain exemplary embodiments, the glycosylated Fc domain comprises a native glycan at amino acid position 297, according to EU numbering.

In certain exemplary embodiments, the glycosylated Fc domain comprises a native glycan at amino acid position 297, according to EU numbering. In certain exemplary embodiments, the engineered or non-native glycan is a modified glycan.

In certain exemplary embodiments, the isolated effector-competent polypeptide is N-glycosylated. In certain exemplary embodiments, the modified glycan is conjugated to a therapeutic molecule.

In certain exemplary embodiments, the first heavy chain comprises the pair of cysteines. In certain exemplary embodiments, the first and the second heavy chain each comprise the pair of cysteines.

In certain exemplary embodiments, the modified Fc domain is a modified human Fc domain. In certain exemplary embodiments, the modified Fc domain is a modified human IgG1 Fc domain.

In certain exemplary embodiments, the antibody effector molecule is a FcRn. In certain exemplary embodiments, the isolated effector-competent polypeptide has enhanced binding affinity to the FcRn compared to a wild-type Fc domain.

In certain exemplary embodiments, the antibody effector molecule is a FcγRIIIa. In certain exemplary embodiments, the isolated effector-competent polypeptide has enhanced binding affinity to the FcγRIIIa compared to a polypeptide comprising a wild-type Fc domain.

In certain exemplary embodiments, the isolated effector-competent polypeptide has altered serum half-life compared to a wild-type Fc domain. In certain exemplary embodiments, the isolated effector-competent polypeptide has enhanced serum half-life compared to a wild-type Fc domain. In certain exemplary embodiments, the isolated effector-competent polypeptide has improved in vivo stability compared to a wild-type Fc domain.

In certain exemplary embodiments, the isolated effector-competent polypeptide further comprises: an aspartic acid (D) at amino acid position 239; an alanine (A) at amino acid position 236; a leucine (L) at amino acid position 330; an aspartic acid (D) at amino acid position 256; and/or a glutamine (Q) at amino acid position 30.

In certain exemplary embodiments, the Fc domain further comprises an aspartic acid (D) at amino acid position 239, and a glutamic acid (E) at amino acid position 332, according to EU numbering.

In certain exemplary embodiments, the Fc domain further comprises an alanine (A) at amino acid position 236, an aspartic acid (D) at amino acid position 239, and a glutamic acid (E) at amino acid position 332, according to EU numbering.

In certain exemplary embodiments, the Fc domain further comprises an alanine (A) at amino acid position 236, an aspartic acid (D) at amino acid position 239, a leucine (L) at amino acid position 330, and a glutamic acid (E) at amino acid position 332, according to EU numbering.

In certain exemplary embodiments, the Fc domain further comprises an aspartic acid (D) at amino acid position 256 and a glutamine (Q) at amino acid position 307, according to EU numbering.

In certain exemplary embodiments, the one or more substitutions are on the same heavy chain as the engineered disulfide bond.

In certain exemplary embodiments, the one or more substitutions are on a different heavy chain as the engineered disulfide bond.

In certain exemplary embodiments, the isolated effector-competent polypeptide further comprises a binding domain. In certain exemplary embodiments, the binding domain comprises one or more antigen binding domains. In certain exemplary embodiments, the one or more antigen binding domains specifically bind to a tumor antigen. In certain exemplary embodiments, the one or more antigen binding domains specifically bind to an antigen on an immune cell. In certain exemplary embodiments, the binding polypeptide comprises a therapeutic polypeptide. In certain exemplary embodiments, the therapeutic polypeptide may be a receptor, a ligand, or an enzyme.

In certain exemplary embodiments, the polypeptide is an antibody. In certain exemplary embodiments, the polypeptide is monoclonal antibody. In certain exemplary embodiments, the antibody is a chimeric, humanized, or human antibody. In certain exemplary embodiments, the antibody is a full-length antibody.

In certain exemplary embodiments, the polypeptide is a single-domain antibody. In certain exemplary embodiments, the single-domain antibody is a VHH antibody.

In certain exemplary embodiments, the antibody is a multi-specific antibody. In certain exemplary embodiments, the multi-specific antibody is of a format selected from the group consisting of: DVD-Ig, a CODV based format such as CODV-Ig, CrossMab, CrossMab-Fab, and Tandem Fabs. Multi-specific antibodies based on the CROSSODILES® CODV platform are notably described in WO2012135345, WO2016116626, WO2017180913. CROSSODILES® is a registered trademark of Sanofi. In certain exemplary embodiments, the multi-specific antibody is a T cell engager. In certain exemplary embodiments, the multi-specific antibody is an NK cell engager.

In certain exemplary embodiments, the binding polypeptide is linked to the N-terminus and/or the C-terminus of the Fc domain.

In certain exemplary embodiments, the isolated effector-competent polypeptide is capable of depleting a target cell by antibody-dependent cellular cytotoxicity (ADCC) and/or complement-dependent cytotoxicity (CDC).

In certain exemplary embodiments, the target cell is a cancer cell.

In certain exemplary embodiments, the target cell is an immune cell.

In certain exemplary embodiments, the polypeptide is an Fc-fusion polypeptide.

In another aspect, an isolated nucleic acid molecule comprising a nucleic acid encoding an isolated effector-competent polypeptide described above, is provided.

In certain exemplary embodiments, a vector comprises the isolated nucleic acid molecule.

In certain exemplary embodiments, the vector is an expression vector.

In another aspect, a host cell comprising the vector is provided.

In certain exemplary embodiments, the host cell is of eukaryotic or prokaryotic origin. In certain exemplary embodiments, the host cell is of mammalian origin. In certain exemplary embodiments, the host cell is of bacterial origin.

In another aspect, a pharmaceutical composition comprising an isolated effector-competent polypeptide described above is provided.

In another aspect, a method of increasing yield of an isolated effector-competent polypeptide, comprising: expressing a glycosylated Fc domain comprising a first heavy chain and a second heavy chain, wherein at least one heavy chain comprises an engineered intrachain disulfide bond mediated by a pair of cysteines (C) that substitute for: (i) a leucine (L) at amino acid position 242 and a lysine (K) at amino acid position 334; (ii) an alanine (A) at amino acid position 287 and a leucine (L) at amino acid position 306; or (iii) an arginine (R) at amino acid position 292 and a valine (V) at amino acid position 302; wherein the amino acid positions are according to EU numbering; wherein the glycosylated Fc domain is capable of interacting with an antibody effector molecule; and wherein the effector-competent polypeptide has enhanced thermal stability compared to an effector-competent polypeptide having a glycosylated Fc domain capable of interacting with an antibody effector molecule that does not comprise the engineered intrachain disulfide bond; and purifying the effector-competent polypeptide, wherein yield of said polypeptide is increased compared to a polypeptide comprising a wild-type glycosylated Fc domain, is provided.

In certain exemplary embodiments, the glycosylated Fc domain comprises a native glycan at amino acid position 297, according to EU numbering. In certain exemplary embodiments, the glycosylated Fc domain comprises an engineered or non-native glycan at amino acid position 297, that is optionally a modified glycan. In certain exemplary embodiments, the isolated effector-competent polypeptide is N-glycosylated. In certain exemplary embodiments, the modified glycan can be conjugated to a therapeutic molecule.

In certain exemplary embodiments, the first heavy chain comprises the pair of cysteines.

In certain exemplary embodiments, the first and the second heavy chain each comprise the pair of cysteines.

In certain exemplary embodiments, the Fc domain is a human Fc domain. In certain exemplary embodiments, the Fc domain is a IgG1 Fc domain.

In certain exemplary embodiments, the antibody effector molecule is a FcRn. In certain exemplary embodiments, the isolated effector-competent polypeptide has enhanced binding affinity to the FcRn compared to a wild-type Fc domain.

In certain exemplary embodiments, the antibody effector molecule is a FcγRIIIa. In certain exemplary embodiments, the isolated effector-competent polypeptide has enhanced binding affinity to the FcγRIIIa compared to a polypeptide comprising a wild-type Fc domain.

In certain exemplary embodiments, the isolated effector-competent polypeptide has altered serum half-life compared to a wild-type Fc domain. In certain exemplary embodiments, the isolated effector-competent polypeptide has enhanced serum half-life compared to a wild-type Fc domain.

In certain exemplary embodiments, the isolated polypeptide further comprises one or more effector function-enhancing amino acid substitutions, optionally a substitution at amino acid position 332, according to EU numbering. In certain exemplary embodiments, the substitution at amino acid position 332 is a glutamic acid (E). In certain exemplary embodiments, the Fc domain further comprises one or more substitutions at amino acid positions 236, 239, or 330, according to EU numbering. In certain exemplary embodiments, the substitution at amino acid position 236 is an alanine (A). In certain exemplary embodiments, the substitution at amino acid position 239 is an aspartic acid (D). In certain exemplary embodiments, the substitution at amino acid position 330 is a leucine (L).

In certain exemplary embodiments, the Fc domain further comprises an aspartic acid (D) at amino acid position 239, and a glutamic acid (E) at amino acid position 332, according to EU numbering.

In certain exemplary embodiments, the Fc domain further comprises an alanine (A) at amino acid position 236, an aspartic acid (D) at amino acid position 239, and a glutamic acid (E) at amino acid position 332, according to EU numbering.

In certain exemplary embodiments, the Fc domain further comprises an alanine (A) at amino acid position 236, an aspartic acid (D) at amino acid position 239, a leucine (L) at amino acid position 330, and a glutamic acid (E) at amino acid position 332, according to EU numbering.

In certain exemplary embodiments, the isolated effector-competent polypeptide further comprises a substitution at amino acid position 256 and/or 307, according to EU numbering. In certain exemplary embodiments, the substitution at amino acid position 256 is an aspartic acid (D). In certain exemplary embodiments, the substitution at amino acid position 307 is a glutamine (Q).

In certain exemplary embodiments, the Fc domain further comprises an aspartic acid (D) at amino acid position 256 and a glutamine (Q) at amino acid position 307, according to EU numbering.

In certain exemplary embodiments, the Fc domain further comprises an aspartic acid (D) at amino acid position 239, a glutamic acid (E) at amino acid position 332, an aspartic acid (D) at amino acid position 256, and a glutamine (Q) at amino acid position 307, according to EU numbering.

In certain exemplary embodiments, the Fc domain further comprises an alanine (A) at amino acid position 236, an aspartic acid (D) at amino acid position 239, and a glutamic acid (E) at amino acid position 332, an aspartic acid (D) at amino acid position 256, and a glutamine (Q) at amino acid position 307, according to EU numbering.

In certain exemplary embodiments, the Fc domain further comprises an alanine (A) at amino acid position 236, an aspartic acid (D) at amino acid position 239, a leucine (L) at amino acid position 330, a glutamic acid (E) at amino acid position 332, an aspartic acid (D) at amino acid position 256, and a glutamine (Q) at amino acid position 307, according to EU numbering. In certain exemplary embodiments, the one or more substitutions are on the same heavy chain as the engineered disulfide bond. In certain exemplary embodiments, the one or more substitutions are on a different heavy chain as the engineered disulfide bond.

In certain exemplary embodiments, the isolated effector-competent polypeptide further comprises a binding polypeptide. In certain exemplary embodiments, the binding polypeptide comprises one or more antigen binding domains. In certain exemplary embodiments, the one or more antigen binding domains specifically bind a tumor antigen. In certain exemplary embodiments, the one or more antigen binding domains specifically bind to an antigen on an immune cell.

In certain exemplary embodiments, the isolated effector-competent polypeptide is an antibody. In certain exemplary embodiments, the isolated effector-competent polypeptide is monoclonal antibody. In certain exemplary embodiments, the antibody is a chimeric, humanized, or human antibody. In certain exemplary embodiments, the antibody is a full-length antibody.

In certain exemplary embodiments, the isolated effector-competent polypeptide is a single-domain antibody. In certain exemplary embodiments, the single-domain antibody is a VHH antibody. In certain exemplary embodiments, the antibody is a multi-specific antibody. In certain exemplary embodiments, the multi-specific antibody is of a format selected from the group consisting of: DVD-Ig, a CODV based format such as CODV-Ig, CrossMab, CrossMab-Fb, and Tandem Fabs. In certain exemplary embodiments, the multi-specific antibody is a T cell engager. In certain exemplary embodiments, the multi-specific antibody is an NK cell engager.

In certain exemplary embodiments, the binding polypeptide comprises a therapeutic polypeptide. In certain exemplary embodiments, the therapeutic polypeptide may be a receptor, a ligand, or an enzyme.

In certain exemplary embodiments, the binding polypeptide is linked to the N-terminus and/or the C-terminus of the Fc domain.

In certain exemplary embodiments, the isolated effector-competent polypeptide is capable of depleting a target cell by antibody-dependent cellular cytotoxicity (ADCC) and/or complement-dependent cytotoxicity (CDC). In certain exemplary embodiments, the target cell is a cancer cell. In certain exemplary embodiments, the target cell is an immune cell.

In certain exemplary embodiments, the isolated effector-competent polypeptide is an Fc-fusion polypeptide.

In another aspect, a method of treating a disease or disorder in a subject in need thereof, comprising administering to the subject an effective amount of an effector-competent polypeptide described above, is provided.

In certain exemplary embodiments, the disease or disorder is a cancer. In certain exemplary embodiments, the disease or disorder is an inflammatory disease. In certain exemplary embodiments, the disease or disorder is an autoimmune disease.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 1A depicts the mean frequency of hydrophobic contacts for the glutamic acid (E) residue at amino acid position 332. FIG. 1B depicts the root mean square fluctuation (in angstroms) of the alpha carbon at 300 K.

FIG. 20 depicts the mean PK profiles of mAb3 antibodies in Tg32 mice (log scale).

DETAILED DESCRIPTION

Figure 1A:
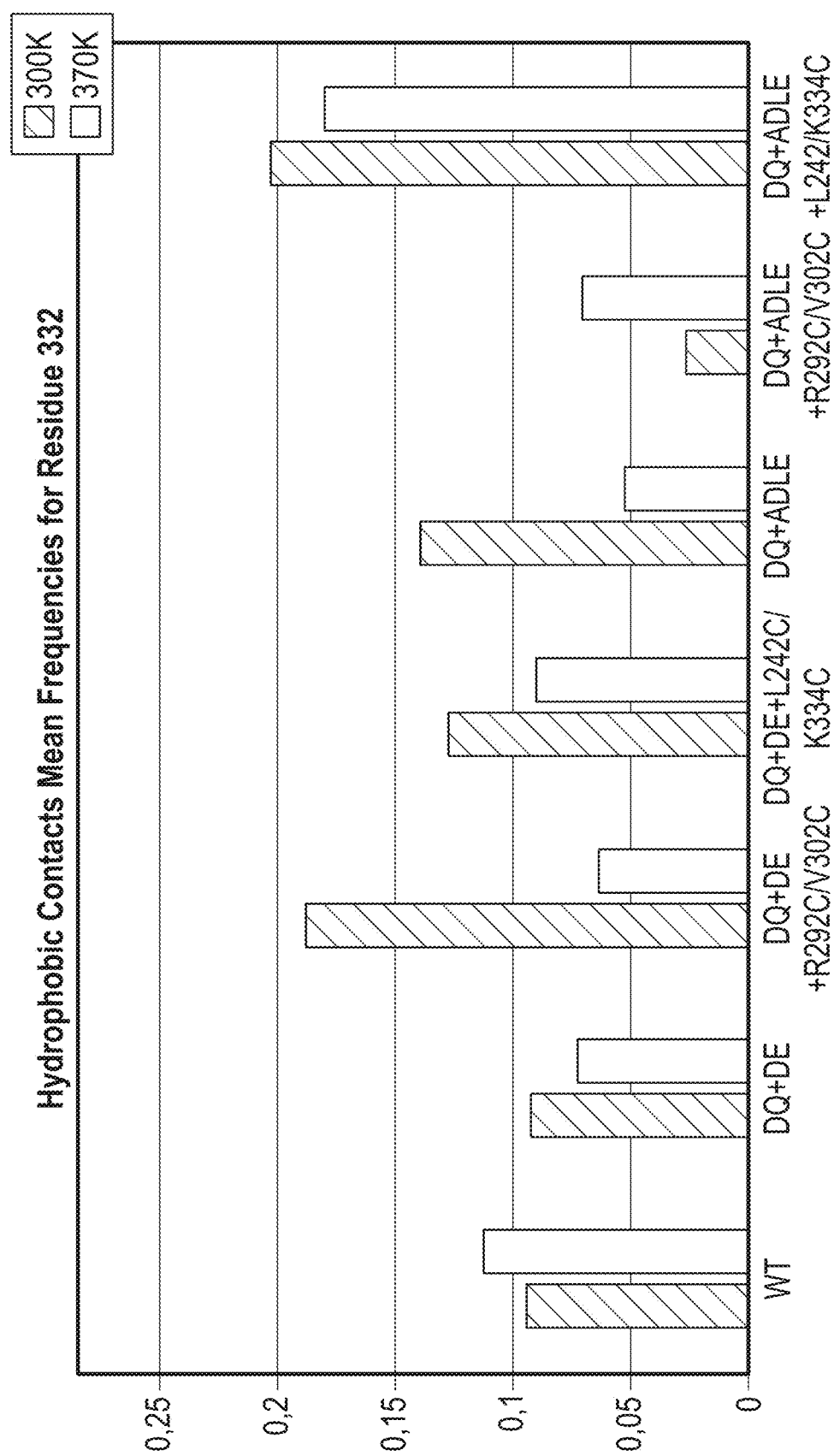
FIG. 1A-FIG. 1B depict the mean of hydrophobic contacts frequency at 300 K and 370 K.

The present disclosure provides novel Fc domain variants (e.g., novel binding polypeptides comprising Fc domain variants) having improved thermal stability. The present disclosure also provides novel Fc domain variants (e.g., novel binding polypeptides comprising Fc domain variants) having improved binding to Fc receptors. The present disclosure further provides novel Fc domain variants (e.g., binding polypeptides comprising Fc domain variants) comprising a glycosylated Fc domain that enhances interaction with an antibody effector molecule compared to a wild-type (e.g., non-modified) Fc domain. The present disclosure also provides nucleic acids encoding Fc domain variants (e.g., novel binding polypeptides comprising Fc domain variants), recombinant expression vectors and host cells for making Fc domain variants (e.g., novel binding polypeptides comprising Fc domain variants), and pharmaceutical compositions comprising the isolated Fc domain variants (e.g., novel binding polypeptides comprising Fc domain variants). Methods of using the Fc domain variants (e.g., novel binding polypeptides comprising Fc domain variants) of the present disclosure to treat one or more diseases or disorders are also provided.

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, $2^{nd}$ edition).

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The term "polypeptide" refers to any polymeric chain of amino acids and encompasses native or artificial proteins, polypeptide analogs or variants of a protein sequence, or fragments thereof, unless otherwise contradicted by context. A polypeptide may be monomeric or polymeric. A polypeptide fragment comprises at least about 5 contiguous amino acids, at least about 10 contiguous amino acids, at least about 15 contiguous amino acids, or at least about 20 contiguous amino acids, for example.

The term "isolated protein" or "isolated polypeptide" refers to a protein or polypeptide that by virtue of its origin or source of derivation is not associated with naturally associated components that accompany it in its native state;

is substantially free of other proteins from the same species; is expressed by a cell from a different species; or does not occur in nature. Thus, a protein or polypeptide that is chemically synthesized or synthesized in a cellular system different from the cell from which it naturally originates will be "isolated" from its naturally associated components. A protein or polypeptide may also be rendered substantially free of naturally associated components by isolation using protein purification techniques well known in the art.

As used herein, the term "binding protein" or "binding polypeptide" shall refer to a protein or polypeptide (e.g., an antibody or immunoadhesin) that contains at least one binding site which is responsible for selectively binding to a target antigen of interest (e.g., a human target antigen). Exemplary binding sites include an antibody variable domain, a ligand binding site of a receptor, or a receptor binding site of a ligand. In certain aspects, the binding proteins or binding polypeptides comprise multiple (e.g., two, three, four, or more) binding sites. In certain aspects, the binding protein or binding polypeptide is a therapeutic enzyme.

The term "ligand" refers to any substance capable of binding, or of being bound, to another substance. Similarly, the term "antigen" refers to any substance to which an antibody may be generated. Although "antigen" is commonly used in reference to an antibody binding substrate, and "ligand" is often used when referring to receptor binding substrates, these terms are not distinguishing, one from the other, and encompass a wide range of overlapping chemical entities. For the avoidance of doubt, antigen and ligand are used interchangeably throughout herein. Antigens/ligands may be a peptide, a polypeptide, a protein, an aptamer, a polysaccharide, a sugar molecule, a carbohydrate, a lipid, an oligonucleotide, a polynucleotide, a synthetic molecule, an inorganic molecule, an organic molecule, and any combination thereof.

The dissociation constant ($K_D$) of a binding protein can be determined, for example, by surface plasmon resonance. Generally, surface plasmon resonance analysis measures real-time binding interactions between ligand (a target antigen on a biosensor matrix) and analyte (a binding protein in solution) by surface plasmon resonance (SPR) using the BIAcore system (Pharmacia Biosensor; Piscataway, NJ). Surface plasmon analysis can also be performed by immobilizing the analyte (binding protein on a biosensor matrix) and presenting the ligand (target antigen). The term "$K_D$" as used herein refers to the dissociation constant of the interaction between a particular binding protein and a target antigen.

The term "specifically binds" as used herein, refers to the ability of an antibody or an immunoadhesin to bind to a target (e.g., an antigen) with a dissociation constant ($K_D$) of at most about $1 \times 10^{-6}$ M, about $1 \times 10^{-7}$ M, about $1 \times 10^{-8}$ M, about $1 \times 10^{-9}$ M, about $1 \times 10^{-10}$ M, about $1 \times 10^{-11}$ M, about $1 \times 10^{-12}$ M or less, and/or to bind to an antigen with an affinity that is at least about two-fold greater than its affinity for a nonspecific antigen. Specific binding of an antibody can be to a target antigen through the CDR sequences. An antibody can also specifically bind to FcRs, such as FcRn or FcγRIIIa through the Fc region.

As used herein, the term "antibody" refers to such assemblies (e.g., intact antibody molecules, immunoadhesins, or variants thereof) which have significant known specific immunoreactive activity to an antigen of interest (e.g. a tumor associated antigen). Antibodies and immunoglobulins comprise light and heavy chains, with or without an interchain covalent linkage between them. Basic immunoglobulin structures in vertebrate systems are relatively well understood.

As will be discussed in more detail below, the generic term "antibody" comprises five distinct classes of antibody that can be distinguished biochemically. While all five classes of antibodies are clearly within the scope of the current disclosure, the following discussion will generally be directed to the IgG class of immunoglobulin molecules. With regard to IgG, immunoglobulins comprise two identical light chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

Light chains of immunoglobulin are classified as either kappa (κ) or lambda (λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells, or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma (γ), mu (μ), alpha (α), delta (δ), or epsilon (ε), with some subclasses among them (e.g., γ1-γ4). It is the nature of this chain that determines the "class" of the antibody as IgG, IgM, IgA IgG, or IgE, respectively. The immunoglobulin isotype subclasses (e.g., IgG1, IgG2, IgG3, IgG4, IgA1, etc.) are well-characterized and are known to confer functional specialization. Modified versions of each of these classes and isotypes are readily discernable to the skilled artisan in view of the instant disclosure and, accordingly, are within the scope of the current disclosure.

Both the light and heavy chains are divided into regions of structural and functional homology. The term "region" refers to a part or portion of an immunoglobulin or antibody chain and includes constant region or variable regions, as well as more discrete parts or portions of said regions. For example, light chain variable regions include "complementarity determining regions" or "CDRs" interspersed among "framework regions" or "FRs," as defined herein.

The regions of an immunoglobulin heavy or light chain may be defined as "constant" (C) region or "variable" (V) regions, based on a relative lack of sequence variation within the regions of various class members in the case of a "constant region," or based on a significant variation within the regions of various class members in the case of a "variable regions." The terms "constant region" and "variable region" may also be used functionally. In this regard, it will be appreciated that the variable regions of an immunoglobulin or antibody determine antigen recognition and specificity. Conversely, the constant regions of an immunoglobulin or antibody confer important effector functions such as secretion, trans-placental mobility, Fc receptor binding, complement binding, and the like. The subunit structures and three dimensional configurations of the constant regions of the various immunoglobulin classes are well-known.

The constant and variable regions of immunoglobulin heavy and light chains are folded into domains. The term "domain" refers to a globular region of a heavy or light chain comprising peptide loops (e.g., comprising 3 to 4 peptide loops) stabilized, for example, by β-pleated sheet and/or an intra-chain disulfide bond. Constant region domains on the light chain of an immunoglobulin are referred to interchangeably as "light chain constant region domains," "CL regions" or "CL domains." Constant domains on the heavy chain (e.g., hinge, CH1, CH2 or CH3 domains) are referred to interchangeably as "heavy chain constant region domains," "CH" region domains or "CH domains." Variable domains on the light chain are referred to interchangeably as "light chain variable region domains," "VL region domains" or "VL domains." Variable domains on the heavy chain are referred to interchangeably as "heavy chain variable region domains," "VH region domains" or "VH domains."

By convention, the numbering of the amino acids of the variable constant region domains increases as they become more distal from the antigen-binding site or amino-terminus of the immunoglobulin or antibody. The N-terminus of each heavy and light immunoglobulin chain is a variable region and the C-terminus is a constant region. The CH3 and CL domains comprise the carboxy-terminus of the heavy and light chain, respectively. Accordingly, the domains of a light chain immunoglobulin are arranged in a VL-CL orientation, while the domains of the heavy chain are arranged in the VH-CH1-hinge-CH2-CH3 orientation.

The assignment of amino acids to each variable region domain is in accordance with the definitions of Kabat, Sequences of Proteins of Immunological Interest (National Institutes of Health, Bethesda, MD, 1987 and 1991). Kabat also provides a widely used numbering convention (Kabat numbering) in which corresponding residues between different heavy chain variable regions or between different light chain variable regions are assigned the same number. CDRs 1, 2 and 3 of a VL domain are also referred to herein, respectively, as CDR-L1, CDR-L2 and CDR-L3. CDRs 1, 2 and 3 of a VH domain are also referred to herein, respectively, as CDR-H1, CDR-H2 and CDR-H3. If so noted, the assignment of CDRs can be in accordance with IMGT® (Lefranc et al., Developmental & Comparative Immunology 27:55-77; 2003) in lieu of Kabat. Numbering of the heavy chain constant region is via the EU index as set forth in Kabat (Kabat, Sequences of Proteins of Immunological Interest, National Institutes of Health, Bethesda, MD, 1987 and 1991).

As used herein, the term "VH domain" includes the amino terminal variable domain of an immunoglobulin heavy chain, and the term "VL domain" includes the amino terminal variable domain of an immunoglobulin light chain.

As used herein, the term "CH1 domain" includes the first (most amino terminal) constant region domain of an immunoglobulin heavy chain that extends, e.g., from about positions 114-223 in the Kabat numbering system (EU positions 118-215). The CH1 domain is adjacent to the VH domain and amino terminal to the hinge region of an immunoglobulin heavy chain molecule, and does not form a part of the Fc region of an immunoglobulin heavy chain.

As used herein, the term "hinge region" includes the portion of a heavy chain molecule that joins the CH1 domain to the CH2 domain. The hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998, 161:4083).

As used herein, the term "CH2 domain" includes the portion of a heavy chain immunoglobulin molecule that extends, e.g., from about positions 244-360 in the Kabat numbering system (EU positions 231-340). The CH2 domain is unique in that it is not closely paired with another domain. Rather, two N-linked branched carbohydrate chains are interposed between the two CH2 domains of an intact native IgG molecule. In one embodiment, a binding polypeptide of the current disclosure comprises a CH2 domain derived from an IgG1 molecule (e.g. a human IgG1 molecule).

As used herein, the term "CH3 domain" includes the portion of a heavy chain immunoglobulin molecule that extends approximately 110 residues from N-terminus of the CH2 domain, e.g., from about positions 361-476 of the Kabat numbering system (EU positions 341-445). The CH3 domain typically forms the C-terminal portion of the antibody. In some immunoglobulins, however, additional domains may extend from the CH3 domain to form the C-terminal portion of the molecule (e.g., the CH4 domain in the μ chain of IgM and the e chain of IgE). In one embodiment, a binding polypeptide of the current disclosure comprises a CH3 domain derived from an IgG1 molecule (e.g., a human IgG1 molecule).

As used herein, the term "CL domain" includes the constant region domain of an immunoglobulin light chain that extends, e.g., from about Kabat position 107A to about Kabat position 216. The CL domain is adjacent to the VL domain. In one embodiment, a binding polypeptide of the current disclosure comprises a CL domain derived from a kappa light chain (e.g., a human kappa light chain).

The variable regions of an antibody allow it to selectively recognize and specifically bind epitopes on antigens. That is, the VL domain and VH domain of an antibody combine to form the variable region (Fv) that defines a three dimensional antigen binding site. This quaternary antibody structure forms the antigen binding site present at the end of each arm of the "Y" configuration. More specifically, the antigen binding site is defined by three complementary determining regions (CDRs) on each of the heavy and light chain variable regions. As used herein, the term "antigen binding site" includes a site that specifically binds an antigen (e.g., a cell surface or soluble antigen). The antigen binding site includes an immunoglobulin heavy chain and light chain variable region and the binding site formed by these variable regions determines the specificity of the antibody. An antigen binding site is formed by variable regions that vary from one antibody to another. The altered antibodies of the current disclosure comprise at least one antigen binding site.

In certain embodiments, binding polypeptides of the current disclosure comprise at least two antigen binding domains that provide for the association of the binding polypeptide with the selected antigen. The antigen binding domains need not be derived from the same immunoglobulin molecule. In this regard, the variable region may or be derived from any type of animal that can be induced to mount a humoral response and generate immunoglobulins against the desired antigen. As such, the variable region of the binding polypeptide may be, for example, of mammalian origin e.g., may be human, murine, rat, goat, sheep, non-human primate (such as cynomolgus monkeys, macaques, etc.), lupine, or camelid (e.g., from camels, llamas and related species).

In naturally occurring antibodies, the six CDRs present on each monomeric antibody are short, non-contiguous sequences of amino acids that are specifically positioned to form the antigen binding site as the antibody assumes its three-dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to the immunoreactive antigen epitope.

Exemplary binding polypeptides include antibody variants. As used herein, the term "antibody variant" includes synthetic and engineered forms of antibodies which are altered such that they are not naturally occurring, e.g., antibodies that comprise at least two heavy chain portions but not two complete heavy chains (such as, domain deleted antibodies or minibodies); multi-specific forms of antibodies (e.g., bi-specific, tri-specific, etc.) altered to bind to two or more different antigens or to different epitopes on a single antigen); heavy chain molecules joined to scFv molecules and the like. In addition, the term "antibody variant" includes multivalent forms of antibodies (e.g., trivalent, tetravalent, etc., antibodies that bind to three, four or more copies of the same antigen).

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen). The subject binding polypeptides typically has at least one binding site specific for a human antigen molecule. For example, a typical IgG1 monoclonal antibody is specific for one target antigen. A bivalent antibody is one comprising antigen binding domains that targets two different antigens, or two antigen binding domains that target one antigen. Similarly, a trivalent antibody may be a monospecific antibody with three targeting domains to a single antigen. A trivalent antibody may be bispecific if it binds a first antigen with two binding domains and a second antigen with another binding domain. A trivalent antibody maybe trispecific and bind to three different targets.

The term "specificity" refers to the ability to specifically bind (e.g., immunoreact with) a given target antigen (e.g., a human target antigen). A binding polypeptide may be monospecific and contain one or more binding sites which specifically bind a target or a polypeptide may be multi-specific and contain two or more binding sites which specifically bind the same or different targets. In certain embodiments, a binding polypeptide is specific for two different (e.g., non-overlapping) portions of the same target. In certain embodiments, a binding polypeptide is specific for more than one target. Exemplary binding polypeptides (e.g., antibodies) which comprise antigen binding sites that bind to antigens expressed on tumor cells are known in the art and one or more CDRs from such antibodies can be included in an antibody as described herein.

The term "antigen" or "target antigen," as used herein, refers to a molecule or a portion of a molecule that is capable of being bound by the binding site of a binding polypeptide. A target antigen may have one or more epitopes.

The term "about" or "approximately" means within about 20%, such as within about 10%, within about 5%, or within about 1% or less of a given value or range.

As used herein, "administer" or "administration" refers to the act of injecting or otherwise physically delivering a substance as it exists outside the body (e.g., an isolated binding polypeptide provided herein) into a patient, such as by, but not limited to, pulmonary (e.g., inhalation), mucosal (e.g., intranasal), intradermal, intravenous, intramuscular delivery and/or any other method of physical delivery described herein or known in the art. When a disease, or a symptom thereof, is being managed or treated, administration of the substance typically occurs after the onset of the disease or symptoms thereof. When a disease, or symptom thereof, is being prevented, administration of the substance typically occurs before the onset of the disease or symptoms thereof and may be continued chronically to defer or reduce the appearance or magnitude of disease-associated symptoms.

As used herein, the term "composition" is intended to encompass a product containing the specified ingredients (e.g., an isolated binding polypeptide provided herein) in, optionally, the specified amounts, as well as any product which results, directly or indirectly, from combination of the specified ingredients in, optionally, the specified amounts.

"Effective amount" means the amount of active pharmaceutical agent (e.g., an isolated binding polypeptide of the present disclosure) sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

As used herein, the terms "subject" and "patient" are used interchangeably. As used herein, a subject is can be a mammal, such as a non-primate (e.g., cows, pigs, horses, cats, dogs, rats, etc.) or a primate (e.g., monkey and human). In certain embodiments, the term "subject," as used herein, refers to a vertebrate, such as a mammal. Mammals include, without limitation, humans, non-human primates, wild animals, feral animals, farm animals, sport animals, and pets.

As used herein, the term "therapy" refers to any protocol, method and/or agent that can be used in the prevention, management, treatment and/or amelioration of a disease or a symptom related thereto. In some embodiments, the term "therapy" refers to any protocol, method and/or agent that can be used in the modulation of an immune response to an infection in a subject or a symptom related thereto. In some embodiments, the terms "therapies" and "therapy" refer to a biological therapy, supportive therapy, and/or other therapies useful in the prevention, management, treatment and/or amelioration of a disease or a symptom related thereto, known to one of skill in the art such as medical personnel. In other embodiments, the terms "therapies" and "therapy" refer to a biological therapy, supportive therapy, and/or other therapies useful in the modulation of an immune response to an infection in a subject or a symptom related thereto known to one of skill in the art such as medical personnel.

As used herein, the terms "treat," "treatment" and "treating" refer to the reduction or amelioration of the progression, severity, and/or duration of a disease or a symptom related thereto, resulting from the administration of one or more therapies (including, but not limited to, the administration of one or more prophylactic or therapeutic agents, such as an isolated binding polypeptide provided herein). The term "treating," as used herein, can also refer to altering the disease course of the subject being treated. Therapeutic effects of treatment include, without limitation, preventing occurrence or recurrence of disease, alleviation of symptom (s), diminishment of direct or indirect pathological consequences of the disease, decreasing the rate of disease progression, amelioration or palliation of the disease state, and remission or improved prognosis.

Fc Domains

In certain aspects of the disclosure, Fc domains, e.g., Fc domain variants, are provided. As used herein, the term "Fc region" or "Fc domain" refers to the portion of a heavy chain constant region beginning in the hinge region just upstream of the papain cleavage site (i.e., residue 216 in IgG, taking the first residue of heavy chain constant region to be 114) and ending at the C-terminus of the antibody. Accordingly, a complete Fc region comprises at least a hinge domain, a CH2 domain, and a CH3 domain.

The Fc region of an antibody is involved in non-antigen binding, and can mediate effector function by binding to an Fc receptor. There are several different types of Fc receptors, which are classified based on the type of antibody that they recognize. For example, Fc-gamma receptors (FcγR) bind to IgG class antibodies, Fc-alpha receptors (FcαR) bind to IgA class antibodies, and Fc-epsilon receptors (FcεR) bind to IgE class antibodies. The neonatal Fc receptor (FcRn) interacts with the Fc region of an antibody to promote antibody recycling through rescue of normal lysosomal degradation. The FcγRs belong to a family that includes several members, e.g., FcγRI, FcγRIIa, FcγRIIb, FcγRIIIa, and FcγRIIIb.

The term "native Fc" or "wild-type Fc," as used herein, refers to a molecule corresponding to the sequence of a non-antigen-binding fragment resulting from digestion of an antibody or produced by other means, whether in monomeric or multimeric form, and can contain the hinge region. The original immunoglobulin source of the native Fc is typically of human origin and can be any of the immunoglobulins, such as IgG1 and IgG2. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a native Fc is a disulfide-bonded dimer resulting from papain digestion of an IgG. The term "native Fc," as used herein, is generic to the monomeric, dimeric, and multimeric forms.

The term "Fc domain variant," "Fc variant" or "modified Fc," as used herein, refers to a molecule or sequence that is modified from a native/wild-type Fc but still comprises a binding site for an FcR. Thus, the term "Fc variant" can comprise a molecule or sequence that is humanized from a non-human native Fc. Furthermore, a native Fc comprises regions that can be removed because they provide structural features or biological activities that are not required for the antibody-like binding polypeptides described herein. Thus, the term "Fc variant" comprises a molecule or sequence that lacks one or more native Fc sites or residues, or in which one or more Fc sites or residues has been modified, that affect or are involved in: (1) disulfide bond formation, (2) incompatibility with a selected host cell, (3)N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

As used herein, an "effector-competent Fc variant" or "effector-competent polypeptide" refers to an Fc domain that has one or more Fc effector functions as described further herein.

In certain exemplary embodiments, an Fc variant featured herein has one or more of increased serum half-life, enhanced FcRn binding affinity, enhanced FcRn binding affinity at acidic pH, enhanced FcγRIIIa binding affinity, and/or similar thermal stability, as compared to a wild-type Fc.

FcγRIIIa V158, or human CD16a-V receptor, or CD16a$^V$, refers to a polypeptide construct comprising a fragment of the CD16 human receptor binding to a Fc region of a natural antibody, mediating antibody-dependent cellular cytotoxicity and bearing a Valine (V) on position 158, which is also reported in the literature as allotype CD16a V158.

FcγRIIIa F158, or human CD16a-F receptor, or CD16a$^F$, refers to a polypeptide construct comprising a fragment of the CD16 human receptor binding to a Fc region of a natural antibody, mediating antibody-dependent cellular cytotoxicity and bearing a Phenylalanine (F) on position 158, which is also reported in the literature as allotype CD16a F158.

The term "Fc domain" as used herein encompasses native/wild-type Fc and Fc variants and sequences as defined herein. As with Fc variants and native Fc molecules, the term "Fc domain" includes molecules in monomeric or multimeric form, whether digested from whole antibody or produced by other means.

In certain exemplary embodiments, an Fc domain as described herein is thermally stabilized.

In certain exemplary embodiments, an Fc domain as described herein is glycosylated (e.g., via N-linked glycosylation). In certain exemplary embodiments, an Fc domain comprises N-linked glycosylation, e.g., at an N-linked glycosylation motif that contains the amino acid sequence NXT or NXS (X being any amino acid residue except proline). In certain exemplary embodiments, an Fc domain is glycosylated at amino acid position 297, according to EU numbering.

In certain exemplary embodiments, an Fc domain as described herein is effector-competent.

In certain exemplary embodiments, an Fc domain as described herein is any combination of thermally stabilized, glycosylated, and effector-competent.

Thermally-Stabilized Fc Domain Variants

The structure of constant antibody domains is similar to that of the variable domains consisting of β-strands connected with loops and short helices. The CH2 domain of the heavy constant regions exhibits weak carbohydrate-mediated interchain protein-protein interactions in contrast to the extensive interchain interactions exhibited in other domains. Isolated murine CH2 domains are relatively unstable at physiological temperature (Feige et al., 2004, *J. Mol. Biol.* 344:107-118), but previous efforts demonstrate that the thermostability of CH2 domains may be enhanced with the addition of intrachain disulfide bonds, and that these could be used as scaffolds for binders (Gong et al., 2009, *J. Biol. Chem.* 284:14203-210).

Effector-enhancing Fc domain variants that exhibit increased thermal instability (i.e., decreased thermal stability) relative to a wild-type Fc domain are known. For example, S239D/I332E and S239D/I332E/A330L variants lead to decreased stability of the CH2 domain as indicated by the lowering of melting temperature (Tm) in differential scanning calorimetry (DSC) analysis. G236A/S239D/A330L/I332E has a reduced protein thermal shift measurement when compared to wild-type, as well as a considerably reduced half-life in hFcγR transgenic mice. (See Liu et al. (2014) J. Biol. Chem. 289(6): 3571, and Liu et al. (2020) Antibodies 9(4): 64 for review.)

Effector-enhancing Fc domain variants having improved FcγR binding wherein stability is not significantly reduced as compared to wild-type are known. (See, e.g., Igawa et al., EP 2 940 135, e.g., Example 10.)

It has been further discovered that thermally-stabilized Fc domain variants may be produced by introducing one or more disulfide bonds in the Fc domain. Accordingly, in one aspect, the present disclosure provides an Fc domain variant comprising one or more engineered (e.g., non-native) disulfide bonds, e.g., intrachain disulfide bonds mediated, e.g., by one or more pairs of cysteines.

In certain exemplary embodiments, a disulfide bond is an intrachain disulfide bond between the two CH2 regions of an Fc domain. In certain exemplary embodiments, a disulfide bond is an intrachain disulfide bond between the two CH3 regions of an Fc domain. In certain exemplary embodiments, two or more intrachain disulfide bonds are present in between the two CH2 regions of an Fc domain and/or between the two CH2 regions of an Fc domain.

Thermal stability, or the propensity of an Fc domain (e.g., an Fc domain with or without a binding polypeptide) to unfold, may be determined using a variety of methods known in the art. For example, the unfolding or denaturation temperature can be measured by nano-format differential scanning calorimetry (nanoDSC) or nano-format differential scanning fluorimetry (nanoDSF) (Wen et al., 2020 Anal. Biochem. 593:113581). The detectable temperature at which a protein begins to unfold is the Tonset. As used herein, the term "Tm" refers to the melting temperature of a molecule. As used herein, the term "Tm1" refers to the unfolding temperature of the Fc domains of the disclosure, in particular the unfolding temperature of the CH2 domain.

In certain exemplary embodiments, the Tonset of a thermally-stabilized Fc domain variant (e.g., having one or more engineered disulfide bonds) is increased relative to an Fc domain variant that is not thermally stabilized. In certain exemplary embodiments, the Tonset of a thermally-stabilized Fc domain variant is increased by about 1.0° C., about 1.5° C., about 2.0° C., about 2.5° C., about 3.0° C., about 3.5° C., about 4.0° C., about 4.5° C., about 5.0° C., about 5.5° C., about 6.0° C., about 6.5° C., about 7.0° C., about 7.5° C., about 8.0° C., about 8.5° C., about 9.0° C., about 9.5° C., about 10.0° C., about 10.5° C., about 11.0° C., about 11.5° C., about 12.0° C., about 12.5° C., about 13.0° C., about 13.5° C., about 14.0° C., about 14.5° C., about 15.0° C., about 15.5° C., about 16.0° C., about 16.5° C., about 17.0° C., about 17.5° C., about 18.0° C., about 18.5° C., about 19.0° C., about 19.5° C., about 20.0° C., about 20.5° C., about 21.0° C., about 21.5° C., about 22.0° C., about 22.5° C., about 23.0° C., about 23.5° C., about 24.0° C., about 24.5° C. or about 25.0° C. relative to an Fc domain variant that is not thermally stabilized.

In certain exemplary embodiments, a thermally-stabilized Fc domain variant has one or more amino acid substitution pairs selected from the group consisting of cysteine substitutions at: amino acid positions 242 and 334; amino acid positions 240 and 334; amino acid positions 287 and 306; amino acid positions 292 and 302; amino acid positions 323 and 332; amino acid positions 259 and 306; amino acid positions 350 and 441; amino acid positions 343 and 431; amino acid positions 375 and 404; amino acid positions 375 and 396; and amino acid positions 348 and 439, according to EU numbering. (See Wozniak-Knopp et al., 2012, *PLoS One* 7: e30083; Jacobsen et al., 2017 J. Biol. Chem. 202: 1865-75; WO2014153063 for reviews.)

In certain exemplary embodiments, a thermally-stabilized Fc domain variant comprises an engineered (e.g., non-native) intrachain disulfide bond mediated by a pair of cysteines that substitute for (i) a leucine (L) at amino acid position 242 and a lysine (K) at amino acid position 334; (ii) an alanine (A) at amino acid position 287 and a leucine (L) at amino acid position 306; or (iii) an arginine (R) at amino acid position 292 and a valine (V) at amino acid position 302, according to EU numbering.

In certain exemplary embodiments, a thermally-stabilized Fc domain variant comprises an engineered (e.g., a non-native) intrachain disulfide bond mediated by a pair of cysteines that substitute for a leucine (L) at amino acid position 242 and a lysine (K) at amino acid position 334. In certain exemplary embodiments, a thermally-stabilized Fc domain variant comprises an engineered (e.g., a non-native) intrachain disulfide bond mediated by a pair of cysteines that substitute an alanine (A) at amino acid position 287 and a leucine (L) at amino acid position 306. In certain exemplary embodiments, a thermally-stabilized Fc domain variant comprises an engineered (e.g., a non-native) intrachain disulfide bond mediated by a pair of cysteines that substitute for an arginine (R) at amino acid position 292 and a valine (V) at amino acid position 302. In certain exemplary embodiments, a thermally-stabilized Fc domain variant may comprise at least one engineered intrachain disulfide bond. In certain exemplary embodiments, a thermally-stabilized Fc domain variant may comprise more than one engineered intrachain disulfide bond.

Effector-Enhancing Fc Domain Variants

In one aspect, the present disclosure provides an Fc domain variant comprising effector-enhancing amino acid substitutions.

In one embodiment, an Fc domain variant with altered FcγRIIIa binding comprising one or more amino acid substitutions as disclosed herein. In one embodiment, an Fc domain variant with enhanced FcγRIIIa binding affinity having one or more amino acid substitutions as disclosed herein. In one embodiment, an Fc domain variant with enhanced FcγRIIIa binding affinity comprises two or more amino acid substitutions as disclosed herein. In one embodiment, an Fc domain variant with enhanced FcγRIIIa binding affinity comprises three or more amino acid substitutions as disclosed herein. In one embodiment, an Fc domain variant with enhanced FcγRIIIa binding affinity comprises four or more amino acid substitutions as disclosed herein.

In one embodiment, an Fc domain variant with altered FcRn binding comprises an Fc domain having one or more amino acid substitutions as disclosed herein. In one embodiment, an Fc domain variant with enhanced FcRn binding affinity comprises an Fc domain having one or more amino acid substitutions as disclosed herein. In one embodiment, an Fc domain variant with enhanced FcRn binding affinity comprises an Fc domain having two or more amino acid substitutions as disclosed herein. In one embodiment, an Fc domain variant with enhanced FcRn binding affinity comprises an Fc domain having three or more amino acid substitutions as disclosed herein.

In some embodiments, an Fc domain variant may exhibit a species-specific FcRn binding affinity. In one embodiment, an Fc domain variant may exhibit human FcRn binding affinity. In one embodiment, an Fc domain variant may exhibit cyno FcRn binding affinity. In some embodiments, an Fc domain variant may exhibit cross-species FcRn binding affinity. Such an Fc domain variants are said to be cross-reactive across one or more different species. In one embodiment, an Fc domain variant may exhibit both human and cyno FcRn binding affinity.

The neonatal Fc receptor (FcRn) interacts with the Fc region of antibodies to promote recycling through rescue of normal lysosomal degradation. This process is a pH-dependent process that occurs in the endosomes at acidic pH (e.g., a pH less than 6.5) but not under the physiological pH conditions of the bloodstream (e.g., a non-acidic pH). In some embodiments, an Fc domain variant has enhanced FcRn binding affinity at an acidic pH compared to a wild-type Fc domain. In some embodiments, an Fc domain variant has enhanced FcRn binding affinity at pH less than 7, e.g., at about pH 6.5, at about pH 6.0, at about pH 5.5, at about pH 5.0, compared to a wild-type Fc domain. In some embodiments, an Fc domain variant has enhanced FcRn binding affinity at pH less than 7, e.g., at about pH 6.5, at about pH 6.0, at about pH 5.5, at about pH 5.0, compared to the FcRn binding affinity of a wild-type Fc domain at an elevated non-acidic pH. An elevated non-acidic pH can be, e.g., pH greater than 7, about pH 7, about pH 7.4, about pH 7.6, about pH 7.8, about pH 8.0, about pH 8.5, about pH 9.0.

In certain embodiments, it may be desired for an Fc domain variant to exhibit approximately the same FcRn binding affinity at non-acidic pH as a wild-type Fc domain. In some embodiments, it may be desired for an Fc domain variant to exhibit less FcRn binding affinity at non-acidic pH than a binding polypeptide comprising a modified Fc domain having the double amino acid substitution M428L/N434S, according to EU numbering (See U.S. Pat. No. 8,088,376). Accordingly, it may be desired an Fc domain variant to exhibit minimal perturbation to pH-dependent FcRn binding.

In some embodiments, an Fc domain variant having enhanced FcRn binding affinity at an acidic pH, has a reduced (i.e., slower) FcRn off-rate as compared to a wild-type Fc domain. In some embodiments, an Fc domain variant having enhanced FcRn binding affinity at an acidic pH compared to the FcRn binding affinity of the binding polypeptide at an elevated non-acidic pH, has a slower FcRn off-rate at the acidic pH compared to the FcRn off-rate of a wild-type Fc domain at the elevated non-acidic pH.

Certain embodiments include Fc domain variants in which at least one amino acid in one or more of the constant region domains has been deleted or otherwise altered so as to provide desired biochemical characteristics such as reduced or enhanced effector functions, the ability to non-covalently dimerize, increased ability to localize at the site of a tumor, reduced serum half-life, or increased serum half-life when compared with a whole, unaltered antibody of approximately the same immunogenicity.

In certain other embodiments, an Fc domain variant comprises constant regions derived from different antibody isotypes (e.g., constant regions from two or more of a human IgG1, IgG2, IgG3, or IgG4). In other embodiments, an Fc domain variant comprises a chimeric hinge (i.e., a hinge comprising hinge portions derived from hinge domains of different antibody isotypes, e.g., an upper hinge domain from an IgG4 molecule and an IgG1 middle hinge domain). In certain embodiments, the Fc domain may be mutated to increase or decrease effector function using techniques known in the art.

In some embodiments, an Fc domain variant has altered binding affinity to an Fc receptor. There are several different types of Fc receptors, which are classified based on the type of antibody that they recognize. For example, Fc-gamma receptors (FcγR) bind to IgG class antibodies, Fc-alpha receptors (FcαR) bind to IgA class antibodies, and Fc-epsilon receptors (FcεR) bind to IgE class antibodies. The FcγRs belong to a family that includes several members, e.g., FcγRI, FcγRIIa, FcγRIIb, FcγRIIIa, and FcγRIIIb. In some embodiments, an Fc domain variant has altered FcγRIIIa binding affinity, compared to a wild-type Fc domain. In some embodiments, an Fc domain variant has reduced FcγRIIIa binding affinity, compared to a wild-type Fc domain. In some embodiments, an Fc domain variant has enhanced FcγRIIIa binding affinity, compared to a wild-type Fc domain. In some embodiments, an Fc domain variant modified Fc domain has approximately the same FcγRIIIa binding affinity, compared to a wild-type Fc domain.

In certain embodiments, an Fc domain variant comprises an antibody constant region (e.g., an IgG constant region e.g., a human IgG constant region, e.g., a human IgG1 constant region) which mediates one or more effector functions. For example, binding of the C1-complex to an antibody constant region may activate the complement system. Activation of the complement system is important in the opsonization and lysis of cell pathogens. The activation of the complement system also stimulates the inflammatory response and may also be involved in autoimmune hypersensitivity. Further, antibodies bind to receptors on various cells via the Fc domain (Fc receptor binding sites on the antibody Fc region bind to Fc receptors (FcRs) on a cell). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. In some embodiments, an Fc domain variant, e.g., a binding polypeptide (e.g., an antibody or immunoadhesin) binds to an Fc-gamma receptor. In alternative embodiments, an Fc domain variant comprised a constant region which is devoid of one or more effector functions (e.g., ADCC activity) and/or is unable to bind Fcγ receptor.

In certain exemplary embodiments, an effector-enhancing Fc domain variant has one or more amino acid substitutions selected from the group consisting of: an aspartic acid (D) at amino acid position 221; a cysteine (C) at amino acid position 222; a tyrosine (Y) at amino acid position 234; an alanine (A) at amino acid position 236; a tryptophan (W) at amino acid position 236; an aspartic acid (D) at amino acid position 239; a leucine (L) at amino acid position 243; a glutamic acid (E) at amino acid position 267; a phenylalanine (F) at amino acid position 268; a proline (P) at amino acid position 292; an alanine (A) at amino acid position 298; a leucine (L) at amino acid position 300; an isoleucine (I) at amino acid position 305; a threonine (T) at amino acid position 324; a tryptophan (W) at amino acid position 326; an alanine (A) at amino acid position 326; a leucine (L) at amino acid position 330; a glutamic acid (E) at amino acid position 332; an alanine (A) at amino acid position 333; a serine (S) at amino acid position 333; an alanine (A) at amino acid position 334; an alanine (A) at amino acid position 336; an arginine (R) at amino acid position 345; and a leucine (L) at amino acid position 396, according to EU numbering. (See Saunders, 2009, *Front. Immunol.* doi: 10.3389/fimmu.2019.01296, for a review.)

In some embodiments, an Fc domain variant may comprise an amino acid substitution at positions selected from amino acid positions 236, 239, 330, and 332, according to EU numbering. In some embodiments, the substitutions may comprise an alanine (A) at amino acid position 236, an aspartic acid (D) at amino acid 239, a leucine (L) at amino acid position 330, and a glutamic acid (E) at amino acid position 332, according to EU numbering. In some embodiments, an Fc domain variant may comprise a double amino acid substitution at any two amino acid positions selected from an alanine (A) at amino acid position 236, aspartic acid (D) at amino acid 239, a leucine (L) at amino acid position 330, and a glutamic acid (E) at amino acid position 332. In some embodiments, an Fc domain variant may comprise a triple amino acid substitution at any three amino acid positions selected from an alanine (A) at amino acid position 236, an aspartic acid (D) at amino acid 239, a leucine (L) at amino acid position 330, and a glutamic acid (E) at amino acid position 332. In some embodiments, an Fc domain variant may comprise a quadruple amino acid substitution at any four amino acid positions selected from an alanine (A) at amino acid position 236, an aspartic acid (D) at amino acid 239, a leucine (L) at amino acid position 330, and a glutamic acid (E) at amino acid position 332. In some embodiments, an Fc domain variant may comprise the combination of amino acid substitutions comprising an aspartic acid (D) at amino acid 239 and a glutamic acid (E) at amino acid position 332. In some embodiments, an Fc domain variant may comprise the combination of amino acid substitutions comprising an alanine (A) at amino acid position 236, an aspartic acid (D) at amino acid position and a glutamic acid at position 332.

In some embodiments, an Fc domain variant may further comprise an amino acid substitution at amino acid positions 256 and/or 307, according to EU numbering. In some embodiments, an Fc domain variant may comprise the combination of amino acid substitutions comprising an aspartic acid (D) at amino acid positions 256 and a glutamine (Q) at amino acid position 307 (See Mackness et al., 2019 MAbs 11:1276-88; WO2019147973A1, incorporated in its entirety by reference herein).

Glycosylated Fc Domain Variants

In certain exemplary embodiments, an Fc domain variant is glycosylated. Glycosylation of antibodies at conserved positions in their constant regions is known to have a profound effect on antibody function, particularly effector functioning such as those described above, see for example, Boyd et al (Mol. Immunol, 32: 1311-1318, 1996). Glycosylation of an Fc domain variant of the present invention wherein one or more carbohydrate moiety is added, substituted, deleted or modified are contemplated. In some embodiments, the glycosylation of the Fc domain is an N-linked glycosylation. Introduction of an asparagine-X-serine or asparagine-X-threonine motif creates a potential site for enzymatic attachment of carbohydrate moieties and may therefore be used to manipulate the glycosylation of an Fc domain variant. In Raju et al. (Biochemistry 40: 8868-8876, 2001) the terminal sialylation of a TNFR-IgG immunoadhesin was increased through a process of re-galactosylation and/or re-sialylation using β-1,4-galactosyltransferace and/or alpha, 2,3 sialyltransferase. Increasing the terminal sialylation is believed to increase the half-life of the immunoglobulin.

Antibodies, in common with most glycoproteins, are typically produced as a mixture of glycoforms. This mixture is particularly apparent when antibodies are produced in eukaryotic, particularly mammalian cells. A variety of methods have been developed to manufacture defined glycoforms (see Zhang et al. 2004, Science 303: 371; Sears et al, 2001, Science 291: 2344; Wacker et al., 2002, Science 298: 1790; Davis et al. 2002, Chem. Rev. 102: 579; Hang et al., 2001, Acc. Chem. Res. 34: 727). In some embodiments, the glycosylated Fc domain comprises a native glycan at amino acid position 297, according to EU numbering. Glycosylation of the asparagine at amino acid position 297 in the CH2 domain of IgG1 is known to facilitate interaction between the Fc domain and FcγR. Elimination of this glycosylation site eliminates effector function (Leabman, et al., 2013, MAbs 5:896-903). In particularly exemplary embodiments, an Fc domain comprises wild-type levels, or near wild-type levels, of glycosylation at amino acid position 297, according to EU numbering.

In some embodiments, the glycosylated Fc domain variant comprises an engineered or non-native glycan. In some embodiments, the engineered or non-native glycan is a modified glycan that can be conjugated to a therapeutic molecule (e.g., antibody-drug conjugate).

Fc Domain Variants with Enhanced In Vivo Stability

In one aspect, the present disclosure provides an isolated Fc domain variant comprising enhanced in vivo stability (e.g., enhanced serum half-life or decreased clearance). As used herein, the term "in vivo stability" refers to the stability of the instantly disclosed effector-competent polypeptides to remain intact (e.g., limited degradation and/or unfolding), functional (e.g., retain binding activity), and retain a sufficiently high concentration in serum in elicit a measurable activity (e.g., target tumor cell killing). In certain embodiments, the isolated effector-competent polypeptide has improved in vivo stability compared to a wild-type Fc domain. In certain embodiments, the isolated effector-competent polypeptide has decreased in vivo clearance compared to a wild-type Fc domain.

As used herein, the term "serum half-life" refers to the time it takes a substance (e.g., the isolated Fc domain variants) to go from a maximum concentration in serum to half of said maximum concentration in serum. Serum half-life may, in part, be enhanced through enhanced binding affinity to FcRn. In certain exemplary embodiments, the isolated effector-competent polypeptide has enhanced binding affinity to the FcRn compared to a wild-type Fc domain.

In vivo stability, serum half-life, and clearance may be determined by any method know in the art (see Valente, et al., 2020 MAbs 12:13 https://doi.org/10.1080/19420862.2020.1829337). By way of example, the methods recited in Example 7 for performing pharmacokinetic (PK) analysis may be employed.

Fc-Containing Binding Polypeptides

In one aspect, the present disclosure provides an isolated Fc domain variant comprising or complexed with (e.g., fused to) at least one binding domain (e.g., at least one binding polypeptide). In certain embodiments, the binding domain comprises one or more antigen binding domains. The antigen binding domains need not be derived from the same molecule as the parental Fc domain. In certain embodiments, the Fc domain variant is present in an antibody.

In one embodiment, an Fc domain variant is present in an antibody or is complexed with an antibody. Any antibody from any source or species can be employed with an Fc domain variant disclosed herein. Suitable antibodies include without limitation, chimeric antibodies, humanized antibodies, or human antibodies. Suitable antibodies include without limitation, full-length antibodies, monoclonal antibodies, polyclonal antibodies, or single-domain antibodies, such as VHH antibodies.

In certain exemplary embodiments, an Fc domain variant may be bound to or complexed with an antigen-binding fragment of an antibody. The term "antigen-binding fragment" refers to a polypeptide fragment of an immunoglobulin or antibody which binds antigen or competes with intact antibody (i.e., with the intact antibody from which they were derived) for antigen binding (i.e., specific binding). Antigen-binding fragments can be produced by recombinant or biochemical methods that are well known in the art. Exemplary antigen-binding fragments include Fv, Fab, Fab', and (Fab')2. In certain exemplary embodiments, a binding polypeptide of the current disclosure comprises at least one antigen-binding fragment and an Fc domain variant.

In some embodiments, the binding polypeptide comprises a single chain variable region sequence (ScFv). Single chain variable region sequences comprise a single polypeptide having one or more antigen binding sites, e.g., a VL domain linked by a flexible linker to a VH domain. ScFv molecules can be constructed in a VH-linker-VL orientation or VL-linker-VH orientation. The flexible hinge that links the VL and VH domains that make up the antigen binding site includes from about 10 to about 50 amino acid residues. Connecting peptides are known in the art. Binding polypeptides may comprise at least one scFv and/or at least one constant region. In one embodiment, a binding polypeptide of the current disclosure may comprise at least one scFv linked or fused to an Fc domain variant.

In some embodiments, a binding polypeptide of the current disclosure is a multivalent (e.g., tetravalent) antibody which is produced by fusing a DNA sequence encoding an antibody with a ScFv molecule (e.g., an altered ScFv molecule). For example, in one embodiment, these sequences are combined such that the ScFv molecule (e.g., an altered ScFv molecule) is linked at its N-terminus or C-terminus to an Fc domain variant via a flexible linker (e.g., a gly/ser linker). In another embodiment a tetravalent antibody of the current disclosure can be made by fusing an ScFv molecule to a connecting peptide, which is fused to an Fc domain variant to construct an ScFv-Fab tetravalent molecule.

In another embodiment, a binding polypeptide of the current disclosure is an altered minibody. An altered minibody of the current disclosure is a dimeric molecule made up of two polypeptide chains each comprising an ScFv molecule which is fused to an Fc domain variant via a connecting peptide. Minibodies can be made by constructing an ScFv component and connecting peptide components using methods described in the art (see, e.g., U.S. Pat. No. 5,837,821 or WO 94/09817AI). In another embodiment, a tetravalent minibody can be constructed. Tetravalent minibodies can be constructed in the same manner as minibodies, except that two ScFv molecules are linked using a flexible linker. The linked scFv-scFv construct is then joined to an Fc domain variant.

In another embodiment, a binding polypeptide of the current disclosure comprises a diabody. Diabodies are dimeric, tetravalent molecules each having a polypeptide similar to scFv molecules, but usually having a short (less than 10, e.g., about 1 to about 5) amino acid residue linker connecting both variable domains, such that the VL and VH domains on the same polypeptide chain cannot interact. Instead, the VL and VH domain of one polypeptide chain interact with the VH and VL domain (respectively) on a second polypeptide chain (see, for example, WO 02/02781). Diabodies of the current disclosure comprise an scFv-like molecule fused to an Fc domain variant.

In another embodiment, a binding polypeptide of the current disclosure comprises a single-domain antibody (sdAb), also referred to as a VHH or a nanobody. Nanobody® is registered trademark of Ablynx. VHHs comprise variable heavy chain domains devoid of light chains. Similar to conventional VH domains, VHHs contain four FRs and three CDRs. VH Hs have advantages over conventional antibodies. As they are about ten times smaller than IgG molecules, properly folded functional VHHs can be produced by in vitro expression while achieving high yield. Furthermore, VHHs are very stable, and resistant to the action of proteases. The properties and production of VHHs have been reviewed by Harmsen and De Haard H J (Appl. Microbiol. Biotechnol. 2007 November; 77(1):13-22).

In certain exemplary embodiments, an Fc domain is fused with one or more VHHs.

In other embodiments, binding polypeptides comprise multi-specific or multivalent antibodies comprising one or more variable domain in series on the same polypeptide chain, e.g., tandem variable domain (TVD) polypeptides. Exemplary TVD polypeptides include the "double head" or "Dual-Fv" configuration described in U.S. Pat. No. 5,989,830. In the Dual-Fv configuration, the variable domains of two different antibodies are expressed in a tandem orientation on two separate chains (one heavy chain and one light chain), wherein one polypeptide chain has two VH domains in series separated by a peptide linker (VH1-linker-VH2) and the other polypeptide chain consists of complementary VL domains connected in series by a peptide linker (VL1-linker-VL2). In the cross-over double head configuration, the variable domains of two different antibodies are expressed in a tandem orientation on two separate polypeptide chains (one heavy chain and one light chain), wherein one polypeptide chain has two VH domains in series separated by a peptide linker (VH1-linker-VH2) and the other polypeptide chain consists of complementary VL domains connected in series by a peptide linker in the opposite orientation (VL2-linker-VL1). Additional antibody variants based on the "Dual-Fv" format include the Dual-Variable-Domain IgG (DVD-IgG) bispecific antibody (see U.S. Pat. No. 7,612,181 and the TBTI format (see US 2010/0226923 A1). In some embodiments, binding polypeptides comprise multi-specific or multivalent antibodies comprising one or more variable domain in series on the same polypeptide chain fused to an Fc domain variant.

In another embodiment, a binding polypeptide comprises a cross-over dual variable domain IgG (CODV-IgG) bispecific antibody based on a "double head" configuration (see US20120251541 A1, which is incorporated by reference herein in its entirety).

In other embodiments, a binding polypeptide comprises a CrossMab or a CrossMab-Fab multispecific format (see WO2009080253 and Schaefer, et al., PNAS (2011), 108: 11187-1191). Antibody variants based on the CrossMab format have a crossover of antibody domains within one arm of a bispecific IgG antibody enabling correct chain association.

In other embodiments, the glycosylated effector-competent polypeptide comprises a multispecific antibody in a T cell engager format. A "T cell engager" refers to binding proteins directed to a host's immune system, more specifically the T cells' cytotoxic activity as well as directed to a tumor target protein. In some embodiments, the isolated effector-competent polypeptide comprises a multispecific antibody in an NK cell engager format. An "NK cell engager" refers to binding proteins comprising monoclonal antibody fragments targeting activating NK cell receptors, antigen-specific targeting regions, and an Fc region (Gauthier, et al. Cell (2019), 177: 1701-13).

A binding polypeptide of the present disclosure, comprising an Fc domain variant described herein, can include the CDR sequences or the variable domain sequences of a known "parent" antibody. In some embodiments, the parent antibody and the antibody of the disclosure can share similar or identical sequences except for modifications to the Fc domain as disclosed herein.

In another embodiment, the binding polypeptide comprises a therapeutic polypeptide. In some embodiments, the therapeutic polypeptide may be a receptor, a ligand, or an enzyme. In some embodiments, the therapeutic polypeptide may be a clotting factor. In some embodiments, the clotting factor is selected from the group consisting of FI, FII, FIII, FIV, FV, FVI, FVII, FVIII, FIX, FX, FXI, FXII, FXIII), VWF, prekallikrein, high-molecular weight kininogen, fibronectin, antithrombin III, heparin cofactor II, protein C, protein S, protein Z, Protein Z-related protease inhibitor (ZPI), plasminogen, alpha 2-antiplasmin, tissue plasminogen activator (tPA), urokinase, plasminogen activator inhibitor-1 (PAI-1), plasminogen activator inhibitor-2 (PAI2), any zymogen thereof, any active form thereof, and any combination thereof. In some embodiments, the therapeutic polypeptide may be a growth factor. The growth factor can be selected from any growth factor known in the art. In some embodiments, the growth factor is a hormone, in other embodiments, the growth factor is a cytokine. In some embodiments, the growth factor is a chemokine. In some embodiments, the binding polypeptide comprises a therapeutic molecule or therapeutic polypeptide linked to the N-terminus and/or the C-terminus of the Fc domain of the present invention. In some embodiments, the polypeptide is an Fc-fusion polypeptide.

Nucleic Acids and Vectors

In one aspect, polynucleotides encoding the Fc domain variants and/or the binding polypeptides disclosed herein are provided. Methods of making an Fc domain variant and/or a binding polypeptide comprising expressing these polynucleotides are also provided.

Polynucleotides encoding the Fc domain variants and/or the binding polypeptides disclosed herein are typically inserted in an expression vector for introduction into host cells that may be used to produce the desired quantity of the claimed antibodies, therapeutic polypeptides, and Fc-fusion proteins. Accordingly, in certain aspects, the invention provides expression vectors comprising polynucleotides disclosed herein and host cells comprising these vectors and polynucleotides.

The term "vector" or "expression vector" is used herein for the purposes of the specification and claims, to mean vectors used for introducing into and expressing a desired gene in a cell. As known to those skilled in the art, such vectors may easily be selected from the group consisting of plasmids, phages, viruses and retroviruses. In general, a vector will comprise a selection marker, appropriate restriction sites to facilitate cloning of the desired gene and the ability to enter and/or replicate in eukaryotic or prokaryotic cells.

Numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV), or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals. In some embodiments the cloned variable region genes are inserted into an expression vector along with the heavy and light chain constant region genes (such as human genes) synthesized as discussed above.

In other embodiments, a glycosylated effector-competent polypeptide as described herein may be expressed using polycistronic constructs. In such expression systems, multiple gene products of interest such as heavy and light chains of antibodies may be produced from a single polycistronic construct. These systems advantageously use an internal ribosome entry site (IRES) to provide relatively high levels of polypeptides in eukaryotic host cells. Compatible IRES sequences are disclosed in U.S. Pat. No. 6,193,980 which is incorporated by reference herein. Those skilled in the art will appreciate that such expression systems may be used to effectively produce the full range of polypeptides disclosed in the instant application.

More generally, once a vector or DNA sequence encoding an Fc domain variant and/or a binding polypeptide of the present disclosure has been prepared, the expression vector may be introduced into an appropriate host cell. That is, the host cell may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, e.g., Ridgway, A. A. G. "Mammalian Expression Vectors" Chapter 24.2, pp. 470-472 Vectors, Rodriguez and Denhardt, Eds. (Butterworths, Boston, MA 1988). The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refer to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

In one embodiment, the host cell line used for expression of an Fc domain variant and/or a binding polypeptide is of eukaryotic or prokaryotic origin. In one embodiment, the host cell line used for expression of an Fc domain variant and/or a binding polypeptide is of bacterial origin. In one embodiment, the host cell line used for expression of an Fc domain variant and/or a binding polypeptide is of mammalian origin. Those skilled in the art can determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), BFA-1c1BPT (bovine endothelial cells), RAJI (human lymphocyte), 293 (human kidney). In one embodiment, the cell line provides for altered glycosylation, e.g., afucosylation, of the antibody expressed therefrom (e.g., PER.C6® (Crucell) or FUT8-knock-out CHO cell lines (POTELLIGENT™ cells) (Biowa, Princeton, NJ)). In one embodiment NS0 cells may be used. Host cell lines are typically available from commercial services, the American Tissue Culture Collection or from published literature.

In vitro production allows scale-up to give large amounts of the desired Fc domain variant and/or binding polypeptide. Techniques for mammalian cell cultivation under tissue culture conditions are known in the art and include homogeneous suspension culture, e.g., in an airlift reactor or in a continuous stirrer reactor, or immobilized or entrapped cell culture, e.g., in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose and/or (immuno-) affinity chromatography.

One or more genes encoding glycosylated Fc domain variants and/or binding polypeptides can also be expressed in non-mammalian cells such as bacteria or yeast or plant cells. In this regard, it will be appreciated that various unicellular non-mammalian microorganisms such as bacteria can also be transformed, i.e., those capable of being grown in cultures or fermentation. Bacteria, which are susceptible to transformation, include members of the enterobacteriaceae, such as strains of *Escherichia coli* or *Salmonella*; *Bacillaceae*, such as *Bacillus subtilis*; Pneumococcus; *Streptococcus*, and *Haemophilus influenzae*. It will further be appreciated that, when expressed in bacteria, the Fc domain variants and/or binding polypeptides can become part of inclusion bodies. The Fc domain variants and/or binding polypeptides must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trpI lesion as a characteristic of the yeast host cell genome then provides an effective environment for detecting transformation by growth in the absence of tryptophan.

Methods of Use/Treatment

In one aspect, the invention provides methods of treating a disease or disorder in a subject in need thereof comprising administering to the subject an effective amount of an Fc domain variant disclosed herein. In certain embodiments, the present disclosure provides kits and methods for the treatment of diseases and disorders, e.g., cancer in a mammalian subject in need of such treatment.

The Fc domain variants of the current disclosure are useful in a number of different applications. For example, in one embodiment, the subject Fc domain variants are useful for reducing or eliminating cells bearing an epitope recognized by the binding domain of the Fc domain variant. In another embodiment, the subject Fc domain variants are effective in reducing the concentration of or eliminating soluble antigen in the circulation. In another embodiment, the subject Fc domain variants are effective as T-cell engagers. In one embodiment, the Fc domain variants may reduce tumor size, inhibit tumor growth, and/or prolong the survival time of tumor-bearing animals. Accordingly, this disclosure also relates to a method of treating tumors in a human or other animal by administering to such human or animal an effective, non-toxic amount of an Fc domain variant.

In another embodiment, the subject Fc domain variants are useful for the treatment of other disorders, including, without limitation, infectious diseases, autoimmune disorders, inflammatory disorders, lung diseases, neuronal or neurodegenerative diseases, liver diseases, diseases of the spine, diseases of the uterus, depressive disorders and the like. Non-limiting examples of infectious diseases include those caused by RNA viruses (e.g., orthomyxoviruses (e.g., influenza), paramyxoviruses (e.g., respiratory syncytial virus, parainfluenza virus, metapneumovirus), rhabdoviruses (e.g., rabies virus), coronaviruses (e.g., SARS-CoV), alphaviruses (e.g., Chikungunya virus) lentiviruses (e.g., HIV) and the like) or DNA viruses. Examples of infectious diseases also include, without limitation, bacterial infectious diseases, caused by, e.g., *Staphylococcus aureus, Staphylococcus epidermidis, Enterococcus, Streptococcus, Escherichia coli*, and other infectious diseases including, e.g., those caused by *Candida albicans*. Other infectious diseases include, without limitation, malaria, SARS, yellow fever, Lyme borreliosis, leishmaniasis, anthrax and meningitis. Exemplary autoimmune disorders include, but are not limited to, psoriasis and lupus. Accordingly, this disclosure relates to a method of treating various conditions that would benefit from using a subject effector-competent polypeptide having, e.g., enhanced half-life.

One skilled in the art would be able, by routine experimentation, to determine what an effective, non-toxic amount of Fc domain variant would be for the purpose of treating malignancies. For example, a therapeutically active amount of a Fc domain variant of the present disclosure may vary according to factors such as the disease stage (e.g., stage I versus stage IV), age, sex, medical complications (e.g., immunosuppressed conditions or diseases) and weight of the subject, and the ability of the modified antibody to elicit a desired response in the subject. The dosage regimen may be adjusted to provide the optimum therapeutic response. For example, several divided doses may be administered daily, or the dose may be proportionally reduced as indicated by the exigencies of the therapeutic situation.

In general, the compositions provided in the current disclosure may be used to prophylactically or therapeutically treat any neoplasm comprising an antigenic marker that allows for the targeting of the cancerous cells by the Fc domain variant.

Pharmaceutical Compositions and Administration Thereof

Methods of preparing and administering Fc domain variants of the current disclosure to a subject are well known to or are readily determined by those skilled in the art. The route of administration of the binding polypeptides of the current disclosure may be oral, parenteral, by inhalation or topical. The term parenteral as used herein includes intravenous, intraarterial, intraperitoneal, intramuscular, subcutaneous, rectal or vaginal administration. While all these forms of administration are clearly contemplated as being within the scope of the current disclosure, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. In some embodiments, Fc domain variants can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Aqueous carriers include water, alcoholic/aqueous solutions, emulsions or suspensions, including saline and buffered media. In the compositions and methods of the current disclosure, pharmaceutically acceptable carriers include, but are not limited to, 0.01-0.1 M, e.g., 0.05 M phosphate buffer, or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will typically be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

In many cases, isotonic agents will be included, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an Fc domain variant by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, exemplary methods of preparation include vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture will typically have labels or package inserts indicating that the associated compositions are useful for treating a subject suffering from, or predisposed to autoimmune or neoplastic disorders.

Effective doses of the compositions of the present disclosure, for the treatment of the above described conditions vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

Fc domain variants of the current disclosure can be administered on multiple occasions. Intervals between single dosages can be weekly, monthly or yearly. Intervals can also be irregular as indicated by measuring blood levels of Fc domain variant or antigen in the patient. In some methods, dosage is adjusted to achieve a plasma modified binding polypeptide concentration of about 1-1000 μg/ml and in some methods about 25-300 μg/ml. Alternatively, Fc domain variants can be administered as a sustained release formulation, in which case less frequent administration is required. For antibodies, dosage and frequency vary depending on the half-life of the antibody in the patient. In general, humanized antibodies show the longest half-life, followed by chimeric antibodies and nonhuman antibodies.

The dosage and frequency of administration can vary depending on whether the treatment is prophylactic or therapeutic. In prophylactic applications, compositions containing the present polypeptides or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from about 0.1 to about 25 mg per dose, especially about 0.5 to about 2.5 mg per dose. A relatively low dosage is administered at relatively infrequent intervals over a long period of time. Some patients continue to receive treatment for the rest of their lives. In therapeutic applications, a relatively high dosage (e.g., from about 1 to 400 mg/kg of antibody per dose, with dosages of from about 5 to 25 mg being more commonly used for radioimmunoconjugates and higher doses for cytotoxin-drug modified antibodies) at relatively short intervals is sometimes required until progression of the disease is reduced or terminated, or until the patient shows partial or complete amelioration of disease symptoms. Thereafter, the patient can be administered a prophylactic regime.

Fc domain variants of the current disclosure can optionally be administered in combination with other agents that are effective in treating the disorder or condition in need of treatment (e.g., prophylactic or therapeutic). Effective single treatment dosages (i.e., therapeutically effective amounts) of $^{90}$Y-labeled modified antibodies of the current disclosure range from between about 5 and about 75 mCi, such as between about 10 and about 40 mCi. Effective single treatment non-marrow ablative dosages of $^{131}$I-modified antibodies range from between about 5 and about 70 mCi, or between about 5 and about 40 mCi. Effective single treatment ablative dosages (i.e., may require autologous bone marrow transplantation) of $^{131}$I-labeled antibodies range from between about 30 and about 600 mCi, such as between about 50 and less than about 500 mCi. In conjunction with a chimeric antibody, owing to the longer circulating half-life vis-a-vis murine antibodies, an effective single treatment non-marrow ablative dosages of iodine-131 labeled chimeric antibodies range from between about 5 and about 40 mCi, such as less than about 30 mCi. Imaging criteria for, e.g., the $^{111}$In label, are typically less than about 5 mCi.

While the Fc domain variants may be administered as described immediately above, it must be emphasized that in other embodiments the polypeptide may be administered to otherwise healthy patients as a first line therapy. In such embodiments, the Fc domain variants may be administered to patients having normal or average red marrow reserves and/or to patients that have not, and are not, undergoing treatment. As used herein, the administration of the polypeptides in conjunction or combination with an adjunct therapy means the sequential, simultaneous, coextensive, concurrent, concomitant, or contemporaneous administration or application of the therapy and the disclosed antibodies. Those skilled in the art will appreciate that the administration or application of the various components of the combined therapeutic regimen may be timed to enhance the overall effectiveness of the treatment.

As previously discussed, the Fc domain variants of the present disclosure, antibodies, therapeutic polypeptides, or Fc domain variant-fusion polypeptides thereof, may be administered in a pharmaceutically effective amount for the in vivo treatment of mammalian disorders. In this regard, it will be appreciated that the disclosed Fc domain variants will be formulated to facilitate administration and promote stability of the active agent.

A pharmaceutical composition in accordance with the present disclosure can comprise a pharmaceutically acceptable, non-toxic, sterile carrier such as physiological saline, nontoxic buffers, preservatives and the like. For the purposes of the instant application, a pharmaceutically effective amount of the Fc domain variant, conjugated or unconjugated to a therapeutic agent, shall be held to mean an amount sufficient to achieve effective binding to an antigen and to achieve a benefit, e.g., to ameliorate symptoms of a disease or disorder or to detect a substance or a cell. In the case of tumor cells, the polypeptide can interact with selected antigens on neoplastic or immunoreactive cells and provide for an increase in the death of those cells. Of course, the pharmaceutical compositions of the present disclosure may be administered in single or multiple doses to provide for a pharmaceutically effective amount of the modified binding polypeptide.

In keeping with the scope of the present disclosure, the Fc domain variants of the disclosure may be administered to a human or other animal in accordance with the aforementioned methods of treatment in an amount sufficient to produce a therapeutic or prophylactic effect. The Fc domain variants of the disclosure can be administered to such human or other animal in a conventional dosage form prepared by combining the antibody of the disclosure with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of binding polypeptides described in the current disclosure may prove to be particularly effective.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXAMPLES

The present invention is further illustrated by the following examples, which should not be construed as further limiting.

Figure 1B:
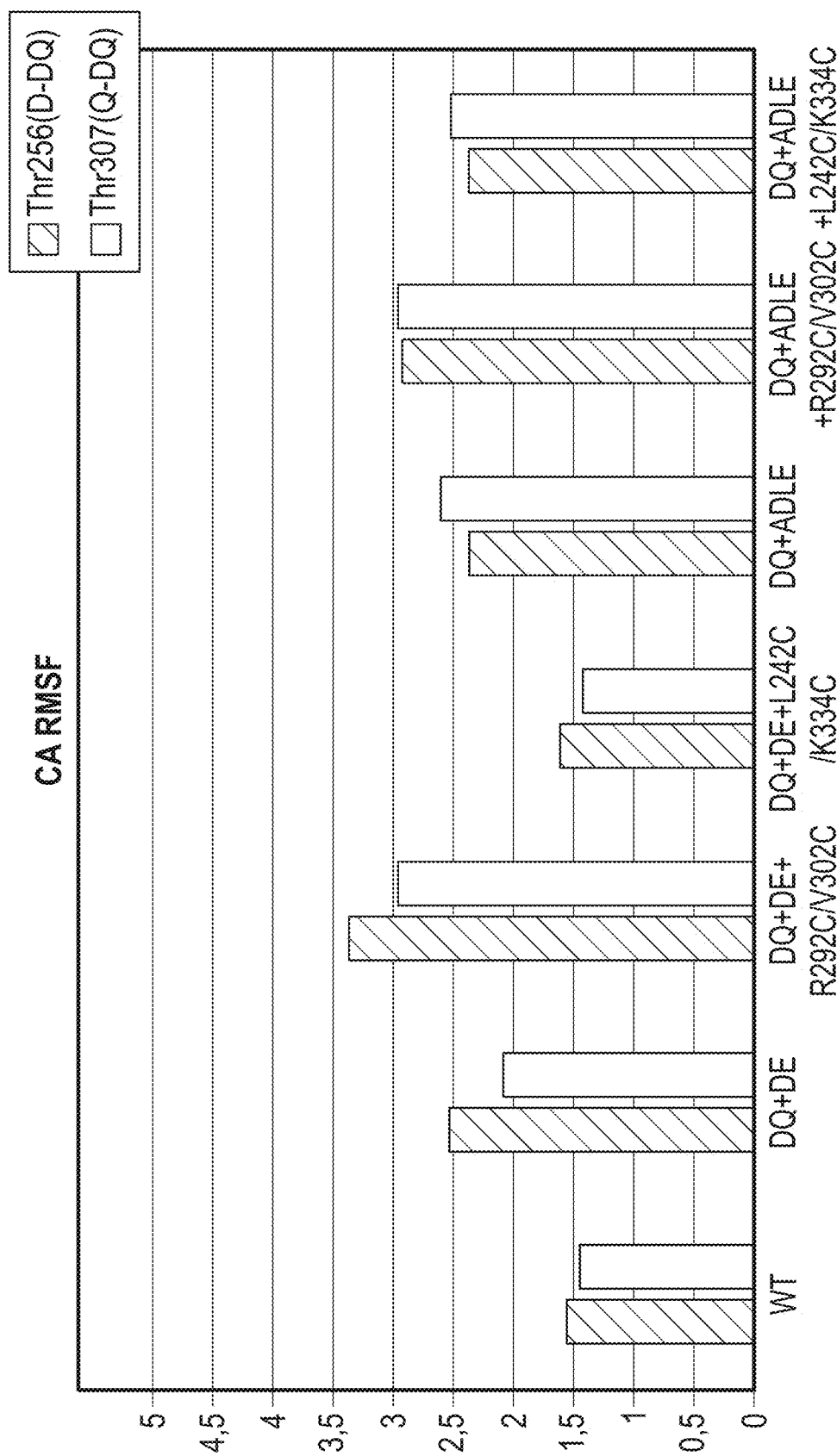

Example 1: In Silico Model and Identification of the Disulfide Bond for Increased Stability In order to characterize the potential stabilization effect of engineered disulfide bonds in the CH2 region of the Fc domain, molecular dynamics (MD) simulations were carried out on the Fc domain taken from the PDB structure 1HZH. All systems were simulated at 300 K and 370 K to estimate the impact of the thermal shock and determine potential weak interactions on the domain. The simulations were performed for the following Fc variants: WT IgG1 Fc domain, DE+DQ, ADLE+DQ, DE+DQ+L242C/K334C, DE+DQ+R292C/V302C, ADLE+DQ+L242C/K334C, and ADLE+DQ+R292C/V302C. Results were reported as the mean frequency of hydrophobic contacts (FIG. 1A) for residue I332E as well as the mean flexibility of the regions containing the mutations expressed by the Root Mean Square Fluctuation (RMSF) index of the respective carbon alpha (FIG. 1B) at temperatures of either 300 K or 370 K.

Results

The introduction of a negative charge (I332E) in the CH2 domain brings to a loss of hydrophobic contacts mean frequencies (e.g., DQ+DE and DQ+ADLE systems—FIG. 1A), with the potential disruption of the hydrophobic core of the domain. The introduction of R292C+V302O or L242C+K334C mutations partially restores or improves these contacts.

The flexibility index (RMSF—FIG. 1B) of the DQ mutations has been monitored for all the system to estimate the potential impact on half-life extension for all the variants. The systems containing the I332E mutation in the context of the DQ mutations, appear to show higher flexibility with respect of the WT at positions 256 and 307. The introduction of DSB stabilizations appears to partially improve the flexibility index towards the WT behavior (e.g., DQ DE L242C+K3340—FIG. 1B).

Figure 2:
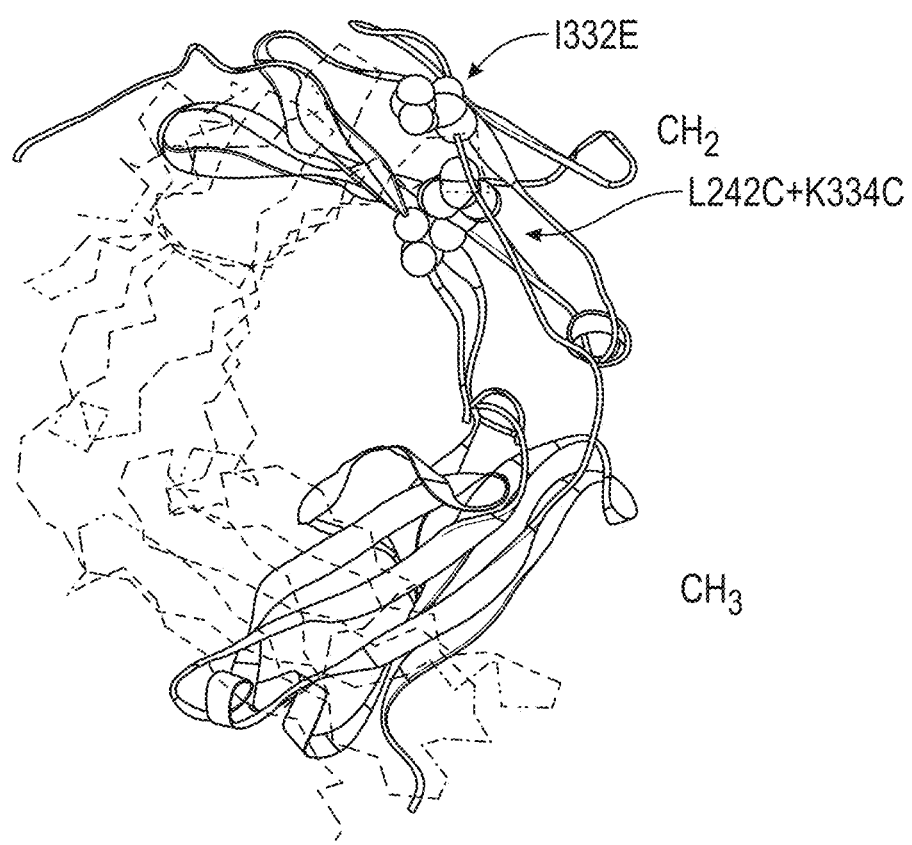
FIG. 2 depicts an example of DSB grafting on the Fc CH2 domain (in lines—ribbons) with I332E (green CPK rendering) and an L242C+K3340 engineered disulfide bond (orange CPK rendering) in close structural proximity.

FIG. 2 depicts an example of DSB grafting on the Fc CH2 domain (in lines—ribbons) with I332E (green CPK rendering) and an L242C+K334C engineered disulfide bond (orange CPK rendering) in close structural proximity.

Figure 3:
FIG. 3 depicts an example of non-covalent bond networks for I332 (left panel, hydrophobic contacts highlighted in dotted lines) and I332E (right panel, electrostatic contact highlighted in dotted line).

FIG. 3 depicts an example of non-covalent bond networks for I332 (left panel, hydrophobic contacts highlighted in dotted lines) and I332E (right panel, electrostatic contact highlighted in dotted line).

The structural comparison between the two images in FIG. 3 pointed out that the I332E mutation introduced a negative charge within the hydrophobic core of the CH2 domain. This mutation yields to a loss of hydrophobic contacts within the hydrophobic core, and thus has been identified as potential driving phenomenon with respect of the poor thermal stability.

The rationale of the in silico study was to find possible positions for disulfide stabilization to create new covalent sulfur-sulfur contacts to restore the enthalpy loss due to hydrophobic network disruption, rescuing the hydrophobic network that is at the basis of the normally N-glycosylated CH2 domain fold. Several disulfide bonds have been previously tested to stabilize aglycosylated IgG1 (see, Gong et al. 2009. J. Biol. Chem. 284, 14203-14210; Jacobsen et al. 2017. J. Biol. Chem. 292, 1865-1875). Among them, two disulfide schemes fit with the aforementioned hypothesis, and the positions and mutations were L242C+K334C and R292C+V302C (see FIG. 4).

As a negative control, two residues were chosen far away from position 332 to introduce a disulfide bridge, the positions and mutations were A287C+L306C. This disulfide stabilization is flanking the hydrophobic core and is positioned at the boundaries of the beta fold characterizing the IgG CH2 domain (see FIG. 5). Even though the introduction of a covalent sulfur-sulfur bond may stabilize an aglycosylated IgG1 scaffold, the distance from the I332E mutation should make this disulfide stabilization considered as inefficient within an enhanced effector function scaffold containing the I332E mutation.

Figure 4:
FIG. 4 depicts an example of positions chosen for DSB mutations. On the left panel, L242+K334 (sticks within the circle). On the right panel, R292 and V302 (sticks within the circle).

FIG. 4 depicts an example of positions chosen for DSB mutations. On the left panel, L242+K334 (sticks within the circle). On the right panel, R292 and V302 (sticks within the circle).

Figure 5:
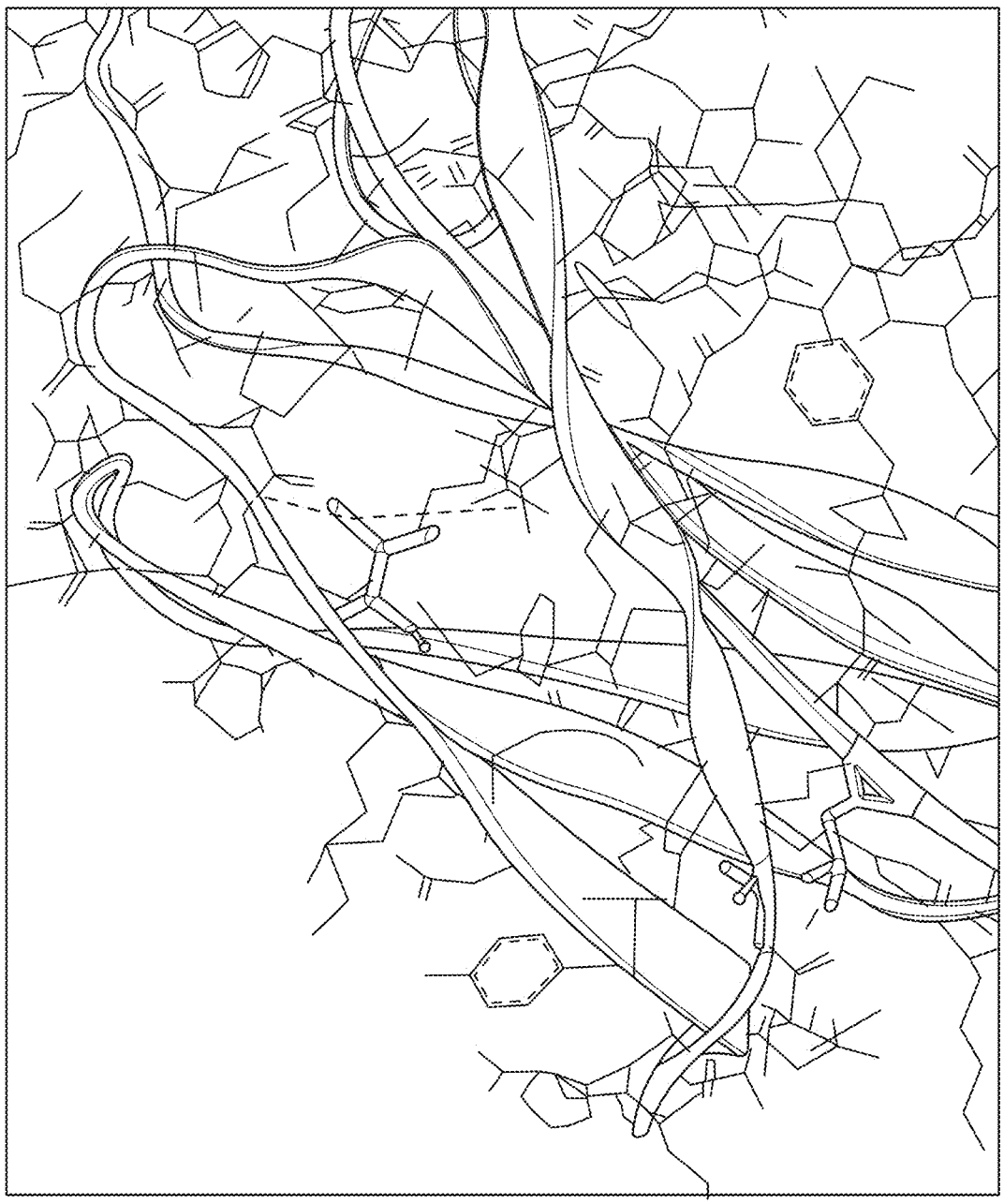
FIG. 5 depicts A287 and L306 (lower yellow sticks) positions that were chosen as a negative control. The two residues are close to the FcRn binding surface and are at the boundaries of the IgG CH2 domain, with a predicted structural impact lower than the two previous DSB schemes.

FIG. 5 depicts A287 and L306 (lower yellow sticks) positions that were chosen as a negative control. The two residues are close to the FcRn binding surface and are at the boundaries of the IgG CH2 domain, with a predicted structural impact lower than the two previous DSB schemes.

In Silico Model and Influence of Disulfide Bond on Binding to C1q, FcγRIIIa, FcγRIIa and FcRn The influence of the disulfide bond on binding to C1q, FcγRIIIa, FcγRIIa and FcRn was determined using an in silico model.

Materials and Methods

This analysis has been performed on available crystal structures, PDB IDs: 6FCZ-C1q, 5D6D-FcγRIIIa in complex with GASDALIE Fc, 3RY6-FcγRIIa and 4NOU-FcRn. The low resolution of two of the structures (6FCZ—model based on cryo-EM structure of the Fc in complex with C1q, and 3RY6—X-Ray structure with 3.80 Å resolution of the Fc in complex with FcγRIIa must be considered and the conclusions may have a bias due to the poor resolution. The interacting residues have been determined by selecting all the Fc residues within 5 Å from the receptor and cross-checked with the enhancing effector function mutations and DSB mutations. As the chosen interaction distance is higher than the resolution of the two aforementioned crystal structures (5 Å and 3.80 Å, respectively), this should reduce the bias, which should be determinant only in the case of the determination of residue-residue direct interaction evaluations, and not in the case of the determination of a whole interaction surface, which is the current case.

Contact Residues with C1q

This analysis showed that the closest residues found in the two CH2 domains are the following, for Fc chain 1 and chain 2 respectively.

Fc chain 1: E233, L234, L235, G236, G237, K322, S324, N325, K326, A327, L328, P329, A330, P331, E333. Residues G236 and A330 are respectively carrying the mutations G236A and A330L in the ADLE and ADE schemes. A330 (L in ADLE) is in direct contact with the C1q receptor and may have a direct impact on binding when mutated to leucine. Moreover, P331 is in direct contact with C1q and is directly preceding I332 (E in ADE/DE/ADLE).

Fc chain 2: H268, E269, E294, S298, Y300. These positions do not contain any of the engineered mutations, neither enhanced effector function nor stabilizing.

Based on this analysis, the DE, ADE and ADLE mutations might impact binding to C1q due to the residue in contact or close to the C1q receptor. The DSB positions are not found within the closest residues to C1q and should not impact the binding to C1q. T256D and T307Q mutations are far from the interaction surface, and thus should not be impact binding with C1q.

Contact Residues with FcγRIIIa

This analysis showed that the closest residues found in the two CH2 domains are the following, for Fc chain 1 and chain 2 respectively:

Fc chain 1: A236, G237, P238, D239, D265, V266, S267, H268, D270, Y296, N297, S298, T299 and A327.

Fc chain 2: G236, G237, P238, S239, K326, A327, L328, P329, A330, I332.

The residues in bold belong to the DE, ADE and ADLE enhancing effector function mutations. It explained and was reported to increase binding to FcγRIIIa. Whereas none of the aforementioned positions contain neither of the DSB mutations, which should not impact the binding to FcγRIIIa. T256D and T307Q mutations are far from the interaction surface, and thus should not be impact binding with FcγRIIIa.

Contact Residues with FcγRIIa

This analysis showed that the closest residues found in the two CH2 domains are the following, for Fc chain 1 and chain 2 respectively: Fc chain 1: L235, G236, G237, P238, K326, A327, L328, P329. Residue G236 carries the mutation G236A in the ADLE and ADE schemes.

Fc chain 2: L234, L235, G236, G237, P238, S239, V264, D265, V266, S267, N297, S298, T299.

Residues G236 and S239 are respectively carrying the mutations G236A and S239D in the ADLE, ADE and DE schemes. Based on this analysis, the ADLE mutations might impact binding to FcγRIIa. Whereas the DSB positions are not found within the closest residues to FcγRIIa and should not impact the binding to FcγRIIa. T256D and T307Q mutations are far from the interaction surface, and thus should not be impact binding with FcγRIIa.

Contact Residues with FcRn

Based on structural analysis, the DSB positions should have no impact on FcRn binding surface. The positions of the DSB mutations are not part of the FcRn binding surface and are not in close proximity of the CH2-CH3 elbow where the binding surface is contained.

Impact on Knob-into-Hole (KIH) and RF Mutations of DSB

Based on structural analysis, the DSB should not have any impact on RF or KIH schemes, as they belong to different IgG domains of the Fc chains (CH2 domains for the DSB and CH3 domains for KIH and RF mutations).

Example 2: Construction and Characterization of Stabilized Variants

Monoclonal antibodies (mAbs) were formatted with enhanced effector-competent Fc backbones by introducing point mutations (Lazar, et al., PNAS, 103:4005-10 (2006)). Mutations introduced into the Fc domain were 1) an aspartic acid (D) at amino acid position 239 and a glutamic acid (E) at amino acid position 332 ("DE" variant); 2) an alanine (A) at amino acid position 236, an aspartic acid (D) at amino acid position 239, and a glutamic acid (E) at amino acid position 332 ("ADE" variant); or 3) an alanine (A) at amino acid position 236, an aspartic acid (D) at amino acid position 239, a leucine (L) at amino acid position 330, and a glutamic acid (E) at amino acid position 332 ("ADLE" variant) (see Smith, et al., PNAS, 109:6181-86 (2012)). Additional mutations were introduced to increase the half-life of the Fc-bearing polypeptides. An aspartic acid (D) was introduced at amino acid position 256 and a glutamine (Q) was introduced at amino acid position 307. Amino acid position numbering was based on EU numbering.

To produce DE, ADE, and ADLE variants with higher thermostability, cysteine substitutions were introduced to engineer intrachain disulfide bonds. Pairs of cysteines were substituted for the amino acids at the following positions: 1) a leucine (L) at amino acid position 242 and a lysine (K) at amino acid position 334; and 2) an arginine (R) at amino acid position 292 and a valine (V) at amino acid position 302. Amino acid position numbering was based on EU numbering.

Point mutations were introduced into the nucleic acid sequences encoding the human IgG1 Fc domain. these nucleic acid sequences were then fused to the coding sequence of the variable domain of mAb1 (an IgG1 antibody directed against a protein antigen present at the surface of immune cells) and cloned into mammalian expression plasmids containing a cytomegalovirus (CMV) enhancer/promoter and the SV40 polyA signal. The resulting plasmids were transfected into HEK293 cells according to the manufacturer's instructions.

```
Amino acid sequences of the human IgG1 heavy constant domain of the mAb1
variants mAb1
mAb1 (wt) (IgG1)
                                                                    (SEQ ID NO: 1)
ASTKGPSVFPLAPSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVLDSDGSFFLYSKLTVDKSRWQQGNVFSC

SVMHEALHNHYTQKSLSLSPG mAb1- DE (residues D239 and E332 are underlined)
                                                                    (SEQ ID NO: 2)
ASTKGPSVFPLAPSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPDVFLFPPKPKDTLMISRTPEVTCVVVDVSHEDP

EVKFNWYVDGVEVHNAKTKPREEQYNSTYRVVSVLTVLHQDWLNGKEYKCKVSNKALPAPEEKTISKAKGQPREPQV

YTLPPSRDELTKNQVSLTCLVKGFYPSDIAVEWESNGQPENNYKTTPPVLDSDGSFFLYSKLTVDKSRWQQGNVFSC

SVMHEALHNHYTQKSLSLSPG mAb1-DE-DQ (residues D239, E332, D256, Q307 are underlined)
                                                                    (SEQ ID NO: 3)
ASTKGPSVFPLAPSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPDVFLFPPKPKDTLMISRDPEVTCVVVDVSHEDP

EVKFNWYVDGVEVHNAKTKPREEQYNSTYRVVSVLQVLHQDWLNGKEYKCKVSNKALPAPEEKTISKAKGQPREPQV

YTLPPSRDELTKNQVSLTCLVKGFYPSDIAVEWESNGQPENNYKTTPPVLDSDGSFFLYSKLTVDKSRWQQGNVFSC

SVMHEALHNHYTQKSLSLSPG mAb1-DE-DQ-L242C-K334C (residues D239, E332, D256, Q307, C242 and C334 are
underlined)
                                                                    (SEQ ID NO: 4)
ASTKGPSVFPLAPSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPDVFCFPPKPKDTLMISRDPEVTCVVVDVSHEDP

EVKFNWYVDGVEVHNAKTKPREEQYNSTYRVVSVLQVLHQDWLNGKEYKCKVSNKALPAPEECTISKAKGQPREPQV

YTLPPSRDELTKNQVSLTCLVKGFYPSDIAVEWESNGQPENNYKTTPPVLDSDGSFFLYSKLTVDKSRWQQGNVFSC

SVMHEALHNHYTQKSLSLSPG
```

-continued mAb1-DE-DQ-R292C-V302C (residues D239, E332, D256, Q307, C292 and C302 are underlined)

(SEQ ID NO: 5)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGDVFLFPPKPKDTLMISRDPEVTCVVVDVSHEDP
EVKFNWYVDGVEVHNAKTKPCEEQYNSTYRCVSVLQVLHQDWLNGKEYKCKVSNKALPAPEEKTISKAKGQPREPQV
YTLPPSRDELTKNQVSLTCLVKGFYPSDIAVEWESNGQPENNYKTTPPVLDSDGSFFLYSKLTVDKSRWQQGNVFSC
SVMHEALHNHYTQKSLSLSPG mAb1-DE-R292C-V302C (residues D239, E332, C292 and C302 are underlined)

(SEQ ID NO: 6)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGDVFLFPPKPKDTLMISRTPEVTCVVVDVSHEDP
EVKFNWYVDGVEVHNAKTKPCEEQYNSTYRCVSVLTVLHQDWLNGKEYKCKVSNKALPAPEEKTISKAKGQPREPQV
YTLPPSRDELTKNQVSLTCLVKGFYPSDIAVEWESNGQPENNYKTTPPVLDSDGSFFLYSKLTVDKSRWQQGNVFSC
SVMHEALHNHYTQKSLSLSPG mAb1-DE-L242C-K334C (residues D239, E332, C242 and C334 are underlined)

(SEQ ID NO: 7)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGDVFCFPPKPKDTLMISRTPEVTCVVVDVSHEDP
EVKFNWYVDGVEVHNAKTKPREEQYNSTYRVVSVLTVLHQDWLNGKEYKCKVSNKALPAPEECTISKAKGQPREPQV
YTLPPSRDELTKNQVSLTCLVKGFYPSDIAVEWESNGQPENNYKTTPPVLDSDGSFFLYSKLTVDKSRWQQGNVFSC
SVMHEALHNHYTQKSLSLSPG mAb1-ADE (residues A236, D239, and E332 are underlined)

(SEQ ID NO: 8)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLAGPDVFLFPPKPKDTLMISRTPEVTCVVVDVSHEDP
EVKFNWYVDGVEVHNAKTKPREEQYNSTYRVVSVLTVLHQDWLNGKEYKCKVSNKALPAPEEKTISKAKGQPREPQV
YTLPPSRDELTKNQVSLTCLVKGFYPSDIAVEWESNGQPENNYKTTPPVLDSDGSFFLYSKLTVDKSRWQQGNVFSC
SVMHEALHNHYTQKSLSLSPG mAb1-ADE-DQ (residues A236, D239, E332, D256, and Q307 are underlined)

(SEQ ID NO: 9)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLAGPDVFLFPPKPKDTLMISRDPEVTCVVVDVSHEDP
EVKFNWYVDGVEVHNAKTKPREEQYNSTYRVVSVLQVLHQDWLNGKEYKCKVSNKALPAPEEKTISKAKGQPREPQV
YTLPPSRDELTKNQVSLTCLVKGFYPSDIAVEWESNGQPENNYKTTPPVLDSDGSFFLYSKLTVDKSRW mAb1-ADE-DQ-R292C-V302C (residues A236, D239, E332, D256, Q307, C292, and C302 are underlined)

(SEQ ID NO: 10)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLAGPDVFLFPPKPKDTLMISRDPEVTCVVVDVSHEDP
EVKFNWYVDGVEVHNAKTKPCEEQYNSTYRCVSVLQVLHQDWLNGKEYKCKVSNKALPAPEEKTISKAKGQPREPQV
YTLPPSRDELTKNQVSLTCLVKGFYPSDIAVEWESNGQPENNYKTTPPVLDSDGSFFLYSKLTVDKSRWQQGNVFSC
SVMHEALHNHYTQKSLSLSPG mAb1-ADE-DQ-L242C-K334C (residues A236, D239, E332, D256, Q307, C242, and C334 are underlined)

(SEQ ID NO: 11)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLAGPDVFCFPPKPKDTLMISRDPEVTCVVVDVSHEDP

EVKFNWYVDGVEVHNAKTKPREEQYNSTYRVVSVLQVLHQDWLNGKEYKCKVSNKALPAPEECTISKAKGQPREPQV
YTLPPSRDELTKNQVSLTCLVKGFYPSDIAVEWESNGQPENNYKTTPPVLDSDGSFFLYSKLTVDKSRW mAb1-ADE-R292C-V302C (residues A236, D239, E332, C292, and C302 are underlined)
(SEQ ID NO: 12)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLAGPDVFLFPPKPKDTLMISRTPEVTCVVVDVSHEDP
EVKFNWYVDGVEVHNAKTKPCEEQYNSTYRCVSVLTVLHQDWLNGKEYKCKVSNKALPAPEEKTISKAKGQPREPQV
YTLPPSRDELTKNQVSLTCLVKGFYPSDIAVEWESNGQPENNYKTTPPVLDSDGSFFLYSKLTVDKSRWQQGNVFSC
SVMHEALHNHYTQKSLSLSPG mAb1-ADE-L242C-K334C (residues A236, D239, E332, C242, and C334 are underlined)
(SEQ ID NO: 13)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLAGPDVFCFPPKPKDTLMISRTPEVTCVVVDVSHEDP
EVKFNWYVDGVEVHNAKTKPREEQYNSTYRVVSVLTVLHQDWLNGKEYKCKVSNKALPAPEECTISKAKGQPREPQV
YTLPPSRDELTKNQVSLTCLVKGFYPSDIAVEWESNGQPENNYKTTPPVLDSDGSFFLYSKLTVDKSRWQQGNVFSC
SVMHEALHNHYTQKSLSLSPG mAb1-ADLE (residues A236, D239, L330, E332 are underlined)
(SEQ ID NO: 14)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLAGPDVFLFPPKPKDTLMISRTPEVTCVVVDVSHEDP
EVKFNWYVDGVEVHNAKTKPREEQYNSTYRVVSVLTVLHQDWLNGKEYKCKVSNKALPLPE**EKTISKAKGQPREPQV
YTLPPSRDELTKNQVSLTCLVKGFYPSDIAVEWESNGQPENNYKTTPPVLDSDGSFFLYSKLTVDKSRWQQGNVFSC
SVMHEALHNHYTQKSLSLSPG mAb1-ADLE-DQ (residues A236, D239, L330, E332 D256, Q307 are underlined)
(SEQ ID NO: 15)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLAGPDVFLFPPKPKDTLMISRDPEVTCVVVDVSHEDP
EVKFNWYVDGVEVHNAKTKPREEQYNSTYRVVSVLQVLHQDWLNGKEYKCKVSNKALPLPE**EKTISKAKGQPREPQV
YTLPPSRDELTKNQVSLTCLVKGFYPSDIAVEWESNGQPENNYKTTPPVLDSDGSFFLYSKLTVDKSRWQQGNVFSC
SVMHEALHNHYTQKSLSLSPG mAb1-ADLE-DQ-L242C-K334C (residues A236, D239, L330, E332, D256, Q307, C242
and C334 are underlined)
(SEQ ID NO: 16)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLAGPDVFCFPPKPKDTLMISRDPEVTCVVVDVSHEDP
EVKFNWYVDGVEVHNAKTKPREEQYNSTYRVVSVLQVLHQDWLNGKEYKCKVSNKALPLPEEC**TISKAKGQPREPQV
YTLPPSRDELTKNQVSLTCLVKGFYPSDIAVEWESNGQPENNYKTTPPVLDSDGSFFLYSKLTVDKSRWQQGNVFSC
SVMHEALHNHYTQKSLSLSPG mAb1-ADLE-DQ-R292C-V302C (residues A236, D239, L330, E332, D256, Q307, C292
and C302 are underlined)
(SEQ ID NO: 17)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLAGPDVFLFPPKPKDTLMISRDPEVTCVVVDVSHEDP
EVKFNWYVDGVEVHNAKTKPCEEQYNSTYRCVSVLQVLHQDWLNGKEYKCKVSNKALPLPE**EKTISKAKGQPREPQV
YTLPPSRDELTKNQVSLTCLVKGFYPSDIAVEWESNGQPENNYKTTPPVLDSDGSFFLYSKLTVDKSRWQQGNVFSC
SVMHEALHNHYTQKSLSLSPG -continued mAb1-ADLE-R292C-V302C (residues A236, D239, L330, E332, C292 and C302 are underlined)

(SEQ ID NO: 18)
ASTKGPSVFPLAPSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELL<u>A</u>GP<u>D</u>VFLFPPKPKDTLMISRTPEVTCVVVDVSHEDP

EVKFNWYVDGVEVHNAKTKP<u>C</u>EEQYNSTYR<u>C</u>VSVLTVLHQDWLNGKEYKCKVSNKALP<u>L</u>P<u>E</u>EKTISKAKGQPREPQV

YTLPPSRDELTKNQVSLTCLVKGFYPSDIAVEWESNGQPENNYKTTPPVLDSDGSFFLYSKLTVDKSRWQQGNVFSC

SVMHEALHNHYTQKSLSLSPG mAb1-ADLE-L242C-K334C (residues A236, D239, L330, E332, C242 and C334 are underlined)

(SEQ ID NO: 19)
ASTKGPSVFPLAPSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELL<u>A</u>GP<u>D</u>VF<u>C</u>FPPKPKDTLMISRTPEVTCVVVDVSHEDP

EVKFNWYVDGVEVHNAKTKPREEQYNSTYRVVSVLTVLHQDWLNGKEYKCKVSNKALP<u>L</u>P<u>E</u>E<u>C</u>TISKAKGQPREPQV

YTLPPSRDELTKNQVSLTCLVKGFYPSDIAVEWESNGQPENNYKTTPPVLDSDGSFFLYSKLTVDKSRWQQGNVFSC

SVMHEALHNHYTQKSLSLSPG mAb1 variants were produced at 1.5 liter scale and purified by a two-step process including Protein A affinity chromatography (HI Screen MAbSelect Sure protein A, Cytiva) and size-exclusion chromatography (HI Load 26/600 superdex 200 μg, Cytiva) equilibrated with PBS. The pool of fractions was concentrated by using Sartorius Vivaspin 10 KDa up to 10 mg/mL. The samples were then filter sterilized and stored at 4° C. until use. Batches were analyzed by UV, LabChip GXII touch HT protein in reduced and non-reduced conditions, SEC-HPLC, and LC-MS for quantification, purity, and identity. Engineered disulfide bonds were analyzed via extracted ion chromatography (XIC) comprising LC_MS (Q-Tof) after enzymatic digestion with Lys-C, Trypsin, or Trypsin+Glu-C serine protease mix for peptide mapping.

Results

Figure 6:
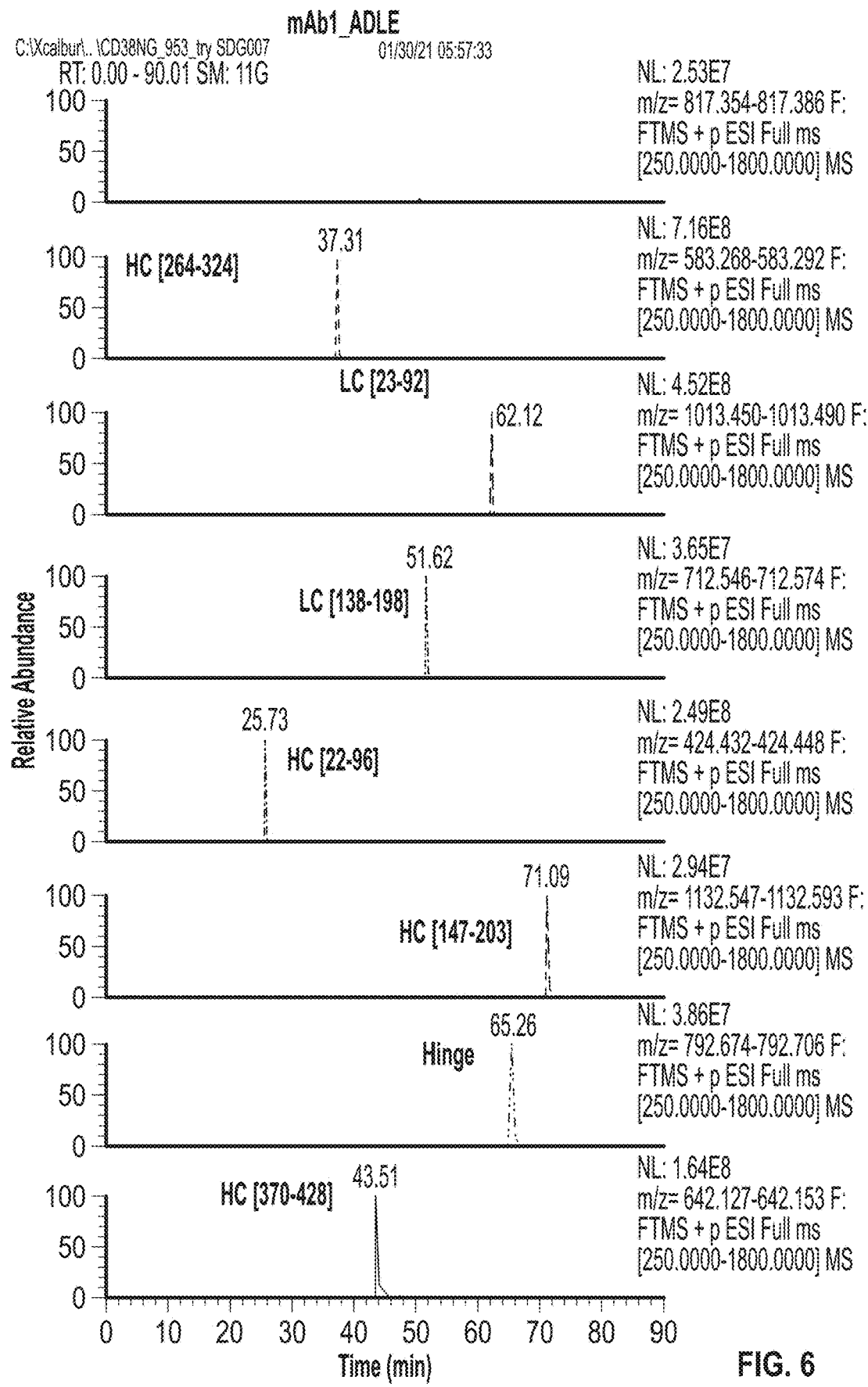
FIG. 6 depicts extracted ion chromatogram (XIC) peptide quantification profiles of disulfide bonds with mAb1 ADLE and DSB mutants. For ADLE, eight disulfide bridges were detected, except for 218LC-223HC, which eluted in the dead volume. For ADLE_DQ_R292C_V302C, nine disulfide bridges were detected, except for 218LC-223HC, which eluted in dead the volume. For ADLE_DQ_L242C_K334C, eight disulfide bridges were detected, except for 218LC-223HC, which eluted in the dead volume, and with one common peptide (the same for the mutation and the hinge).
Figure 6:
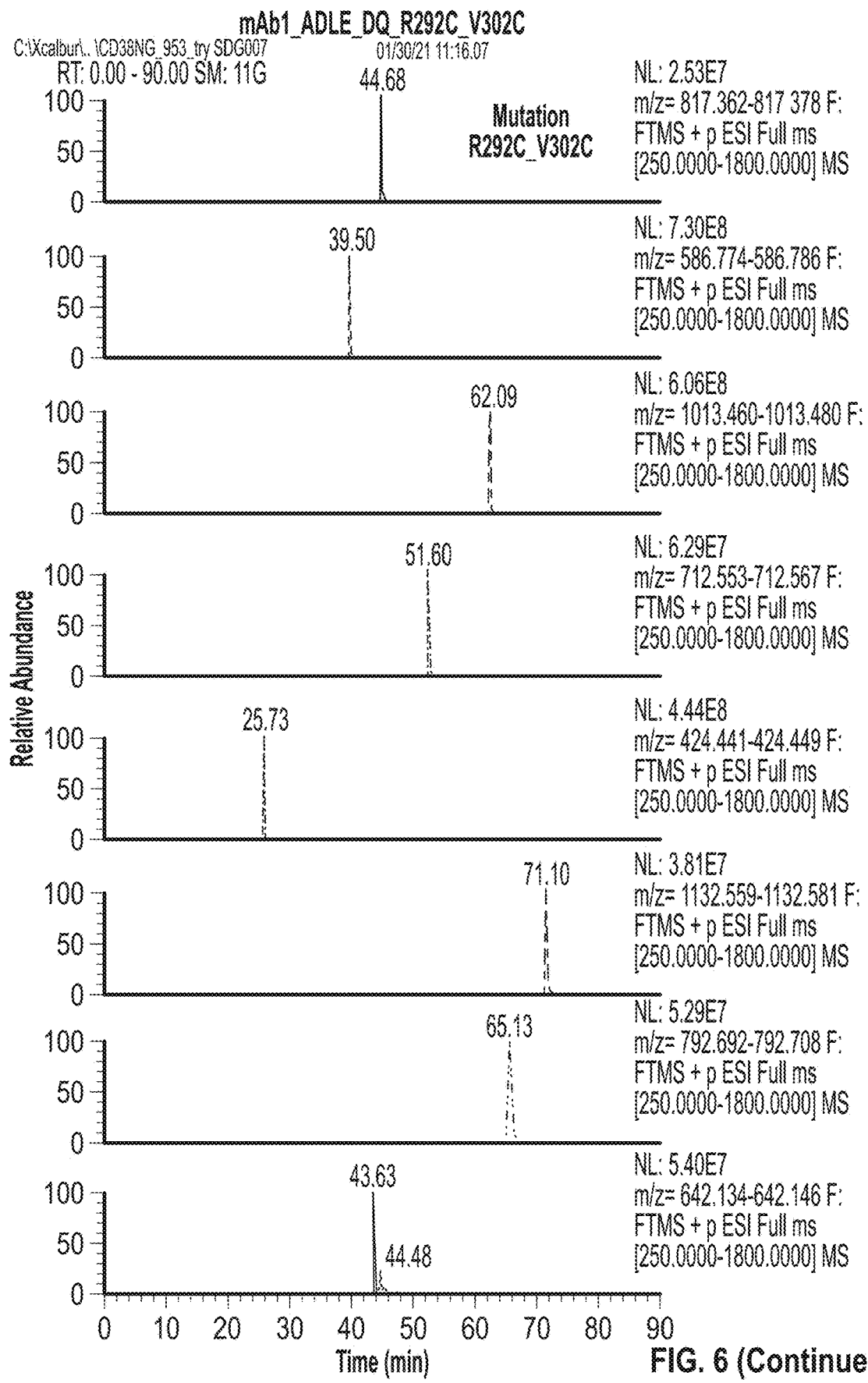
Figure 6:
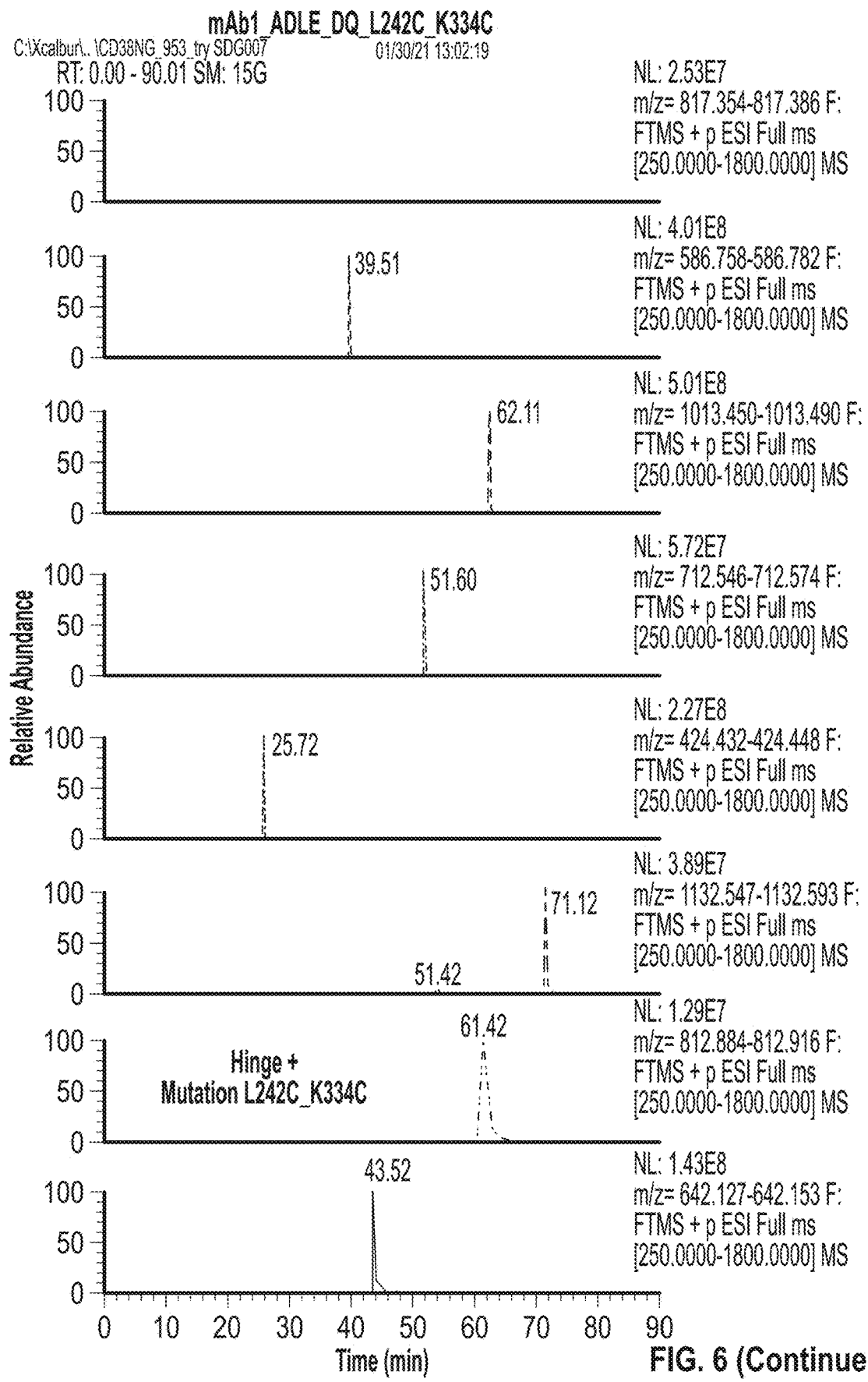
Figure 7A:
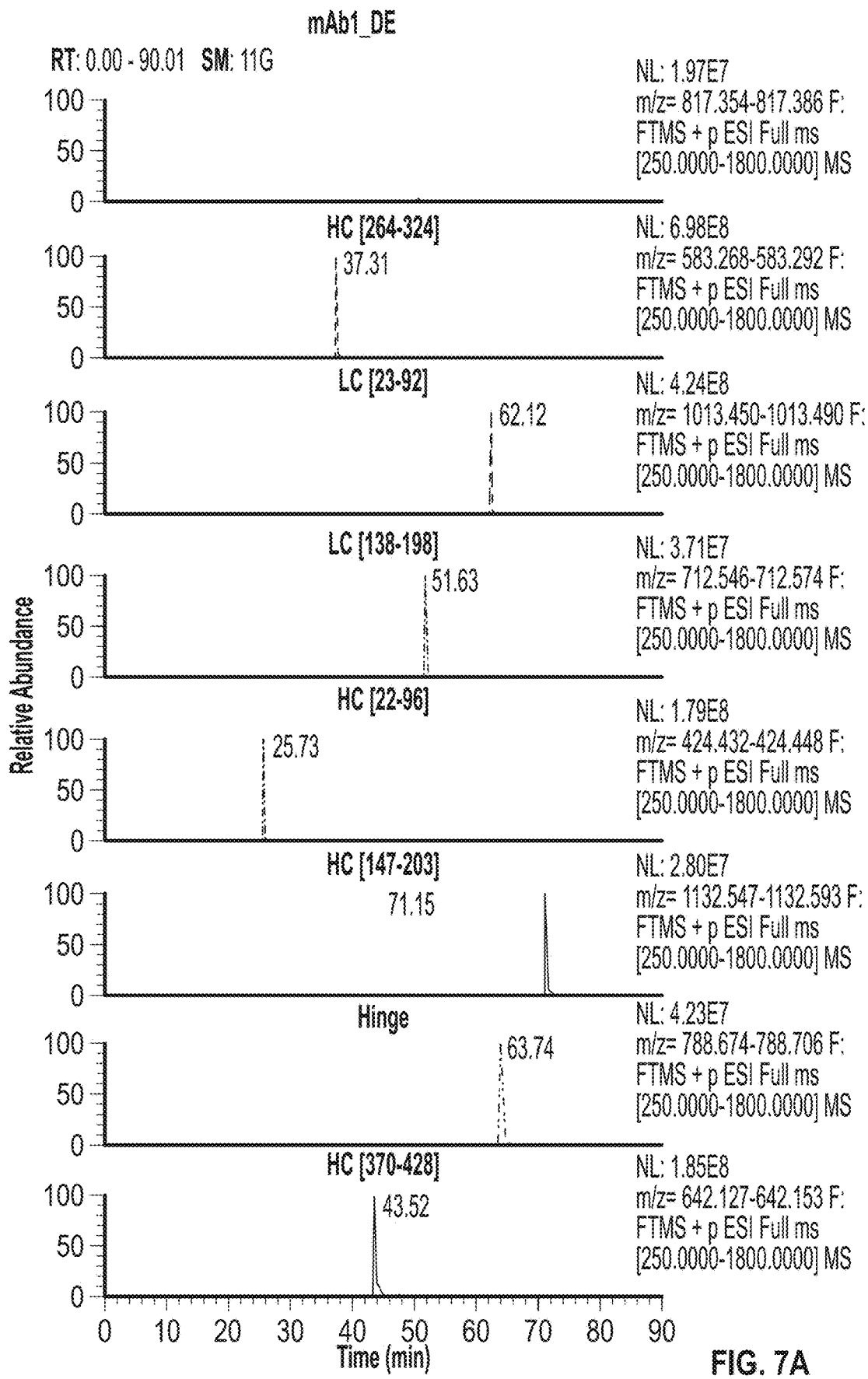
FIG. 7A-FIG. 7B depict XIC peptide quantification profiles of disulfide bonds with mAb1 DE and DSB mutants (FIG. 7A) and mAb1 ADE and DSB mutants (FIG. 7B). For DE, eight disulfide bridges were detected, except for 218LC-223HC, which eluted in the dead volume. For DE_DQ_R292C_V302C, nine disulfide bridges were detected, except for 218LC-223HC, which eluted in dead the volume. For DE_DQ_L242C_K334C, nine disulfide bridges were detected, except for 218LC-223HC, which eluted in the dead volume, and with one common peptide (the same for the mutation and the hinge).
Figure 7A:
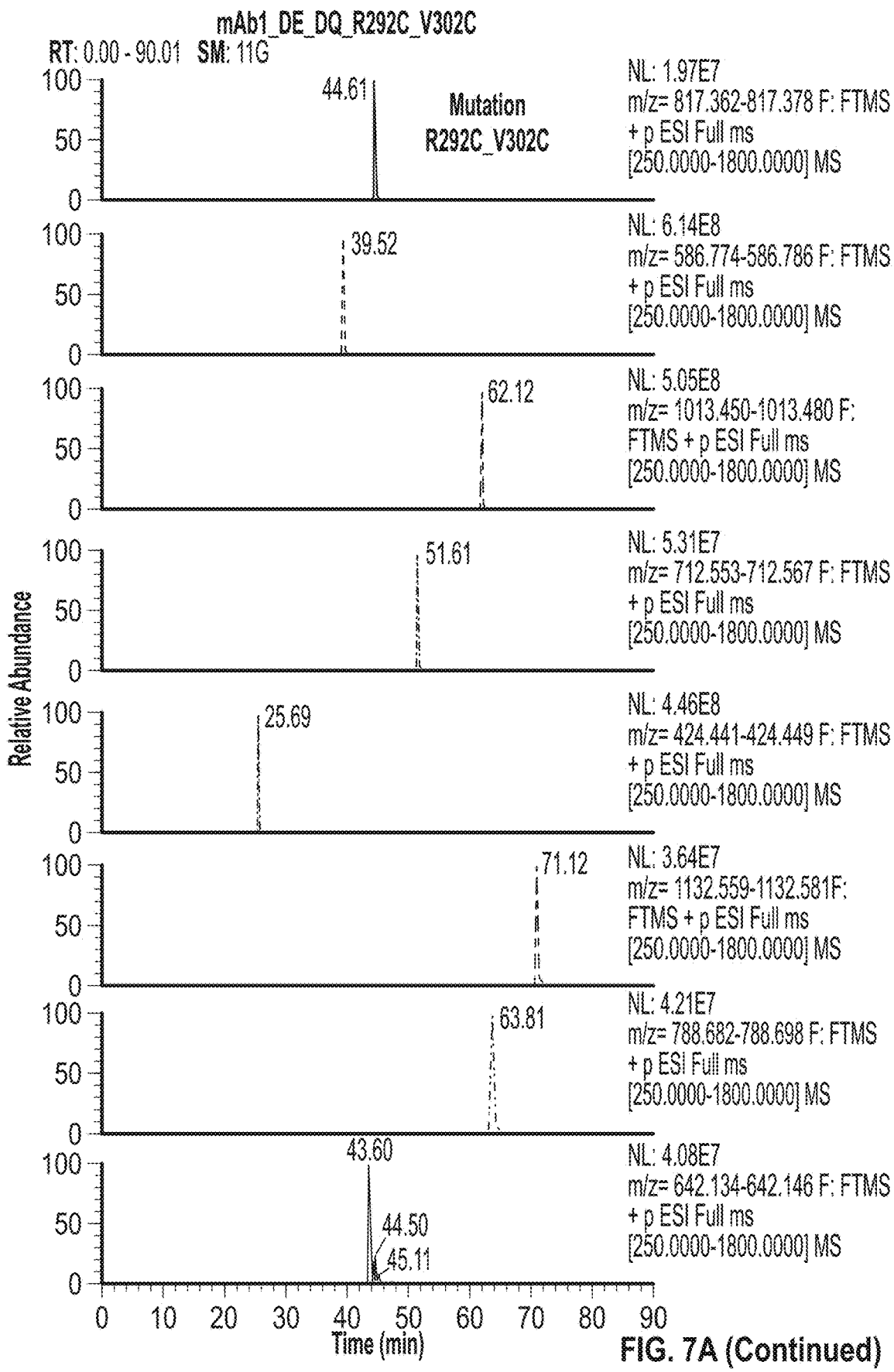
Figure 7A:
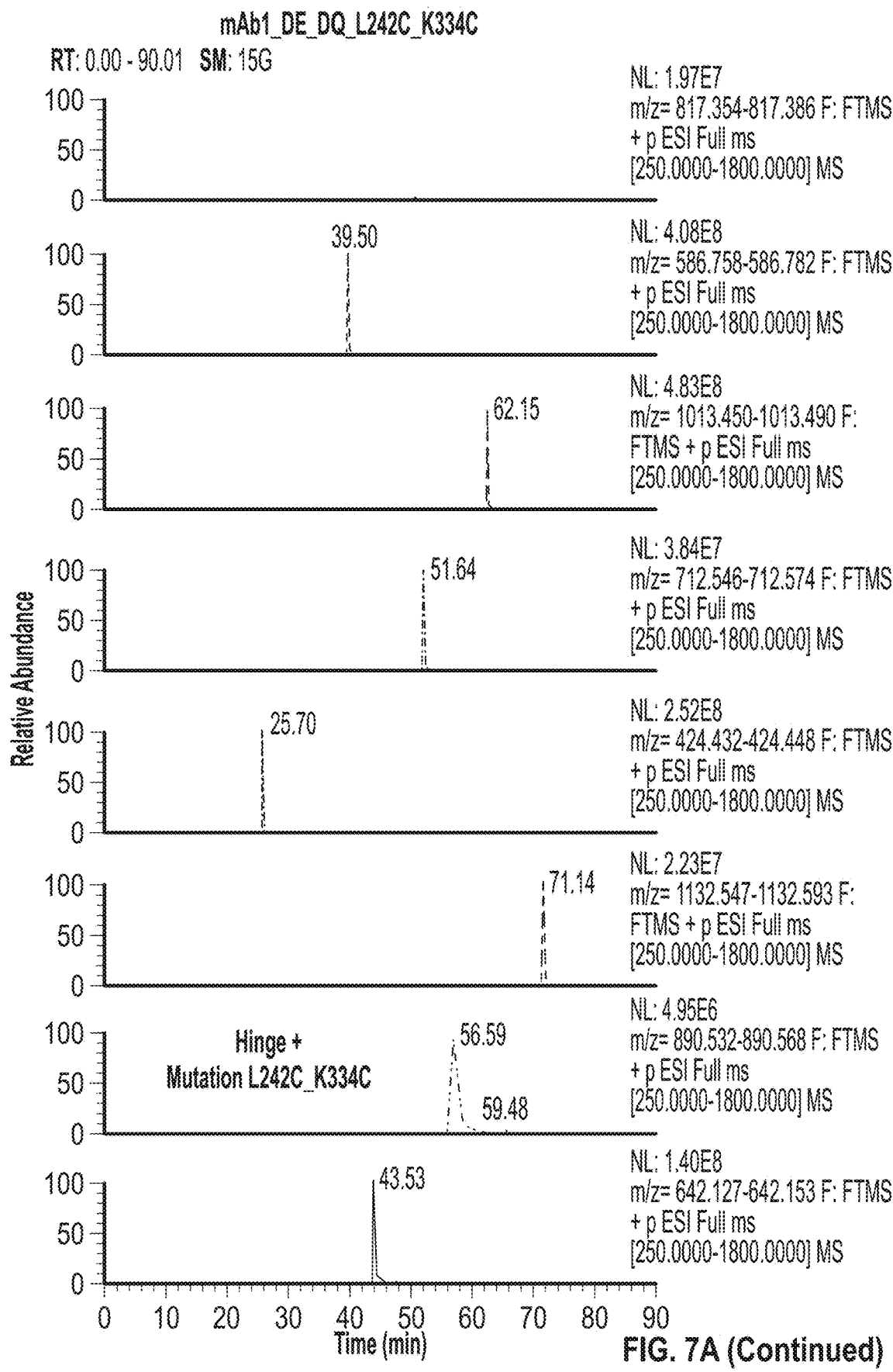
Figure 7B:
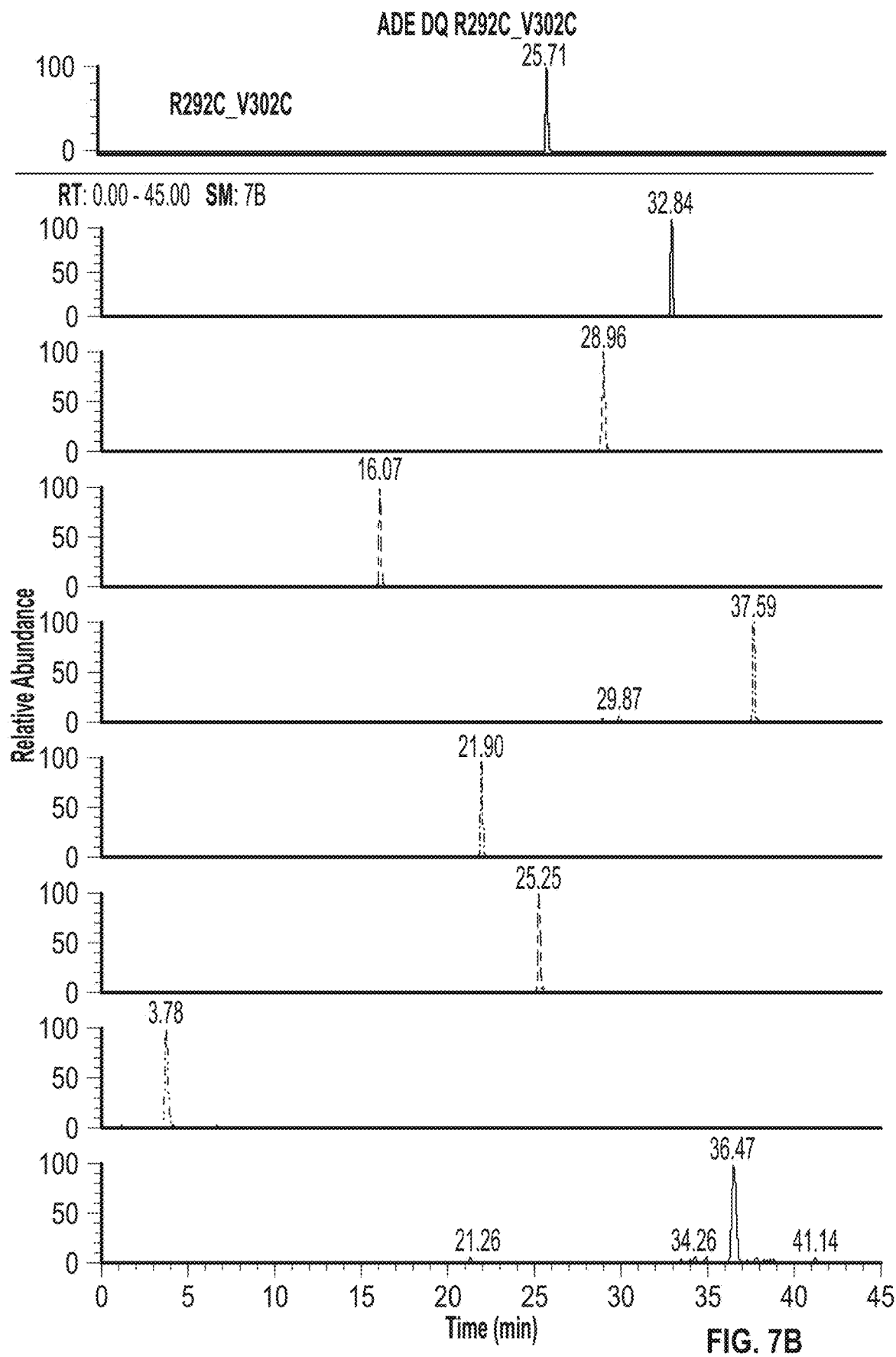
Figure 7B:
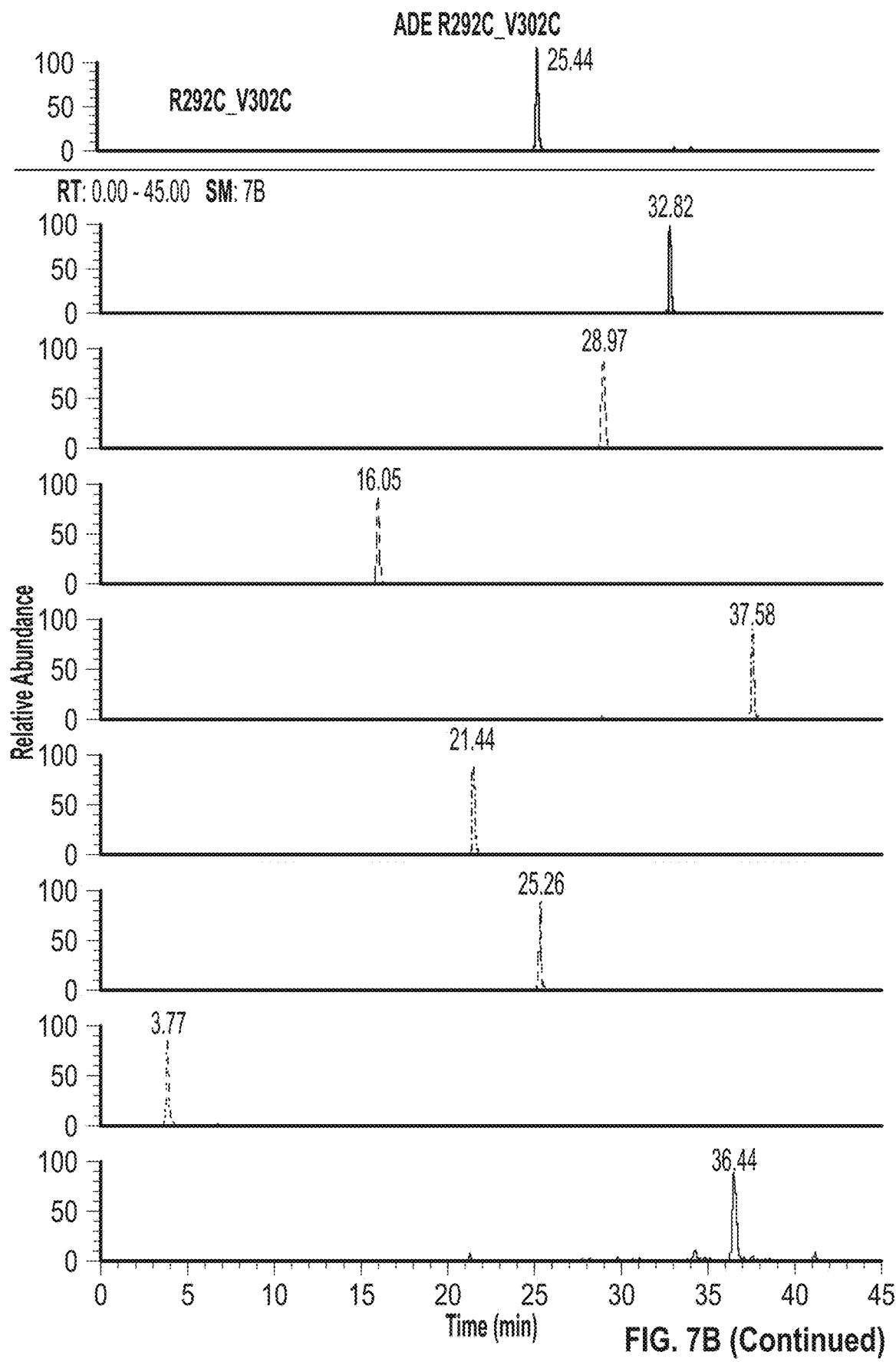
Figure 7B:
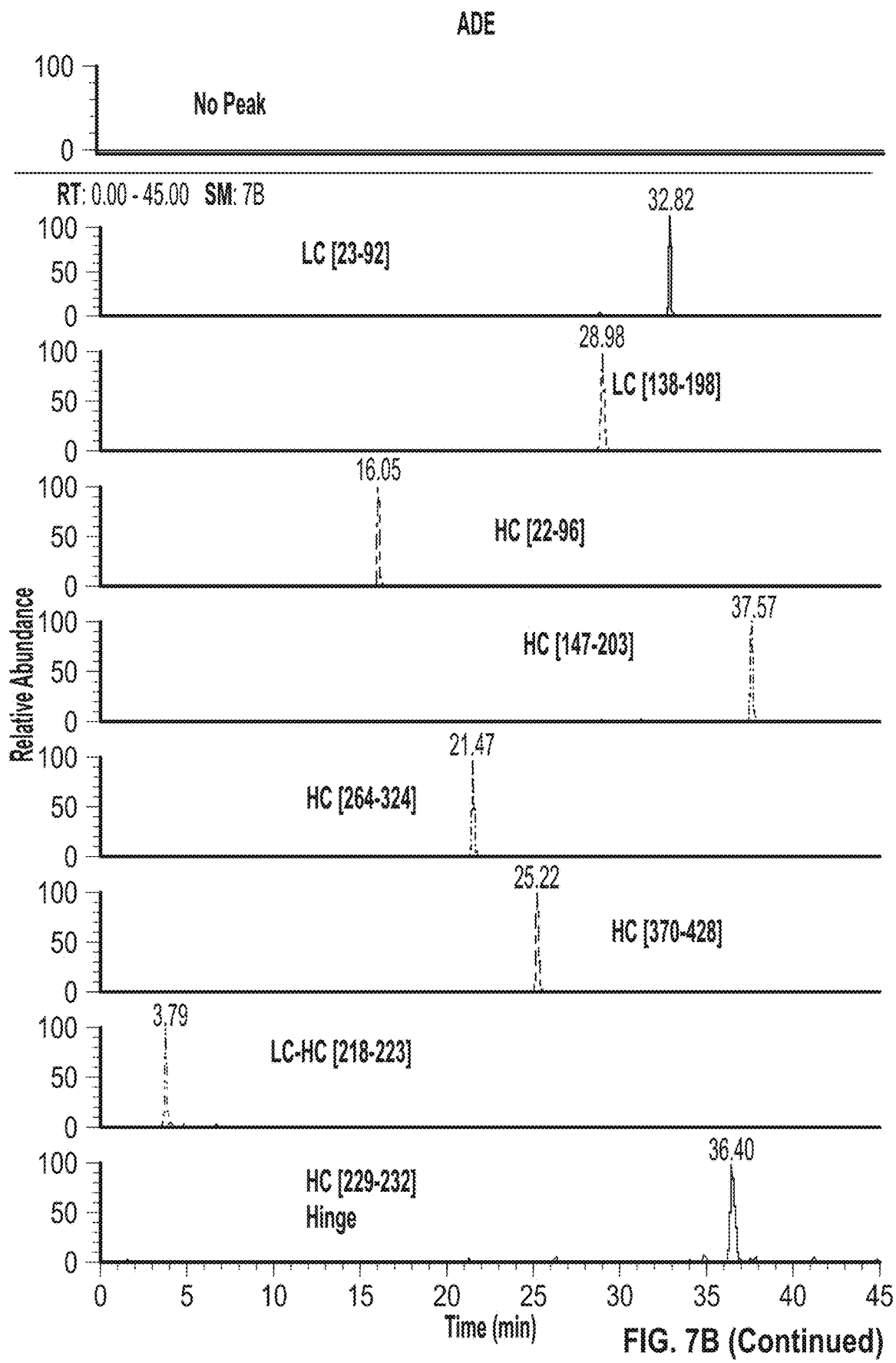

Batches were produced and characterized with the expected profiles. Sample yields of the A287C+L306C constructs were very low compared to any other constructions. Disulfide bonds were determined by XIC and the additional disulfide bond was present as anticipated as illustrated by FIG. 6 (XIC profile of disulfide bonds with mAb1 ADLE DQ & DSB mutants) and FIG. 7A and FIG. 7B (XIC profile of disulfide bonds with mAb1_DE & DSB mutants and mAb1_ADE & DSB mutants).

To test the thermostability of the mAbs with Fc variants, the mAbs were diluted in PBS at 10 mg/mL. Thermostability was determined by nano-format of Differential Scanning Fluorimetry (nanoDSF) with a Prometheus NT48 using standard capillaries and a linear gradient of temperature was applied from 20° to 95° C. at a heating rate of 1° C. per minute.

TABLE 1

Antibody Production

| Batch | Description | Sample yield (mg/L) Serie 1 at 1.5-L scale | Sample yield (mg/L) Serie 2 at 0.6-L scale |
|---|---|---|---|
| VA2-21-262-1 | MAb1-ADE-DQ-R292C_V302C | | 87 |
| VA2-21-261-1 | MAb1-ADE-DQ-L242C_K334C | | 68 |
| VA2-21-266-1 | MAb1-ADE-DQ | | 36 |
| VA2-21-260-1 | MAb1-ADE-R292C_V302C | | 76 |
| VA2-21-259-1 | MAb1-ADE-L242C_K334C | | 66 |
| VA2-21-264-1 | MAb1-ADE-A287C_L306C | | 6 |
| VA2-19-943-1 | MAb1-ADE | 55 | |
| VA2-20-953-1 | MAb1-ADLE-DQ-R292C_V302C | 47 | |
| VA2-20-954-1 | MAb1-ADLE-DQ-L242C_K334C | 28 | |
| VA2-20-952-1 | MAb1-ADLE-DQ | 27 | |
| VA2-21-268-1 | MAb1-ADLE-R292C_V302C | | 88 |
| VA2-21-267-1 | MAb1-ADLE-L242C_K334C | | 38 |
| VA2-21-265-1 | MAb1-ADLE-A287C_L306C | | 4 |
| VA2-20-949-1 | MAb1-ADLE | 40 | |
| VA2-20-956-1 | MAb1-DE-DQ-R292C_V302C | 46 | |
| VA2-20-957-1 | MAb1-DE-DQ-L242C_K334C | 36 | |
| VA2-20-955-1 | MAb1-DE-DQ | 37 | |
| VA2-21-270-1 | MAb1-DE-R292C_V302C | | 83 |
| VA2-21-269-1 | MAb1-DE-L242C_K334C | | 61 |
| VA2-21-263-1 | MAb1-DE-A287C_L306C | | 9 |
| VA2-20-951-1 | MAb1-DE | 59 | |
| VA2-20-950-1 | Mab1-WT | 40 | |

NanoDSF uses the change in intrinsic fluorescence of proteins to monitor protein unfolding with increasing temperature. The protein solution is excited using a 266 nm wavelength light source and the fluorescence emission of the tyrosine and tryptophan residues at 330 nm and 350 nm. The emission maxima and the intensity of tyrosine and tryptophan residues are highly dependent on their immediate environment and can change as the protein unfolds during thermal denaturation. Monitoring the change in ratio of fluorescence intensities at 330 nm and 350 nm as a function of temperature yields a sigmoid shaped curve that represents the unfolding transition of the protein. The midpoint of the sigmoid curve represents the melting temperature (Tm). The detectable temperature at which a protein begins to unfold is the Tonset. There are three inflexion points (IP) two correspond to the CH2 and CH3 of the Fc domain and the third one corresponds to Fab domain. Tagg is the temperature at which proteins exhibit a tendency to aggregate.

Figure 8:
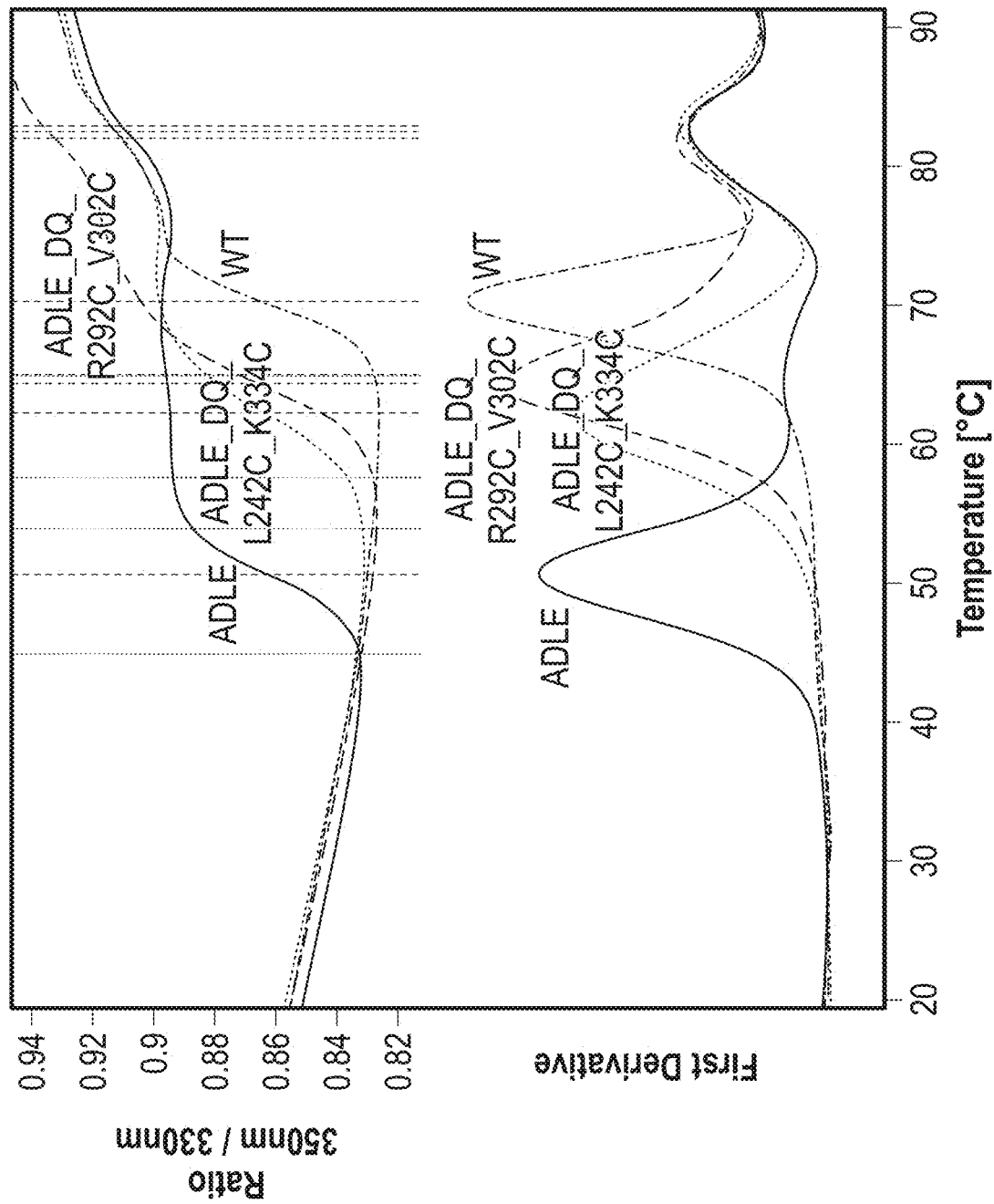
FIG. 8 depicts the thermostability effects of disulfide stabilization for mAb1 ADLE variants as determined by nano differential scanning fluorimetry (nanoDSF).
Figure 9A:
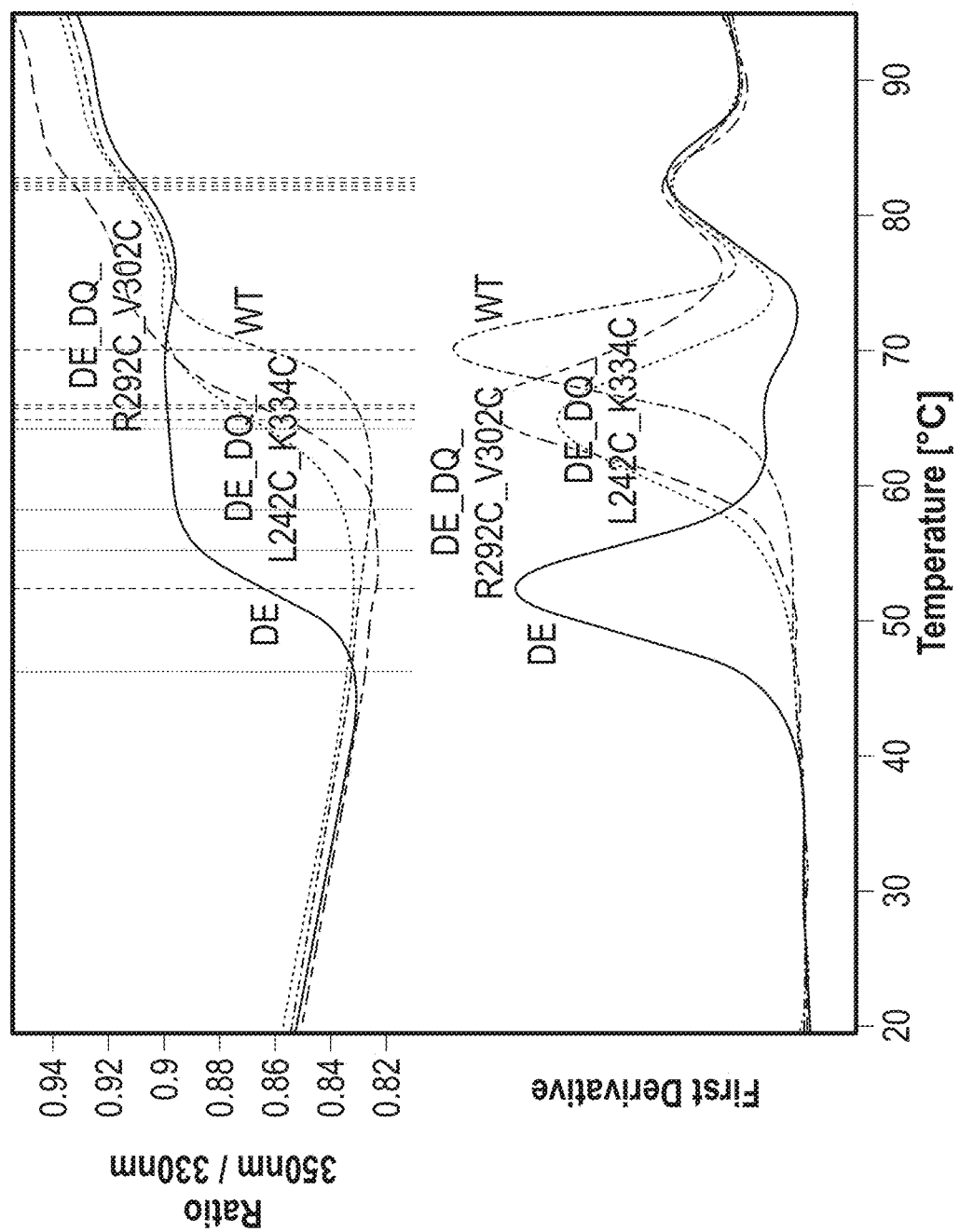
FIG. 9A-FIG. 9B depicts the thermostability effects of disulfide stabilization for mAb1 DE variants (FIG. 9A) and ADE variants (FIG. 9B) as determined by nanoDSF.
Figure 9B:
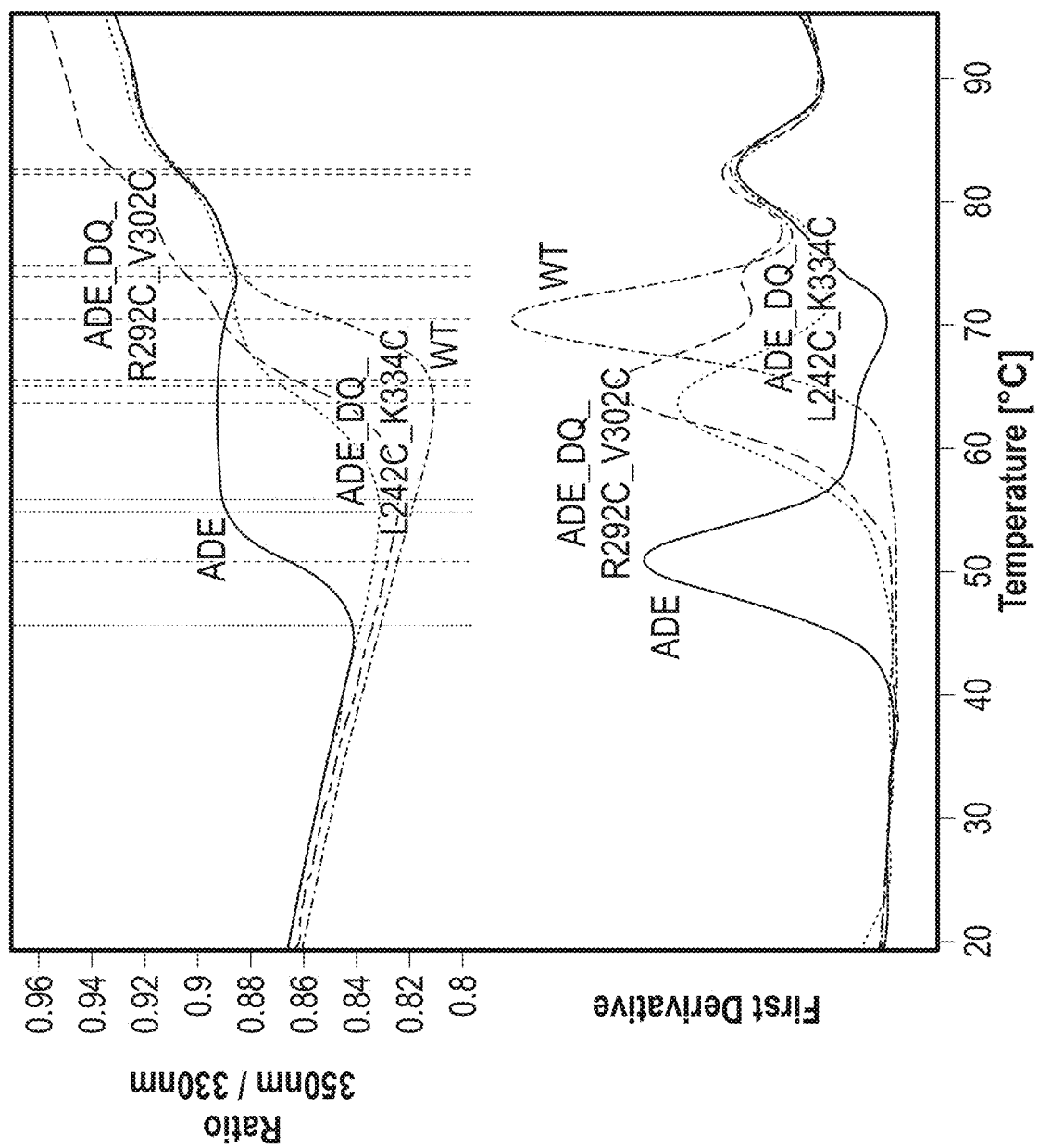

The results of the thermostability studies of the ADE, DE and ADLE variants can be found in Table 2 and FIG. 8 and FIG. 9A-FIG. 9B. NanoDSF uses the change in the intrinsic fluorescence of proteins to monitor protein unfolding with increasing temperature. Monitoring the change in the ratio of fluorescence intensities at 330 nm and 350 nm as a function of temperature yields a sigmoid curve that represents the unfolding transition of the protein. The midpoint of the sigmoid curve represents the melting temperature (Tm). The detectable temperature at which a protein begins to unfold is the Tonset. Three inflection points (IP) are recorded: Two correspond to the CH2 and CH3 of the Fc domain, and the third one corresponds to the Fab domain. Tagg is the temperature at which the proteins begin to aggregate.

All Fabs were very stable with a Tm between 82° C. and 83° C.

The Tonset for the WT IgG1 (mAb1) was 65° C., and below 50° C. for mAb1 ADLE, ADE and DE with or without the DQ mutation. On the other hand, when R292C_V302C or L242C_K334C DSB were introduced, the Tonset was well above 50° C. like the wild type IgG1 molecule. The IP Fc is above 60° C. for molecules containing R292C_V302C or L242C_K334C DSB like the wild type IgG1. The introduction of R292C_V302C or L242C_K334C DSB restored the thermostability in the context of the ADCC-enhanced Fc ADLE, ADE or DE with or without the DQ enhanced half-life mutation.

The A287C_L306C DSB did not restore thermostability in the ADCC-enhanced Fc ADLE, ADE or DE without the DQ enhanced half-life mutation.

mAb2

The following further Fc variants were made based on mAb2 (an IgG1 monoclonal antibody directed against a G-coupled protein receptor (GCPR) at the surface of immune cells): mAb2 (wt) (wild-type IgG1 Fc), mAb2-DE (corresponding to mAb2 with the additional substitutions S239D and I332E), mAb2-DE-R292C/V302C (corresponding to mAb2-DE with the additional substitutions R292C and V302C) and mAb2-R292C/V302C (corresponding to mAb2 wt with the substitutions R292C and V302C).

Thermostability of mAb2 wt, mAb2-DE, mAb2-DE-R292C/V302C and mAb2-R292C/V302C was tested with the same method as described above for mAb1 and the results are provided in Table 3.

TABLE 2

Thermostability of mAb1 with a wild-type IgG1 or with enhanced Fc domains mAb1

| ADE+/− | IgG1_ADE | IgG1_ADE | IgG1_ADE | IgG1_ADE | IgG1_ADE | IgG1_ADE | IgG1_ADE | IgG1 |
|---|---|---|---|---|---|---|---|---|
| DQ+/− | DQ | DQ | DQ | — | — | — | — | — |
| DSB | R292C_V302C | L242C_K334C | — | R292C_V302C | L242C_K334C | A287C_L306C | — | — |
| Batch | VA2-21-262-1 | VA2-21-261-1 | VA221-266-1 | VA2-21-260-1 | VA2-21-259-1 | VA2-21-264-1 | VA2-19-943-1 | VA2-20-950-1 |
| Tonset ° C. | 56 | 55 | 44 | 61 | 58 | 42 | 46 | 65 |
| IP Fc | 65 (74) | 64 (75) | 50 (73) | 69 | 66(75) | 51 (73) | 51 (66) | 71 |
| IP Fab | 82 | 83 | 82 | 83 | 83 | 82 | 83 | 82 |
| Tagg | 73 | 72 | 75 | 73 | 73 | 74 | 72 | 73 | mAb1

| ADLE+/− | IgG1_ADLE | IgG1_ADLE | IgG1_ADLE | IgG1_ADLE | IgG1_ADLE | IgG1_ADLE | IgG1_ADLE | IgG1 |
|---|---|---|---|---|---|---|---|---|
| DQ+/− | DQ | DQ | DQ | — | — | — | — | — |
| DSB | R292C_V302C | L242C_K334C | — | R292C_V302C | L242C_K334C | A287C_L306C | — | — |
| Batch | VA2-20-954-1 | VA2-20-953-1 | VA2-20-952-1 | VA2-21-268-1 | VA2-21-267-1 | VA2-21-265-1 | VA2-20-949-1 | VA2-20-950-1 |
| Tonset ° C. | 58 | 54 | 39 | 60 | 57 | 41 | 45 | 65 |
| IP Fc | 64 | 62 | 47 (66) | 67 | 64 (75) | 50 (73) | 50 (65) | 71 |
| IP Fab | 82 | 83 | 82 | 82 | 83 | 82 | 83 | 82 |
| Tagg | 74 | 73 | 74 | 73 | 72 | 75 | 72 | 73 | mAb1

| DE+/− | IgG1_DE | IgG1_DE | IgG1_DE | IgG1_DE | IgG1_DE | IgG1_DE | IgG1_DE | IgG1 |
|---|---|---|---|---|---|---|---|---|
| DQ+/− | DQ | DQ | DQ | — | — | — | — | — |
| DSB | R292C_V302C | L242C_K334C | — | R292C_V302C | L242C_K334C | A287C_L306C | — | — |
| Batch | VA2-20-956-1 | VA2-20-957-1 | VA2-20-955-1 | VA2-21-270-1 | VA2-21-269-1 | VA2-21-263-1 | VA2-20-951-1 | VA2-20-950-1 |
| Tonset ° C. | 59 | 55 | 42 | 58 | 59 | 41 | 47 | 65 |
| IP Fc | 66 | 65 | 49 (65) | 69 | 67 | 52 (74) | 53 (66) | 71 |
| IP Fab | 82 | 83 | 82 | 82 | 83 | 82 | 82 | 82 |
| Tagg | 73 | 73 | 73 | 73 | 73 | 75 | 74 | 73 |

TABLE 3

Thermostability of mAb2 with a wild-type IgG1 or with enhanced Fc domain, with or without disulfide bond

| Clone | TM1 (° C.) |
| --- | --- |
| mAb2-R292C/V302C | 73.0 |
| mAb2 wt (ctrl) | 71.9 |
| mAb2-DE-R292C/V302C | 67.9 |
| mAb2-DE | 51.0 |

These results show that the DE mutation in mAb2 has led to a lower thermal stability (Tm of 71.9° C. for mAb2 wt vs. Tm of 51.0° C. for mAb2-DE) and that the introduction of the disulfide bound restored an thermal stability (Tm 67.9° C.).

mAb3

The following further Fc variants were made based on mAb3 (an IgG1 monoclonal bivalent bispecific CODV-OL1 antibody directed against a protein antigen present at the surface of immune cells and a protein antigen present at the surface of cancer cells): mAb3 (wt) (wild-type IgG1 Fc), mAb3-DE (corresponding to mAb3 with the additional substitutions S239D and I332E), mAb3-DE-R292C/V302C (corresponding to mAb3-DE with the additional substitutions R292C and V302C), mAb3-ADE (corresponding to mAb3 with the additional substitutions G236A, S239D, and I332E), and mAb3-ADE-R292C/V302C (corresponding to mAb3-ADE with the additional substitutions R292C and V302C).

The mAb3 antibodies were produced as follows:

The expression plasmids encoding the different chains of the corresponding constructs were propagated in *E. coli* DH5a. Plasmids used for transfection were prepared from *E. coli* with EndoFree Plasmid Mega kits (Qiagen). HEK 293-FS cells growing in F17 serum free suspension culture (Invitrogen) were transfected with indicated plasmids using polyethyleneimine transfection reagent. After 6 days of cultivation at 37° C. with 8% CO2 cells were removed by centrifugation and the supernatant was passed over a 0.22 µm filter to remove particles. The Proteins were captured on MabSelect SuRe (Cytiva) and eluted with 0.1 M Citrate buffer pH 3.0 and neutralized with 1 M Tris pH 9. After polishing the proteins by size exclusion chromatography (SEC) using a Superdex200 26/60 (Cytiva) and 0.22 µm filtration and UV280 concentration determination the proteins were used for further characterization. The yields are reported below in Table 4.

TABLE 4

Yield of mAb3 with a wild-type IgG1 or with enhanced Fc domain, with or without disulfide bond

| Clone | Sample Yield (mg/L) |
| --- | --- |
| mAb3-WT | >20 |
| mAb3-DE | <10 |
| mAb3-ADE | <10 |
| mAb3-DE-R292C/V302C | >20 |
| mAb3-ADE-R292C/V302C | >20 |

The antibody with a normal IgG1 Fc backbone demonstrated a sample yield of greater than 20 mg/L while the antibodies with ADE or DE mutations in the Fc backbone show a reduction below 10 mg/L in the sample yields. The antibodies with an IgG1 Fc with ADE or DE mutations and with the disulfide-bond demonstrated a sample yield similar to WT and an increase in the sample yield by a factor 4 to 6-fold, with mAb3-DE-R292C/V302C and mAb3-ADE-R292C/V302C showing a sample yield of greater than 20 mg/L.

Thermostability of the mAb3 antibodies were tested with the same method as described above for mAb1 and the results are provided in Table 5.

TABLE 5

Thermostability of mAb3 with a wild-type IgG1 or with enhanced Fc domain, with or without disulfide bond

| Clone | Tonset | Tm1 |
| --- | --- | --- |
| mAb3-WT | 58.5 | 64.3 |
| mAb3-DE | 40.4 | 47.5 |
| mAb3-ADE | 41.2 | 46.8 |
| mAb3-DE-R292C/V302C | 57.8 | 65.9 |
| mAb3-ADE-R292C/V302C | 57.5 | 65.9 | mAb3 with a normal IgG1 Fc backbone was stable with a Tm1 of 64.3° C. and a Tonset of 58.5° C. The mAb3 molecules with ADE or DE mutations in the IgG1 Fc demonstrate Tm1 and Tonset below 50° C. Molecules with an IgG1 Fc with ADE or DE mutations and with the disulfide-bond show an increase in thermostability. The mAb3-DE-DSB molecule shows a Tm1 of 65.9° C. and Tonset of 57.8° C. and the mAb3-ADE-DSB shows a Tm1 of 65.9° C. and a Tonset of 57.5° C.

Chemical Integrity of Disulfide-Bond R292C/V302C within the mAb3

Engineering of disulfide bonds (DSB) on the Fc CH2 domain increases stability. To ensure that the engineered DSB, R292C_V302C, and the ADE mutations (G236A/S239D/I332E) within mAb3 do not aberrantly influence DSB reduction behavior the rate of reduction was measured by DTT and subsequent tryptic peptide mapping.

Material and Methods

Reduction Sensitivity Assay

A serial dilution of DTT in PBS-E was performed (final DTT concentrations in assay: 20, 10, 5, 2, 1, 0.5, 0.2 and 0.1 mM). The protein batches FF-20-819-1, FF-20-821-1 and FF-21-170-5 were dialyzed into PBS-E buffer using spin-desalting columns to ensure pH 7.2 was obtained during reduction. The protein samples were normalized to 1.5 mg/mL in PBS-E. Two parts of normalized sample were added to one part of each DTT dilution into a PCR plate and were mixed after addition. This step was performed from lowest to highest concentration DTT concentration within one minute. Reduction was performed by incubation at 25° C. for 10 minutes on a Thermostat C Thermoblock. The reaction was quenched by the addition of 3 parts of NEM stock solution to all wells. To ensure assay consistency the NEM addition was conducted from lowest to highest DTT concentration within one minute and mixed after addition. The prepared plate was stored at room temperature until measurement by capillary gel electrophoresis (cGE) and mass spectrometry (peptide mapping).

Table 6A and Table 6B below contain the reagent and material list for the reduction sensitivity assay and capillary gel electrophoresis, respectively.

TABLE 6A

Reagent and material list for the reduction sensitivity assay

| Reagent/material | Manufacturer | Catalog# | Stock conc. |
|---|---|---|---|
| PBS Buffer pH 7.2 | Gibco/Thermo-Fisher | 20012043 | 1x |
| Dithiothreitol (DTT) | Pierce/Thermo-Fisher | A39255 | solid, resolved in PBS-E to 100 mM |
| N-ethylmaleimide (NEM) | Pierce/Thermo-Fisher | 23030 | solid, resolved in PBS-E to 200 mM |
| Invitrogen EDTA, pH 8.0 | Thermo-Fisher | AM9260G | 0.5M |
| Hard-shell 96 well plate | Bio-Rad | HSP9601 | / |
| Spin Desalting Columns, 7K MWCO | ZEBA | 89883 | / |

| Instrument | Manufacturer | Catalog # |
|---|---|---|
| Thermostat C Thermoblock | Eppendorf | 5383000027 |

| Assay buffer | Composition |
|---|---|
| PBS-E | Gibco 1X PBS Buffer pH 7.2 + 1 mM EDTA |

TABLE 6B

Reagent and material list for capillary gel electrophoresis (cGE)

| Reagent/material | Manufacturer | | |
|---|---|---|---|
| Water MS grade | Thermo | #51140 | / |
| Iodoacetamide (IAM) | Thermo-Fisher | #A39271 | solid, resolved in water to 250 mM |
| Hard-shell 96 well plate | Bio-Rad | #HSP9601 | / |
| Protein Clear HR Assay Kit | PerkinElmer | #CLS960014 | / |
| Protein Clear HR Chip | PerkinElmer | #CLS148695 | / |

| Instrument | Manufacturer | Catalog # |
|---|---|---|
| LabChip GXII Touch | PerkinElmer | CLS138160 |
| Thermostat C Thermoblock | Eppendorf | 5383000027 |

| Assay buffer | Composition/concentration |
|---|---|
| Non-reducing sample buffer | Protein Express Sample Buffer + 8.75 mM IAM |

After the reduction sensitivity assay was performed the samples were measured by use of the non-reducing protocol of the Protein Clear HR Assay according to the manufacturer's instructions.

To prepare the chip, all assay components were allowed to equilibrate to room temperature. Protein Clear HR Gel matrix was mixed with Protein Clear HR Dye solution and filtered before adding to rinsed chip wells according to the manufacturer's instructions.

The provided assay control VeriMAb-standard was diluted in non-reducing sample buffer, denatured at 70° C. for 10 minutes and mixed with water according to the manufacturer's instructions and placed in the LabChip GXII Touch instrument for assay calibration. After 1:10 dilution of Protein Clear HR Ladder in water the indicated volumes of the ladder solution and Protein Clear HR Wash buffer were transferred into corresponding tubes and placed in LabChip GXII Touch instrument. Calibration process was finished successfully before measuring the samples.

To prepare the samples, 5 µL of each sample coming from the reduction sensitivity assay was added to 18 µL of non-reducing sample buffer in a PCR plate, which was sealed, and samples were denatured at 70° C. for 10 min on a Thermostat C Thermoblock. After denaturation, the samples were diluted with 35 µL water. The prepared assay plate was stored at room temperature until it was measured with the LabChip GXII Touch instrument.

After measurement, the data was analyzed using the LabChip Reviewer Software. All peaks with ≥85% of relative peak area were integrated. The relative peak area [%] of the remaining intact molecule was plotted against the DTT concentrations and the curve was fitted by a 4 Parameter Logistic Model/Sigmoidal Dose-Response Model (XLfit, Dose Response One Site, Model 205). The area of the sample without DTT addition was used for standardization and was set to 100%. The DTT concentration of each sample where 50% of the intact molecule was remaining was used as EC50 value to evaluate the molecule's sensitivity towards reduction.

Antibody Sample Preparation after Reduction Assay for Tryptic Peptide Mapping Experiments After performing the reduction sensitivity assay samples were subjected to the digestion procedure. 100 µg per antibody sample were denatured using 0.2 mol/L histidine chloride, 5.6 mmol/L guanidinium hydrochloride pH 6 by buffer exchange with 0.5 mL Zeba Spin Desalting Columns (Thermo Fisher Scientific, Catalog No. 89883). Buffer exchange was repeated once to ensure complete removal of NEM. Then, samples were reduced by addition of 10 mmol/L TCEP (tris(2-carboxyethyl)phosphine, Thermo Fisher Scientific, Catalog No. T2556) for 1 h at 37° C. Subsequently, buffer was exchanged to 20 mmol/L histidine chloride, 0.5 mmol/L TCEP, pH 6 with 0.5 mL Zeba Spin Desalting Columns (Thermo Fisher Scientific, Catalog No. 89883). Antibodies were digested with trypsin overnight at 37° C. at an enzyme to substrate ratio of 1:20. Digestion was stopped by addition of 7 µL of 10% formic acid solution and samples were frozen at −80° C. until further analysis.

Detection of Modified Peptides by Liquid-Chromatography Tandem Mass-Spectrometry Peptides were analyzed using a VANQUUISH™ Flex UHPLC System coupled to an orbitrap FUSION™ LUMOS™ TRIBRID™ mass spectrometer equipped with the EASY-ETD ion source (Thermo Fisher Scientific, San Jose, CA, USA).

For peptide separation a binary solvent system was used: (A) 0.1% formic acid and (B) 90% acetonitrile, 0.1% formic acid. 2 µg of tryptic digested sample was separated with a 1 h gradient with linearly increasing concentrations of solvent B for 50 min, followed by 5 min at 95% B washing and 5 min re-equilibration to 5% solvent B on a HYPERSIL GOLD™ C18 LC-column (150 mm×2.1 mm with 1.9 µm particle size, Thermo Fisher Scientific, Catalog No. 25003-152130-V). Peptides separated on the column were detected with the following crucial settings: full MS spectra were acquired at a resolution of 120,000 (defined at 200 m/z) with the mass range set to 375-2000, an automated gain control (AGC) target of 4.0e5, a maximum injection time of 50 ms and 1 pscan. Data-dependent (MS/MS) spectra were acquired in a top 5 data-dependent mode using a resolution of 15,000 (defined at 200 m/z) after accumulation of 5.0e4 AGC targets within an injection time of 200 ms. Ions were isolated at a 1.6 Th isolation window and fragmented using HCD, ETHcD or ETciD at 30% normalized collision energy. Dynamic exclusion was set to 10 s.

Data Processing

Acquired MS data was processed using Expressionist software (GeneData version 13.5) and manually inspected to ensure correct assignment and relative quantification accuracy. Mass spectra were searched against the amino acid sequence of the sample molecule. Crucial settings are the mass tolerances for MS and MS/MS spectra which was set to 10 ppm, respectively. Post-translational modifications considered within the search parameters were NEM modification on cysteines and common N-terminal glycosylations using the IgG N-glycan library from Expressionist.

Results

EC50 values, as shown in Table 6C below, were calculated from the dose response curves. The reductions of main peak of unreduced sample by DTT measured by capillary electrophoresis (cGE) were identical for mAb3 wt, mAb3 ADE and mAb3 ADE-DSB, indicating that neither the ADE mutation nor the engineered disulfide bond in the CH2 domain have an influence on the reduction sensitivity of the protein.

The proteins, mAb3 wt, mAb3 ADE, and mAb3 ADE-DSB, from the reduction sensitivity assay analyzed by peptide mapping exhibit similar reduction behavior of reduction sensible intermolecular disulfide bonds (DSBs). Based on the dose response curves EC50 values were estimated for the three proteins to be in the range of 1.2-1.5 mM DTT indicating that the engineered DSB is similarly reduction stable as a typical intermolecular DSB.

TABLE 6C

EC50 values calculated from dose response curves of reduction of main peak of unreduced sample by DTT measured by capillary electrophoresis (cGE)

| Protein sample | EC50 [mM DTT] |
| --- | --- |
| Adapt_Standard (mAb Ctrl) | 0.8 |
| mAb3 wt | 1.2 |
| mAb3 ADE | 1.2 |
| mAb3 ADE-DSB | 1.2 | mAb4

The following further Fc variants were made based on mAb4 (an IgG1 monoclonal tetravalent bispecific CODV antibody directed against a protein antigen present at the surface of immune cells and a protein antigen present at the surface of cancer cells): mAb4 (wt) (wild-type IgG1 Fc), mAb4-DE (corresponding to mAb4 with the additional substitutions S239D and I332E), mAb4-DE-R292Q/V302Q (corresponding to mAb4-DE with the additional substitutions R292C and V302C), mAb4-R292Q/V302Q (corresponding to mAb4 wt with the substitutions R292C and V302C), mAb4-ADE (corresponding to mAb4 with the additional substitutions G236A, S239D, and I332E), and mAb4-ADE-R292Q/V302Q (corresponding to mAb4-ADE with the additional substitutions R292C and V302Q).

The mAb4 antibodies were produced as follows:

The expression plasmids encoding the different chains of the corresponding constructs were propagated in *E. coli* DH5a. Plasmids used for transfection were prepared from *E. coli* with EndoFree Plasmid Mega kits (Qiagen). HEK 293-FS cells growing in F17 serum free suspension culture (Invitrogen) were transfected with indicated plasmids using polyethyleneimine transfection reagent. After 6 days of cultivation at 37° C. with 8% CO2 cells were removed by centrifugation and the supernatant was passed over a 0.22 µm filter to remove particles. The Proteins were captured on MabSelect SuRe (Cytiva) and eluted with 0.1M Citrate buffer pH 3.0 and neutralized with 1M Tris pH9. After polishing the proteins by size exclusion chromatography (SEC) using a Superdex200 26/60 (Cytiva) and 0.22 µm filter and UV280 concentration determination the proteins were used for further characterization. The yields are reported below in Table 7.

TABLE 7

Yield of mAb4 with a wild-type IgG1 or with enhanced Fc domain, with or without disulfide bond

| Clone | Sample Yield (mg/L) |
| --- | --- |
| mAb4-WT | 30.6 |
| mAb4-DE | 2.7 |
| mAb4-ADE | 4.7 |
| mAb4-DE-R292C/V302C | 17.9 |
| mAb4-ADE-R292C/V302C | 19.4 |

The mAb4 molecule with a normal IgG1 Fc demonstrated a sample yield of 30.6 mg/L while the mAb4 molecules with ADE or DE mutations in the Fc part show a significant reduction in the sample yields with values below 5 mg/L. The mAb4 molecules with an IgG1 Fc with ADE or DE mutations and with the disulfide-bond demonstrated an increase in the sample yield. mAb4-DE-R292C/V302C shows a sample yield of 17.9 mg/L and mAb4-ADE-R292C/V302C a sample yield of 19.4 mg/L.

Thermostability of the mAb4 antibodies were tested with the same method as described above for mAb1 and the results are provided in Table 8.

TABLE 8

Thermostability of mAb4 with a wild-type IgG1 or with enhanced Fc domain, with or without disulfide bond

| Clone | Tonset | Tm1 |
| --- | --- | --- |
| mAb4-WT | 59.0 | 66.4 |
| mAb4-DE | 45.3 | 50.3 |
| mAb4-ADE | 44.6 | 49.9 |
| mAb4-DE-R292C/V302C | 59.4 | 67.2 |
| mAb4-ADE-R292C/V302C | 58.2 | 66.6 |

The mAb4 molecule with normal IgG1 Fc is stable with a Tm1 of 66.4° C. and a Tonset of 59° C. The mAb4 molecules with ADE or DE mutation in the IgG1 Fc demonstrate Tm1 and Tonset at or below 50° C. mAb4 molecules with an IgG1 Fc with ADE or DE mutations and with the disulfide-bond show an increase in thermostability. The mAb4-DE-R292C/V302C molecule shows a Tm at 67.2° C. and Tonset of 59.4° C. and the mAb4-ADE-R292C/V302C shows a Tm of 66.6° C. and a Tonset of 58.2° C.

Figure 10:
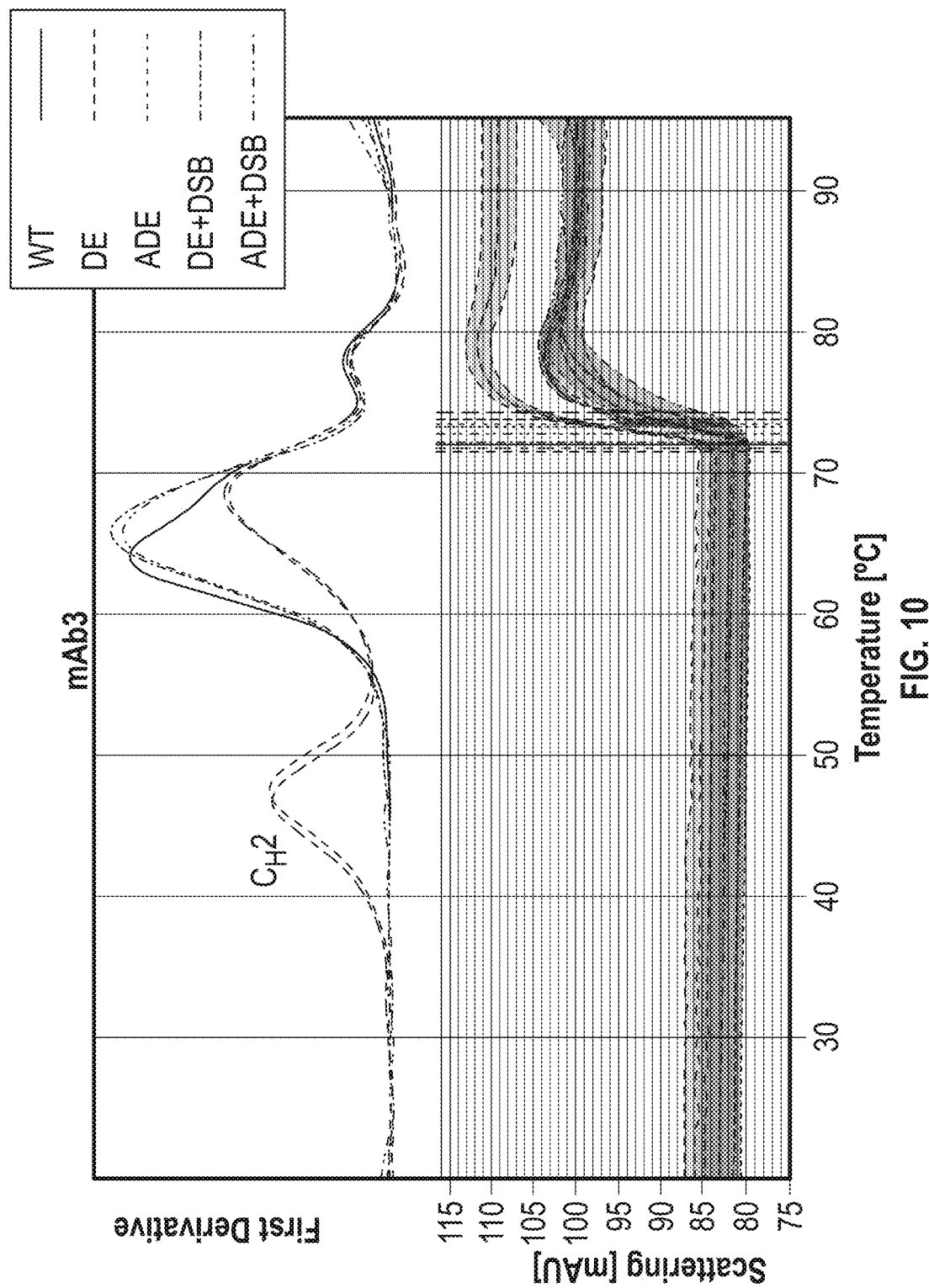
FIG. 10 depicts the thermostability effects of disulfide stabilization for mAb3 and mAb4 DE, ADE, DE+DSB (R292C-V3020), and ADE+DSB (R292C-V3020) variants as determined by nano differential scanning fluorimetry (nanoDSF). The left panel depicts mAb3 variants and the right panel depicts mAb4 variants with the following color code green DE, red ADE, DE+DSB purple, ADE DSB blue, WT black.
Figure 10:
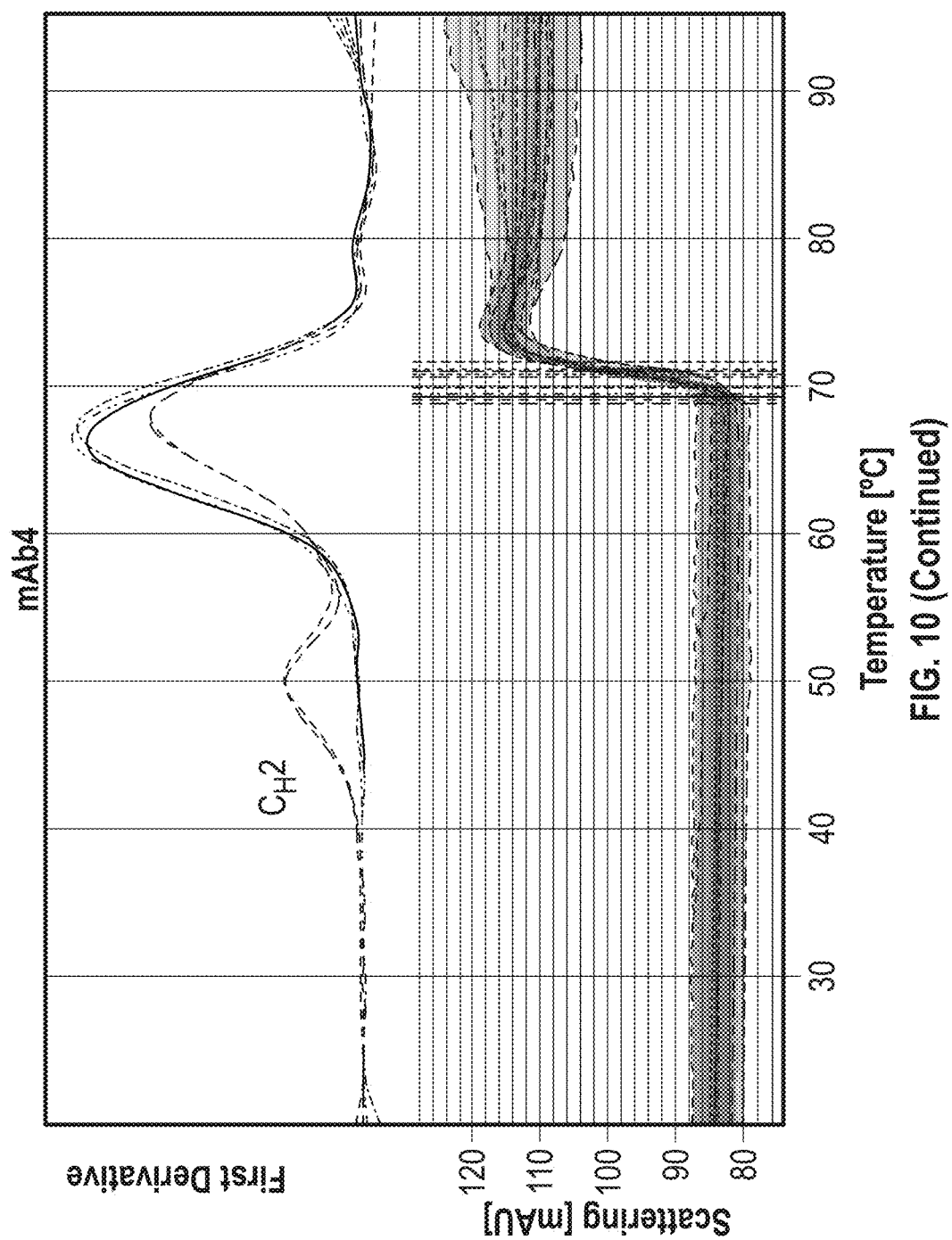

FIG. 10 depicts the thermostability effects of disulfide stabilization for DE, ADE, DE+DSB, and ADE+DSB as determined by nano differential scanning fluorimetry (nanoDSF). The left panel depicts mAb3 and the right panel depicts mAb4. Stabilization with R292C/V302C leads to a gain in thermostability by about 10° C.

Example 3: Binding Parameters of the Stabilized mAb1 Variants

Methods and Materials

Flow cytometry was used to determine bivalent EC50 binding of mAb1 to several recombinant cell lines expressing the target antigen: human preB-300.19 cells, cynomolgus preB-300.19 cells, HEK293T-FcγRIIIa F158, FcγRIIIa V158, and CHO-human FcRn expressing cells (GenScript; M00603). Cells were cultured in 96-well plates until a density of 40,000 cells/well was reached. The mAbs (100

μL/well) were added for 45 min at 4° C. After incubation, the wells were washed three times with PBS+1% BSA. Goat anti-human IgG-Alexa488 antibody was added for 45 min at 4° C. and washed three times with PBS+1% BSA. Antibody binding was evaluated after centrifugation and resuspension of cells by adding 200 μL/well PBS+1% BSA, and binding was evaluated using the Guava easyCyte 8HT Flow Cytometry System. Apparent KD and EC50 values were estimated using BIOST@T-BINDING and BIOST@T-SPEED software, respectively.

Kinetics of antibodies binding to huFcγRIIIa proteins were measured by Surface Plasmon Resonance (SPR) assay on Biacore T200 instrument at 25° C. in HBS-EP+buffer (10 mM HEPES, 150 mM NaCl, 3 mM EDTA, and 0.05% v/v Surfactant P20, pH 7.4). Human FcγRIIIa_His proteins (huFcγRIIIa_V158; huFcγRIIIa_F158) were captured at 0.05 ug/mL on an anti-His surface (CM5 sensorchip immobilized with anti-His antibody). A series of antibody concentrations starting from 2.5 μM were injected for 1 min, and dissociation was monitored for 3.5 min (30 μL/min). The anti-His surface is regenerated with a 1 min pulse of 10 mM Glycine-HCl pH 1.5 (10 μL/min).

The kinetics of antibodies binding to human FcRn (huFcRn) protein were measured by SPR on Biacore T200 instrument at 25° in PBST buffer (1.5 mM KH2PO4, 2.7 mM Na2HPO4-7H2O, 300 mM NaCl, 0.05% Tween-20, pH 6.0). The huFcRn was captured on a sensorchip_CAP-Streptavidin. A series of antibody concentrations starting from 2 μM were then injected for 1 min and dissociation was monitored for 1.5 min (30 μL/min). The surface was regenerated with one 2 min pulse of 6 M guanidine hydrochloride, 0.25 M NaOH (10 μL/min).

Antigen Binding (FACS)

The results of the mAb1 variants binding to both human and cynomolgus target antigens can be found in Table 9. Independent of the mutations introduced into the Fc domains, binding to the target antigen was similar. EC50 values were between 0.65 and 0.85 nM for human target antigen, and the EC50 values were between 1.36 and 1.78 for the cynomolgus target antigen. Introduction of the engineered disulfide bonds did not impact the binding to the target antigen.

TABLE 9

Binding to the target antigen, as measured by FACS mAb1 +/− ADE +/− DQ +/− DSB

| | | | | | | | |
|---|---|---|---|---|---|---|---|
| ADE+/− | IgG1_ADE | IgG1_ADE | IgG1_ADE | IgG1_ADE | IgG1_ADE | IgG1_ADE | IgG1 |
| DQ+/− | DQ | DQ | DQ | | | | |
| DSB | R292C_V302C | L242C_K334C | | R292C_V302C | L242C_K334C | | |
| Batch | VA2-21-262-1 | VA2-21-261-1 | VA2-21-266-1 | VA2-21-260-1 | VA2-21-259-1 | VA2-19-943-1 | VA2-20-950-1 |
| | | | Binding to by FACS EC50 (nM) Assay 1 n = 3 | | | | |
| Human Antigen | 0.62 ± 0.05 | 0.59 ± 0.07 | 0.61 ± 0.04 | 0.60 ± 0.14 | 0.60 ± 0.12 | 0.55 ± 0.09 | 0.63 ± 0.11 |
| Cyno Antigen | 1.52 ± 0.22 | 1.45 ± 0.24 | 1.52 ± 0.20 | 1.47 ± 0.19 | 1.51 ± 0.16 | 1.38 ± 0.10 | 1.49 ± 0.13 | mAb1 +/− ADLE +/− DQ +/− DSB

| | | | | | | |
|---|---|---|---|---|---|---|
| ADLE+/− | IgG1_ADLE | IgG1_ADLE | IgG1_ADLE | IgG1_ADLE | IgG1_ADLE | IgG1 |
| DQ+/− | DQ | DQ | | | | |
| DSB | R292C_V302C | L242C_K334C | | R292C_V302C | L242C_K334C | |
| Batch | VA2-20-953-1 | VA2-20-954-1 | VA2-21 -268-1 | VA2-2 1-267-1 | VA2-20-949-1 | VA2-20-950-1 |
| | | | Binding to Antigen by FACS EC50 (nM) Assay 1, n = 3 | | | |
| Human Antigen | | | 0.62 ± 0.06 | 0.62 ± 0.07 | 0.60 ± 0.14 | 0.63 ± 0.11 |
| Cyno Antigen | | | 1.54 ± 0.16 | 1.50 ± 0.20 | 1.48 ± 0.21 | 1.49 ± 0.13 |
| | | | Binding to Antigen by FACS EC50 (nM) Assay 2, n = 1 | | | |
| Human Antigen | 0.84 | 0.85 | | | 0.65 | 0.72 |
| Cyno Antigen | 1.70 | 1.67 | | | 1.36 | 1.39 | mAb1 +/− DE +/− DQ +/− DSB

| | | | | | | |
|---|---|---|---|---|---|---|
| DE+/− | IgG1_DE | IgG1_DE | IgG1_DE | IgG1_DE | IgG1_DE | IgG1 |
| DQ+/− | DQ | DQ | | | | |
| DSB | R292C_V302C | L242C_K334C | R292C_V302C | L242C_K334C | | |
| Batch | VA2-20-956-1 | VA2-20-957-1 | VA2-21-270-1 | VA2-21-269-1 | VA2-20-951-1 | VA2-20-9501 |
| | | | Binding to Antigen by FACS EC50 (nM) Assay 1, n = 3 | | | |
| Human Antigen | | | 0.64 ± 0.09 | 0.62 ± 0.06 | 0.63 ± 0.11 | 0.63 ± 0.11 |
| Cyno Antigen | | | 1.55 ± 0.28 | 1.49 ± 0.19 | 1.50 ± 0.19 | 1.49 ± 0.13 |
| | | | Binding to Antigen by FACS EC50 (nM) Assay 2, n = 1 | | | |
| Human Antigen | 0.86 | 0.75 | | | 0.79 | 0.72 |
| Cyno Antigen | 1.78 | 1.62 | | | 1.45 | 1.39 | huFcγRIIIa V/F158 Kinetics and FACS

Binding of the mAbs to human FcγRIIIa proteins were measured by SPR and FACS. The results can be found in Table 10. For all the variants with a Fc domain comprising the DE, ADE and ADLE mutations, binding to FcγRIIIa V158 or F158 significantly improved compared to binding of an antibody with a WT IgG1 to FcγRIIIa V158 or F158, as measured by FACS and SPR. A 10 to 100-fold improvement as measured by FACS, and a 6 to 20-fold (resp 18 to 29-fold) improvement by SPR for FcγRIIIA V158 (resp. FcγRIIIA F158). Introduction of an engineered disulfide bond, either L242C/K334C or R292C/V302C, did not impact mAb1 binding to FcγRIIIa V158 or F158.

TABLE 10

Binding to FcγRIIIa V158 and F158, as measured by FACS and SPR mAb1 +/− ADE +/− DQ +/− DSB

| ADE+/− | IgG1_ADE | IgG1_ADE | IgG1_ADE | IgG1_ADE | IgG1_ADE | IgG1_ADE | IgG1 |
|---|---|---|---|---|---|---|---|
| DQ+/− | DQ | DQ | DQ | — | — | — | — |
| DSB | R292C_V302C | L242C_K334C | — | R292C_V302C | L242C_K334C | — | — |
| Batch | VA2-21-262-1 | VA2-21-261-1 | VA2-21-266-1 | VA2-21-260-1 | VA2-21-259-1 | VA2-1 9-943-1 | VA2-20-950-1 |
| Binding to FcγRIIIA by FACS (EC50 nM) Assay 1 n = 3 ||||||||
| V158 | 10 ± 3 | 7 ± 4 | 4 ± 1 | 12 ± 4 | 5 ± 2 | 3 ± 1 | 186 ± 70 |
| F158 | 17 ± 1 | 19 ± 3 | 13 ± 4 | 19 ± 1 | 18 ± 4 | 9 ± 1 | 1064 ± 70 |
| Binding to FcγRIIIA by SPR (KD nM) Assay 1 n = 3 ||||||||
| V158 | 214 ± 25 | 191 ± 18 | 155 ± 5 | 172 ± 18 | 162 ± 4 | 107 ± 4 | 1623 ± 153 |
| F158 | 202 ± 71 | 211 ± 47 | 183 ± 14 | 211 ± 16 | 193 ± 14 | 150 ± 6 | 3870 ± 397 | mAb1 +/− ADLE +/− DQ +/− DSB

| ADLE+/− | IgG1_ADLE | IgG1_ADLE | IgG1_ADLE | IgG1_ADLE | IgG1_ADLE | IgG1_ADLE | IgG1 |
|---|---|---|---|---|---|---|---|
| DQ+/− | DQ | DQ | DQ | — | — | — | — |
| DSB | R292C_V302C | L242C_K334C | — | R292C_V302C | L242C_K334C | — | — |
| Batch | VA2-20-953-1 | VA2-20-954-1 | VA2-20-952-1 | VA2-21-268-1 | VA2-21-267-1 | VA2-20-949-1 | VA2-20-950-1 |
| Binding to FcγRIIIA by FACS (EC50 nM) Assay 1 n = 3 ||||||||
| V158 | | | | 12 ± 3 | 5 ± 2 | 3 ± 1 (2.71 ± 0.42) | 186 ± 70 1064 ± 70 |
| F158 | | | | 25 ± 3 | 11 ± 4 | 4 ± 1 (4.37 ± 0.53) | |
| Binding to FcγRIIIA by FACS (EC50 nM) Assay 2 n = 1 ||||||||
| V158 | 26 | 9 | | | | 5 | 244 |
| F158 | 52 | 13 | | | | 7 | 744 |
| Binding to FcγRIIIA by SPR (KD nM) Assay 1 n = 3 ||||||||
| V158 | | | 88 ± 4 | 258 ± 5 | 161 ± 21 | 77 ± 4 | 1623 ± 153 |
| F158 | | | 105 ± 7 | 296 ± 16 | 148 ± 23 | 94 ± 3 | 3870 ± 397 |
| Binding to FcγRIIIA by SPR (KD nM) Assay 2 n = 3 ||||||||
| V158 | 56 ± 4 | 33 ± 1 | 28 ± 4 | | | 22 ± 2 | 386 ± 29 |
| F158 | 70 ± 18 | 49 ± 2 | 38 ± 2 | | | 46 ± 27 | 1331 ± 111 | mAb1 +/− DE +/− DQ +/− DSB

| DE+/− | IgG1_DE | IgG1_DE | IgG1_DE | IgG1_DE | IgG1_DE | IgG1_DE | IgG1 |
|---|---|---|---|---|---|---|---|
| DQ+/− | DQ | DQ | DQ | — | — | — | — |
| DSB | R292C_V302C | L242C_K334C | — | R292C_V302C | L242C_K334C | — | — |
| Batch | VA2-20-956-1 | VA2-20-957-1 | VA2-20-955-1 | VA2-21-270-1 | VA2-21-269-1 | VA2-20-951-1 | VA2-20-950-1 |
| Binding to FcγRIIIA by FACS (EC50 nM) Assay 1 n = 3 ||||||||
| V158 | | | | 4 ± 1 | 2 ± 1 | 2 ± 1 | 186 ± 70 |
| F158 | | | | 11 ± 1 | 24 ± 12 | 11 ± 3 | 1064 ± 70 |
| Binding to FcγRIIIA by FACS (EC50 nM) Assay 2 n = 1 ||||||||
| V158 | 7 | 3 | | | | 4 | 244 |
| F158 | 20 | 27 | | | | 18 | 744 |
| Binding to FcγRIIIA by SPR (KD nM) Assay 1 n = 3 ||||||||
| V158 | | | 60 ± 5 | 101 ± 26 | 109 ± 27 | 57 ± 5 | 1623 ± 153 |
| F158 | | | 142 ± 11 | 88 ± 27 | 297 ± 43 | 141 ± 8 | 3870 ± 397 |
| Binding to FcγRIIIA by SPR (KD nM) Assay 2 n = 3 ||||||||
| V158 | 29 ± 2 | 18 ± 1 | 19 ± 1 | | | 17 ± 1 | 386 ± 29 |
| F158 | 50 ± 1 | 72 ± 6 | 58 ± 4 | | | 48 ± 11 | 1331 ± 111 | huFcγRIIa H/R131 Kinetics and FACS

Binding of the mAbs to human FcγRIIa proteins were measured by SPR and FACS. The results can be found in Table 11. The improved affinity to FcγRIIA in the IgG1_ADE format compared to the IgG1 vanished when the DSB R292C_V302C or L242C_K334C mutations are introduced with or without the presence of the DQ mutation. In the IgG1_ADLE or DE format the affinity to FcγRIIA remained low with and without the DSB mutations.

TABLE 11

Binding to FcγRIIIa H131 and R1 31, as measured by FACS and SPR mAb1 +/− ADE +/− DQ +/− DSB

| ADE+/− | IgG1_ADE | IgG1_ADE | IgG1_ADE | IgG1_ADE | IgG1_ADE | IgG1_ADE | IgG1 |
|---|---|---|---|---|---|---|---|
| DQ+/− | DQ | DQ | DQ | — | — | — | — |
| DSB | R292C_V302C | L242C_K334C | — | R292C_V302C | L242C_K334C | — | — |
| Batch | VA2-21-262-1 | VA2-21-261-1 | VA2-21-266-1 | VA2-21-260-1 | VA2-21-259-1 | VA2-19-943-1 | VA2-20-950-1 |

Binding to FcγRIIA by FACS (EC50 nM) Assay 1 n = 3

| H131 | 101 ± 33 | 68 ± 27 | 14 ± 2 | 92 ± 12 | 102 ± 34 | 20 ± 2 | 341 ± 64 |
| R131 | 45 ± 21 | 152 ± 56 | 18 ± 5 | 43 ± 12 | 142 ± 19 | 20 ± 1 | 303 ± 27 | mAb1 +/− ADLE +/− DQ +/− DSB

| ADLE+/− | IgG1_ADLE | IgG1_ADLE | IgG1_ADLE | IgG1 |
|---|---|---|---|---|
| DQ+/− | — | — | — | — |
| DSB | R292C_V302C | L242C_K334C | — | — |
| Batch | VA2-21-268-1 | VA2-21-267-1 | VA2-20-949-1 | VA2-20-950-1 |

Binding to FcγRIIA by FACS (EC50 nM) Assay 1 n = 3

| H131 | 155 ± 28 | 145 ± 85 | 70 ± 12 | 341 ± 64 |
| R131 | 144 ± 19 | 428 ± 170 | 85 ± 14 | 303 ± 27 | mAb1 +/− DE +/− DQ +/− DSB

| DE+/− | IgG1_DE | IgG1_DE | IgG1_DE | IgG1 |
|---|---|---|---|---|
| DQ+/− | — | — | — | — |
| DSB | R292C_V302C | L242C_K334C | — | — |
| Batch | VA2-21-270-1 | VA2-21-269-1 | VA2-20-951-1 | VA2-20-950-1 |
| FcγRIIA | | | | |

Binding to FcγRIIA by FACS (EC50 nM) Assay 1 n = 3

| H131 | 337 ± 142 | 319 ± 55 | 106 ± 29 | 341 ± 64 |
| R131 | 254 ± 6 | 319 ± 8 | 198 ± 44 | 303 ± 27 | huFcRn Kinetics and FACS

The results of the huFcRn binding studies can be found in Table 12. For all mAbs with the Fc variants with the DQ mutations, binding to huFcRn was improved compared to the Fc not having the DQ mutations. Introduction of DSB maintained this improvement when the Fc containing the _DQ mutations.

TABLE 12

Binding to huFcRn, as measured by FACS and SPR mAb1 +/− ADE +/− DQ +/− DSB

| ADE+/− | IgG1_ADE | IgG1_ADE | IgG1_ADE | IgG1_ADE | IgG1_ADE | IgG1_ADE | IgG1 |
|---|---|---|---|---|---|---|---|
| DQ+/− | DQ | DQ | DQ | — | — | — | — |
| DSB | R292C_V302C | L242C_K334C | — | R292C_V302C | L242C_K334C | — | — |
| Batch | VA2-21-262-1 | VA2-21-261-1 | VA2-21-266-1 | VA2-21-260-1 | VA2-21-259-1 | VA2-19-943-1 | VA2-20-950-1 |

Binding to huFcRn by SPR (KD nM) Assay 1 n = 3

| | 198 ± 3 | 161 ± 19 | 217 ± 2 | 1310 ± 221 | 829 ± 129 | 1040 ± 155 | 1210 ± 81 | mAb1 +/− ADLE +/− DQ +/− DSB

| ADLE+/− | IgG1_ADLE | IgG1_ADLE | IgG1_ADLE | IgG1_ADLE | IgG1_ADLE | IgG1_ADLE | IgG1 |
|---|---|---|---|---|---|---|---|
| DQ+/− | DQ | DQ | DQ | — | — | — | — |
| DSB | R292C_V302C | L242C_K334C | — | R292C_V302C | L242C_K334C | — | — |
| Batch | VA2-20-953-1 | VA2-20-954-1 | VA2-20-952-1 | VA2-21-268-1 | VA2-21-267-1 | VA2-20-949-1 | VA2-20-950-1 |

TABLE 12-continued

Binding to huFcRn, as measured by FACS and SPR

Binding to huFcRn by SPR (KD nM) Assay 1 n = 3

|  |  | 193 ± 15 | 1130 ± 111 | 956 ± 126 |  | 993 ± 153 | 1210 ± 81 |

Binding to huFcRn by SPR (KD nM) Assay 2 n = 3

| 184 ± 11 | 156 ± 20 | 196 ± 27 |  |  | 811 ± 28 | 941 ± 130 | mAb1 +/− DE +/− DQ +/− DSB

| DE+/−DQ+/−DSB Batch | IgG1_DE DQ R292C_V302C VA2-20-956-1 | IgG1_DE DQ L242C_K334C VA2-20-957-1 | IgG1_DE DQ — VA2-20-955-1 | IgG1_DE — R292C_V302C VA2-21-270-1 | IgG1_DE — L242C_K334C VA2-21-269-1 | IgG1_DE — — VA2-20-951-1 | IgG1 — — VA2-20-950-1 |

Binding to huFcRn by SPR (KD nM) Assay 1 n = 3

|  |  | 199 ± 6 | 864 ± 271 | 798 ± 88 |  | 996 ± 104 | 1210 ± 81 |

Binding to huFcRn by SPR (KD nM) Assay 2 n = 3

| 234 ± 41 | 169 ± 15 | 249 ± 41 |  |  | 761 ± 89 | 941 ± 130 |

Example 4: Binding Parameters of the Stabilized mAb2 Variants

Methods and Materials:
Surface Plasmon Resonance Assays
Fcγ Receptor Binding Using Surface Plasmon Resonance (SPR)
Analysis of antibody binding to recombinant human FcγRIIIa-V158 was performed on a Biacore T200 instrument using anti-His capture. Anti-tetra His (Qiagen) was buffer exchanged into PBS pH 7.2 (Gibco), diluted to 25 μg/mL in 10 mM sodium acetate pH 4.0 and directly immobilized to a series S CM5 chip to a surface density of ~10,000 RU using the amine coupling kit provided by GE Healthcare. His-tagged recombinant human FcγRIIIa-V158 (produced in-house) was diluted to 0.5 and 1 μg/mL in HBS-EP+(10 mM HEPES pH 7.4, 150 mM NaCl, 3 mM EDTA, 0.05% surfactant P20) and injected for 30 sec at 10 μL/min flowrate to obtain capture levels of 6 and 14 RU. mAb2-wt antibodies were serially diluted 3-fold from 3000 to 37 nM and mAb2-DE antibodies were diluted to 111, 37, 12, and 4 nM in running buffer and injected over the captured receptor for 2 min in duplicate followed by 2 min dissociation in buffer. The surface was regenerated with 10 mM glycine pH 1.5 for 30 sec. Sensorgrams were processed using the BiaEvaluation software (GE Healthcare) and fit to a 1:1 binding model to obtain kinetic constants. Reported KDs were averaged from both capture levels.

FcRn Binding Using Surface Plasmon Resonance (SPR)
Analysis of antibody binding to recombinant human, cynomolgus (cyno), and mouse FcRn was performed on a Carterra LSA instrument using an anti-Fab capture method. Goat anti-human IgG (F(ab')2 specific) (Jackson Labs) was diluted to 20 μg/mL in 10 mM sodium acetate pH 4.5 and directly immobilized to a HC200M chip to a surface density of ~9,000 RU using the amine coupling reagents provided by Carterra in 25 mM MES pH 6.0, 0.05% Tween-20 running buffer. mAb2 antibodies were printed to the anti-Fab surface in the capture array format at 6 and 15 μg/mL in PBSP+pH 6.0 (20 mM NaPi, 2.7 mM KCl, 137 mM NaCl, 0.05% surfactant P20) in separate quadrants in duplicate. Each species of FcRn (produced in-house) were serially diluted 2-fold in PBSP+pH 6.0 and injected over the captured mAb2 for either a 2 or 3 min association followed by 5 min dissociation to measure the affinity at pH 6.0. Each concentration series contained a total of 10 concentrations of FcRn with the highest concentration being FcRn species specific: 4000 nM, 2000 nM cyno, and 500 nM mouse FcRn. Buffer injections were evenly distributed between the receptor injections for proper blank subtraction. To measure the FcRn binding at pH 7.4, the mAb2 antibodies were captured as described above, while human and cyno FcRn were diluted to 1000 nM and mouse FcRn was diluted to 500 nM in PBSP+pH 7.4 and injected over the captured mAb2 for a 2 min association followed by 2 min dissociation. Sensorgrams were processed with the Carterra K.I.T. Inspection Tool and fit to a 1:1 binding model to obtain kinetic constants at pH 6.0 or calculate steady state response at the end of the association phase at pH 7.4. Reported binding affinities were averaged from all mAb2 prints from two separate assay runs for human FcRn and a single assay run for cyno and mouse FcRn.

Results:

TABLE 13

Binding Affinity to huFcgRIIIa-V158

| mAb2 variants | WT control | WT R292C_V302C | _DE | _DE R292C_V302C |
|---|---|---|---|---|
| Assay |  |  |  |  |
| Binding to huFcgRIIIa-V158 (SPR), KD (M) | 3.97E−07 | 5.24E−07 | 1.33E−08 | 1.83E−08 |

SPR results for binding to huFcgRIIIa-V158 show comparable affinities for mAb2-wt, mAb2-R292C/V302C. mAb2-DE and mAb2-DE-R292C/V302C show 22-39-fold higher binding affinity to huFcgRIIIa-V158 than WT or WT variant and have comparable affinities to each other.

TABLE 14

Binding Affinity to FcRn at pH 6.0

| mAb2 (IgG1) | WT control | WT R292C_V302C | _DE | _DE R292C_V302C |
|---|---|---|---|---|
| Assay | | | | |
| Binding to huFcRn (SPR) KD (nM) | 103.23 ± 530.64 | 111.58 ± 551.15 | 83.83 ± 506.15 | 50.61 ± 509.15 |
| Binding to cyFcRn (SPR) KD (nM) | 313.41 ± 35.52 | 324.54 ± 120.97 | 349.73 ± 70.81 | 325.91 ± 39.44 |
| Binding to moFcRn (SPR) KD (nM) | 146.64 ± 21.77 | 147.51 ± 59.87 | 142.08 ± 40.41 | 142.09 ± 21.06 |

Results show that addition of the R292_V302C mutation on mAb2-wt or on mAb2-DE had no significant effect on the binding affinity to human, cyno, or mouse FcRn. Affinities were comparable for all molecules to each species.

TABLE 15

Steady State Binding Response to FcRn at pH 7.4

| mAb2 (IgG1) | WT control | WT R292C_ V302C | DE | _DE R292C_ V302C |
|---|---|---|---|---|
| Batch | | | | |
| Binding to huFcRn (SPR) Steady State Response (RU) | 0.06 ± 0.83 | −0.03 ± 0.95 | 0.28 ± 0.18 | 0.08 ± 1.06 |
| Binding to cyFcRn (SPR) Steady State Response (RU) | 0.32 ± 0.68 | 0.20 ± 0.77 | 0.36 ± 0.74 | 0.20 ± 0.83 |
| Binding to moFcRn (SPR) Steady State Response (RU) | 0.87 ± 0.95 | 0.66 ± 1.14 | 0.54 ± 0.91 | 0.58 ± 0.19 |

Results show that none of the mAb2 molecules bound to human, cyno, or mouse FcRn at neutral pH under the conditions tested.

Example 5: Binding Parameters of the Stabilized mAb3 Variants to Human CD16a

Both mAb3 and mAb4 possess Fc domains that are capable of binding CD16a. Binding to CD16a was measured to demonstrate that the DSB substitutions (R292C/V302C) do not eliminate CD16a binding. As shown in Table 16, all DSB variants had equal or greater binding to both CD16a variants (V158 or F158) compared to the DE or ADE variant alone.

TABLE 16 mAb3 and mAb4 binding parameters to human CD16a

| Antibody | Binding to huCD16a (V158) KD [nM] | Binding to huCD16a (F158) KD [nM] |
|---|---|---|
| mAb3 WT | 705 ± 214 | 1265 ± 287 |
| mAb3-DE | 66 ± 25 | 67.2 ± 11 |
| mAb3-ADE | 113 ± 40 | 87.5 ± 6 |
| mAb3-DE-DSB (R292C/V302C) | 110 | 113 |
| mAb3-ADE-DSB (R292C/V302C) | 165 | 121 |
| mAb4 | 618 ± 59 | 1376 ± 456 |
| mAb4-DE | 87 ± 48 | 63.5 |
| mAb4-ADE | 116 ± 37 | 86.9 |
| mAb4-DE-DSB (R292C/V302C) | 87 | 80.4 ± 9 |
| mAb4-ADE-DSB (R292C/V302C) | 155 | 114 |

Example 6: In Vitro Characterization of Disulfide Bond Stabilized Variants mAb1

A—Assessment of the Capability of the Variant to Induce Complement-Dependent Cytotoxicity (CDC) In Vitro.

Materials and Methods:

The CDC capacity of mAb1 was evaluated using the DND41 cell line (T-ALL, T cell acute lymphoblastic leukemia cells, Leukemia 8:425-434(1994)) expressing the target. Cells were suspended at 3.106 in RHBP medium (RPMI 1640 without phenol red, 0.1% BSA, 2 mM HEPES, 2 mM glutamine).

Cells were plated at $1.5 \times 10^5$ cells per well in a 96-well plate, and pre-incubated 30 minutes at 4° C. with 25 µl of the antibody variants at serial dilution concentrations starting from 167.5 nM to 0.08 nM with a dilution factor of 2.

In a second step, 25 µL of human complement were added per well (Sigma, Ref: S1764-1 mL, resuspended in 1 mL $H_2O$+4 mL RHBP) and the plates were incubated for 2 hours at 37° C. with 5.5% of $CO_2$. WST-1 Solution (Roche, Ref 11 644 807 001; 10 µL/well) was added and plates were incubated again for 2 hours at 37° C. with 5.5% $CO_2$.

Absorbance was measured on a SpectraMax Plus spectrophotometer (Molecular Devices) at 440 nm according to the manufacturer's protocol. Each point was performed in triplicate.

The % of viability was calculated as follows:

$$\% \text{ viability} = ((OD\_sample - OD\ medium) \times 100) / (OD\_cells\ without\ antibodies - OD\ medium).$$

OD: Optical Density

Data are a summary of three independent experiments.

Figure 11:
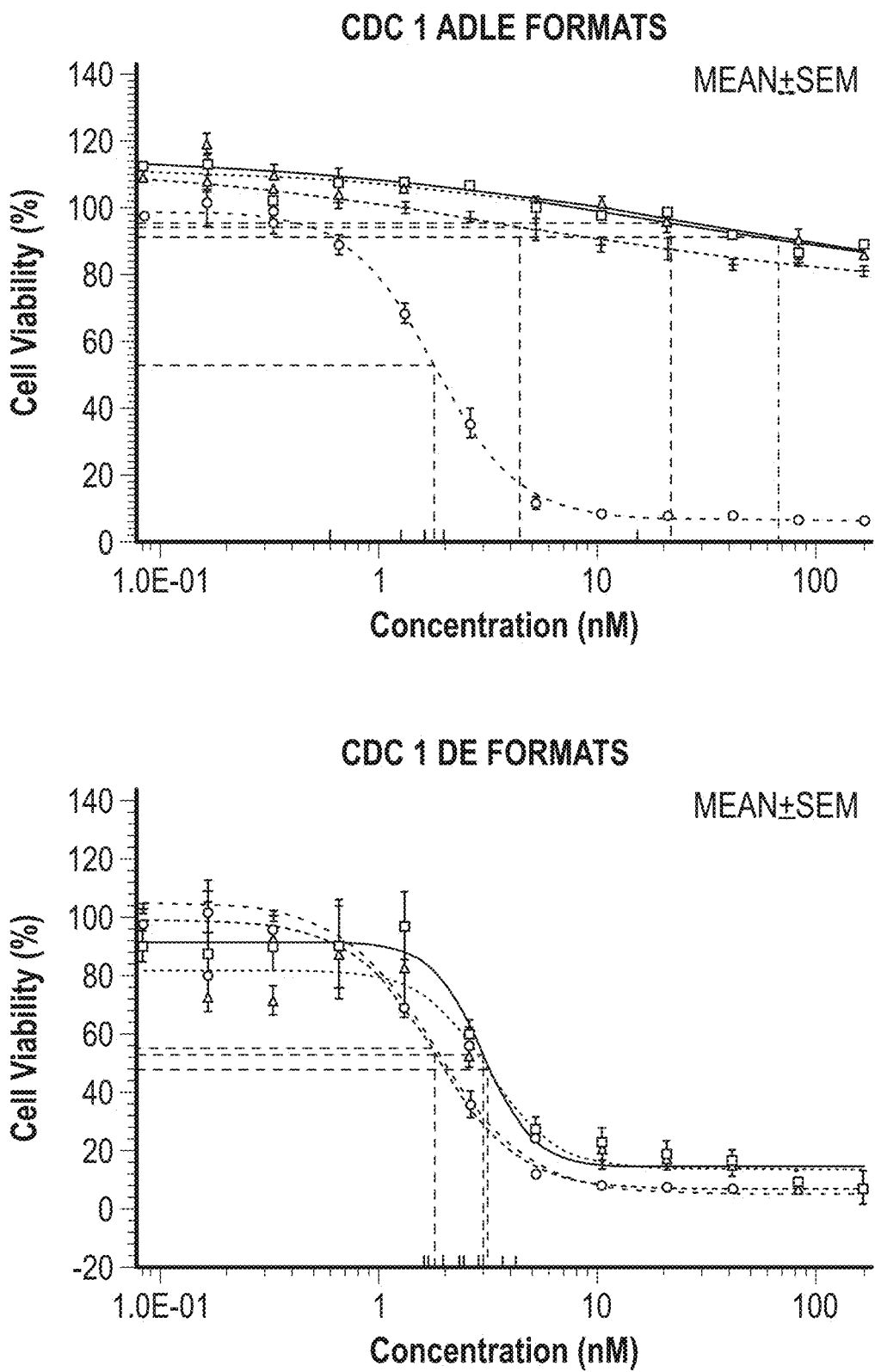
FIG. 11 depicts the CDC activity of the ADLE variants, the DE variants, and ADE variants as compared to IgG1 wild-type for mAb1+/−ADLE, DE or ADE+/−DSB (L242C_K334C or R292C_V302C).
Figure 11:
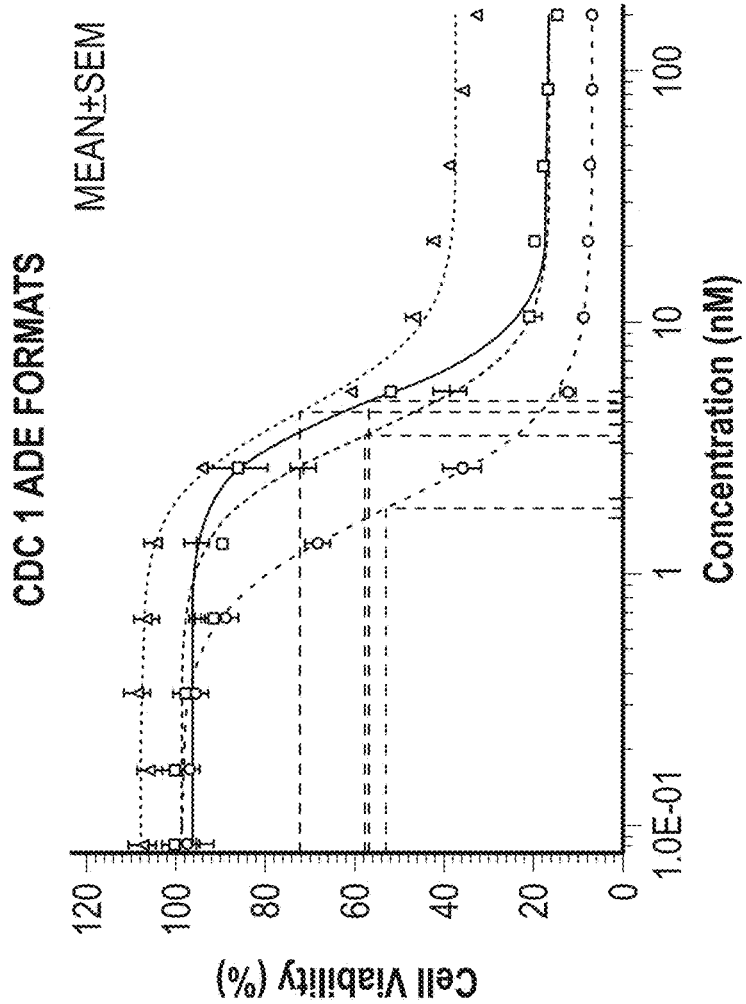
Figure 12:
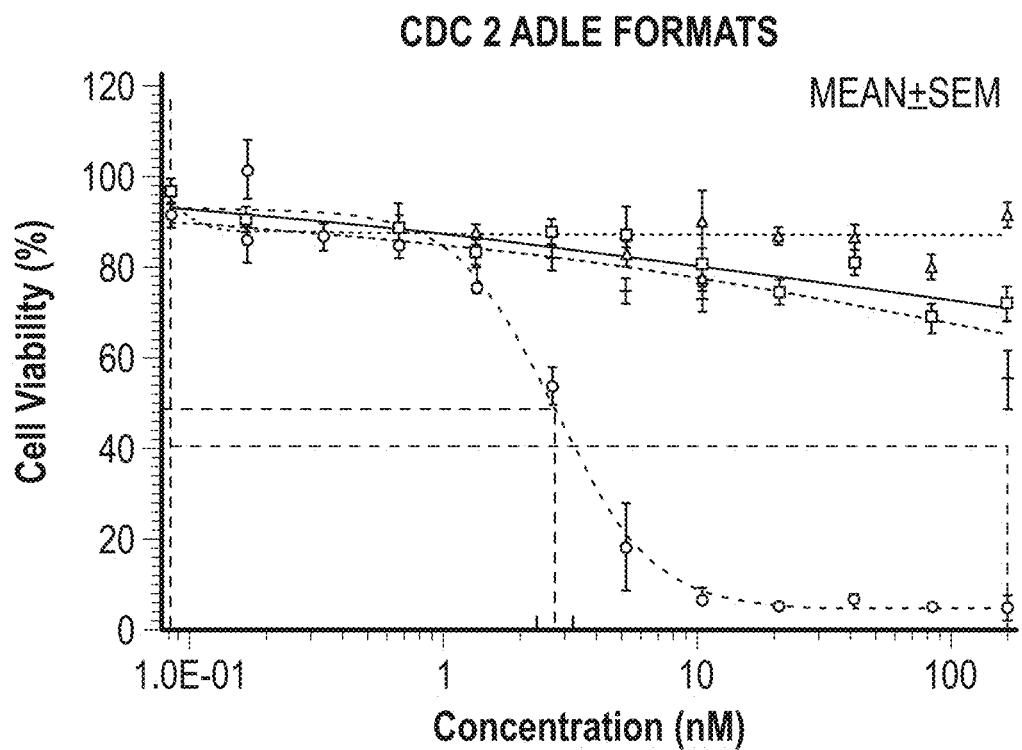
FIG. 12 depicts the CDC activity of the ADLE variants, the DE variants, and ADE variants as compared to IgG1 wild-type for mAb1+/−ADLE, DE or ADE−/30 DQ+/−R292C_V302C.
Figure 12:
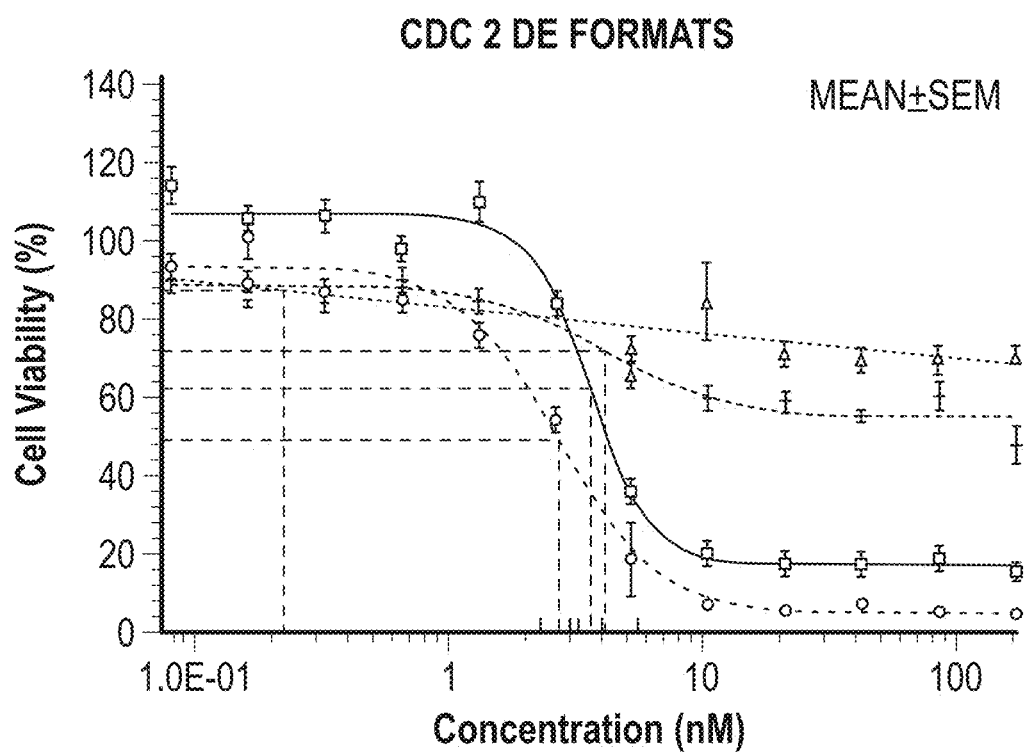
Figure 12:
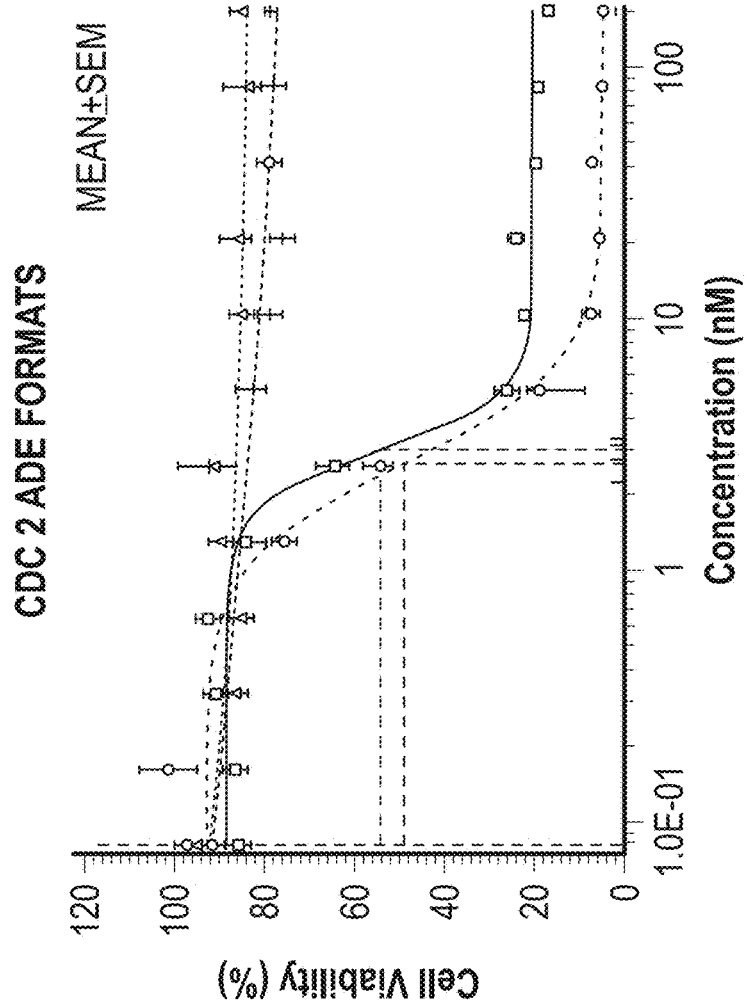
Figure 13:
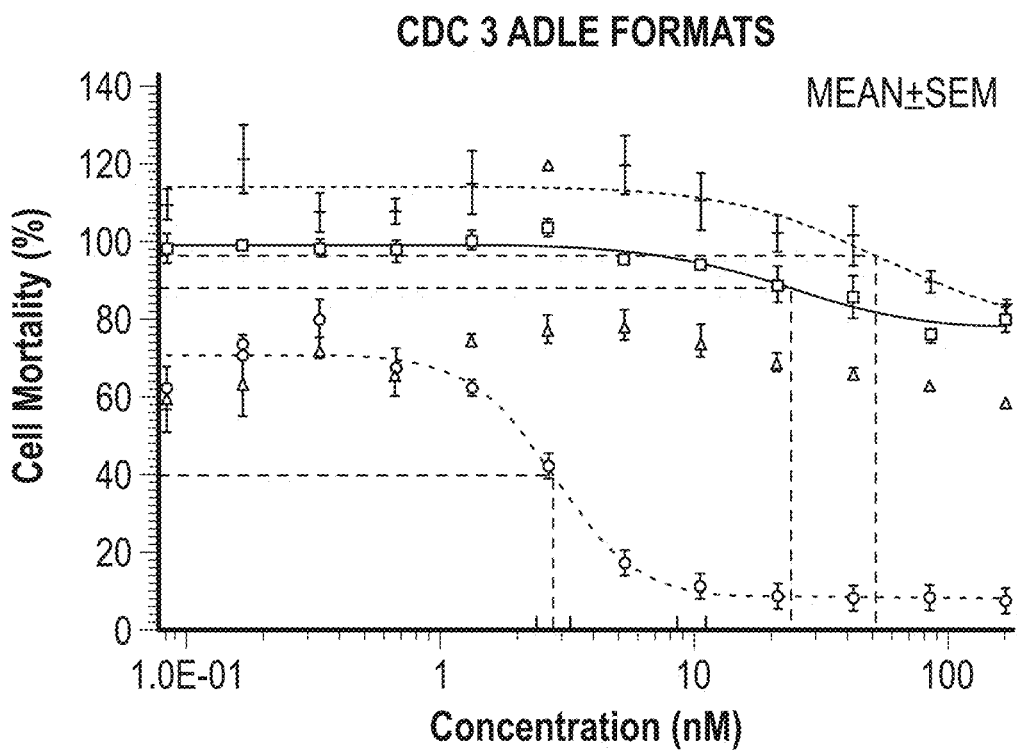
FIG. 13 depicts the CDC activity of the ADLE variants, the DE variants, and the ADE variants as compared to IgG1 wild-type for mAb1+ADLE, DE or ADE−/+DQ+/−L242C_K334C.
Figure 13:
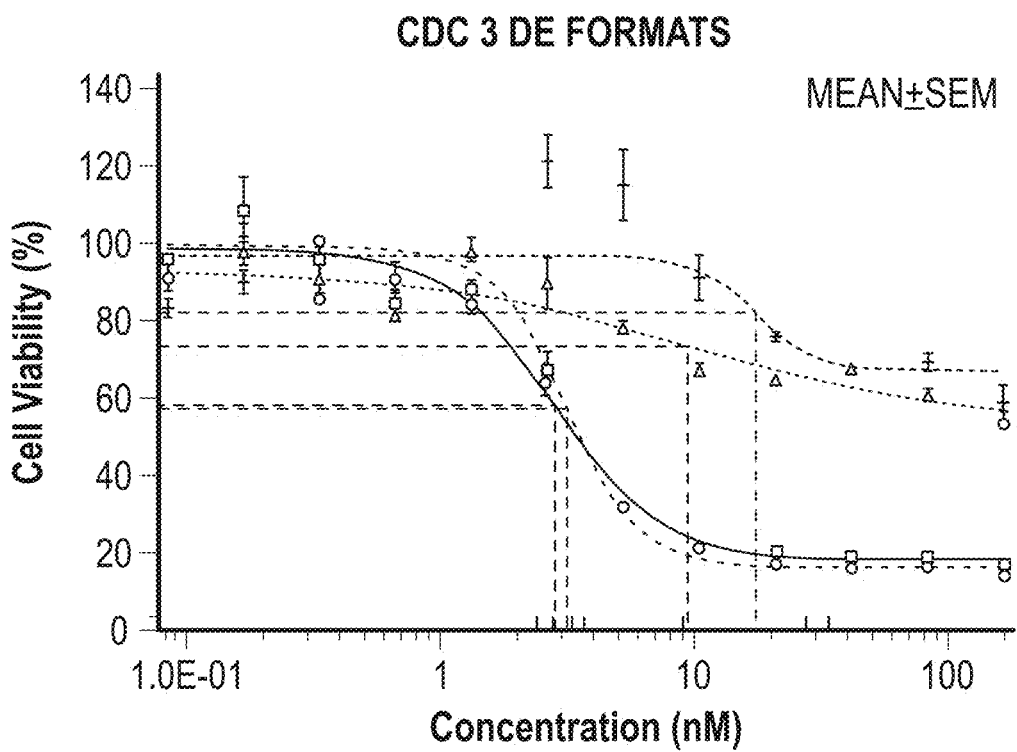
Figure 13:
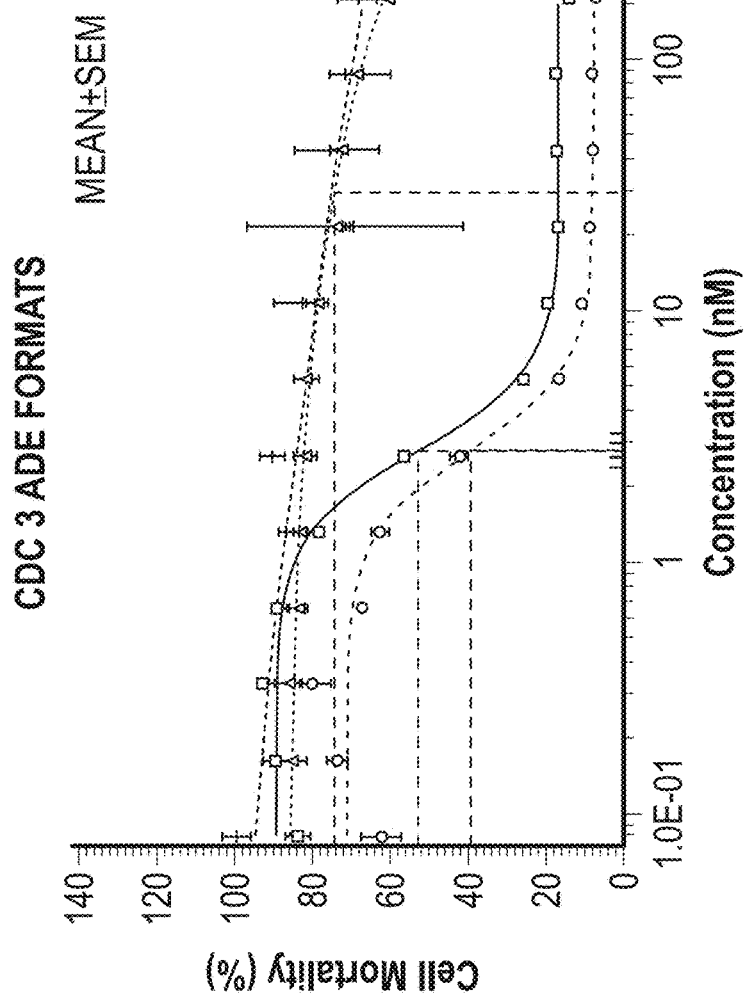

The reported results are the geometrical mean of IC50 values, CV and delta of mortality (Table 17 to Table 19), as well as a representative example of the CDC activity of ADE formats, ADLE formats, and DE formats (FIG. 11, FIG. 12, and FIG. 13). Values were calculated using Biost@t-SPEED v2.4.

Results:

TABLE 17

CDC activity IC50 values for mAb1 +/− ADLE, DE or ADE +/− DSB (L242C_K334C or R292C_V302C)

| | mAb1 IgG1 | | | | | | | | | |
|---|---|---|---|---|---|---|---|---|---|---|
| | iso ADLE | ADLE L242C_ K334C | ADLE R292C_ V302C | iso DE | DE R292C_ V302C | DE L242C_ K334C | iso ADE | ADE R292C_ V302C | ADE L242C_ K334C | WT control |
| | | | | | Batch | | | | | |
| Variable Region | VA2-20-034.2 | VA2-21-267-1 | VA2-21-268-1 | VA2-20-1117-1 | VA2-21-270-1 | VA2-21-269-1 | VA2-19-943-1 | VA2-21-260-1 | VA2-21-259-2 | VA2-20-950-1 |
| IC50(nM) | NA | NA | NA | 3.03 | 1.89 | 3.11 | 3.49 | 3.33 | 4.13 | 2.10 |
| IC50 [95% CI] | NA | NA | NA | [2.63; 3.49] | [1.75; 2.04] | [2.56; 3.77] | [3.12; 3.92] | [3.06; 3.61] | [3.62; 4.71] | [1.88; 2.34] |
| IC50 CV % | NA | NA | NA | 6.59 | 3.66 | 8.94 | 5.43 | 4.07 | 6.25 | 5.08 |
| Delta (Top-Bottom) % | NA | NA | NA | 79.56 | 88.63 | 72.93 | 68.29 | 70.16 | 59.99 | 87.19 |

NA: No fitting obtained

No CDC activity is detected with the ADLE format and with all the additional mutations containing the ADLE format, Table 17 and FIG. 11. Whereas CDC activity is measured with the DE or ADE format and does not change with the additional disulfide bond mutations introduced in the DE or ADE format.

TABLE 18

CDC activity IC50 values for mAb1 +/− ADLE, DE or ADE −/+ DQ +/− R292C_V302C

| | mAb1 IgG1 | | | | | | | | | |
|---|---|---|---|---|---|---|---|---|---|---|
| | iso ADLE | ADLE DQ | ADLE DQ_ R292C_ V302C | iso DE | DE DQ | DE DQ_ R292C_ V302C | iso ADE | ADE DQ | ADE DQ_ R292C_ V302C | WT control |
| | | | | | Batch | | | | | |
| Variable Region | VA2-20-034.2 | VA2-20-952-1 | VA2-20-953-1 | VA2-20-1117-1 | VA2-20-955-1* | VA2-20-956-1** | VA2-19-943-1 | VA2-21-266-1 | VA2-21-262-1 | VA2-20-950-1 |
| IC50 (nM) | NA | NA | NA | 3.12 | 2.84 | 3.87 | 3.17 | NA | NA | 2.01 |
| IC50 [95% CI] | NA | NA | NA | [2.72; 3.58] | [2.31; 3.49] | [2.93; 5.12] | [2.82; 3.57] | NA | NA | [1.78; 2.27] |
| IC50 CV % | NA | NA | NA | 6.38 | 10.17 | 13.56 | 5.58 | NA | NA | 5.85 |
| Delta (Top-Bottom) % | NA | NA | NA | 87.47 | 87.60 | 44.51 | 80.22 | NA | NA | 88.32 |

*Fitting obtained only in 1 out of 3 assays
**Fitting obtained in 2 out of 3 assays No CDC activity was detected with the ADLE format and with the additional DQ and R292C_V302C disulfide bond mutations. Whereas CDC activity was measured with the DE format and ADE formats. When the additional DQ and R292C_V302C disulfide bond mutations were introduced in the DE format, the activity was reduced. When the additional DQ and R292C_V302C disulfide bond mutations are introduced in the ADE format, the CDC activity was lost (Table 18 and FIG. 12).

TABLE 19

CDC activity IC50 values for mAb1 + ADLE, DE or ADE −/+ DQ +/− L242C_K334C

| | mAb1 IgG1 | | | | | | | | | |
|---|---|---|---|---|---|---|---|---|---|---|
| | | ADLE | ADLE DQ_ L242C_ K334C | | | DE DQ_ L242C_ K334C | | | ADE DQ_ L242C_ K334C | |
| | iso ADLE | ADLE DQ | | iso DE | DE DQ | | iso ADE | ADE DQ | | WT control |
| | | | | | Batch | | | | | |
| Variable Region | VA2-20-034.2 | VA2-20-952-1 | VA2-20-954-1 | VA2-20-1117-1 | VA2-20-955-1* | VA2-20-957-1* | VA2-19-943-1** | VA2-21-266-1 | VA2-21-261-1 | VA2-20-950-1 |
| IC50 (nM) | NA | NA | NA | 2.65 | 5.62 | 5.25 | 2.46 | NA | NA | 2.44 |
| IC50 [95% CI] | NA | NA | NA | [2.34; 3.01] | [3.18; 9.95] | [3.12; 8.85] | [2.19; 2.76] | NA | NA | [2.14 2.79] |
| IC50 CV % | NA | NA | NA | 5.98 | 28.57 | 26.06 | 5.18 | NA | NA | 6.46 |
| Delta (Top-Bottom) % | NA | NA | NA | 89.47 | 29.77 | 25.36 | 82.94 | NA | NA | 76.02 |

No CDC activity was detected with the ADLE format and with the additional DQ and L242C_K334C disulfide bond mutations. Whereas CDC activity was measured with the DE format and ADE formats. When the additional DQ and L242C_K334C disulfide bond mutations were introduced in the DE format, the activity was reduced. When the additional DQ and L242C_K334C disulfide bond mutations were introduced in the ADE format, the CDC activity was lost (Table 19 and FIG. 13).

B—Assessment of the Capacity of the Variant to Induce Antibody-Dependent Cellular Cytotoxicity (ADCC) In Vitro.

Materials and Methods:

The ADCC capacity was evaluated using the LP1 cell line (MM, human multiple myeloma cells, Blood. 1989 March; 73(4):1020-7) expressing the antigen recognized by mAb1 as target cells and the natural killer cell line NK92 FCGR3A 158V (Conkwest) as effector cells.

Target cells were labelled with calcein-acetoxymethyl (2 mM; Invitrogen, Ref C3100MP) and resuspended at $2 \times 10^5$ in assay medium (RPMI 1640 without phenol red, 1% SVF, 0.77 mg/mL Probenecid, Invitrogen, P36400).

Target cells (T) were seeded at $2 \times 10^4$ cells per well in a 96 well plate, and pre-incubated 30 minutes at 37° C. with 5% of $CO_2$ and 50 µl of the antibody variants at serial dilution concentrations starting from 2.3 nM with a dilution factor of 3 for IgG1 wild-type, and starting from 1.25 nM with a dilution factor of 7 for ADLE, ADE, and DE variants.

As positive control of maximum calcein release level, target cells are incubated with 0.5% Triton.

Effector cells (E) are resuspended at $6 \times 10^5$ in assay medium, and 100 µL or $6 \times 10^4$ effector cells are added to the target cells per well (ratio T: E of 1:3). After an incubation of 3 hours at 37° C. at 5% $CO_2$, 100 µl of the culture supernatant are transferred to a black 96-well plate and calcein release was measured by fluorescence on a EnVision 2104 plate reader (PerkinElmer) at 492 nm excitation and 515 nm emission. Each point was performed in triplicate.

The % of cytotoxicity was calculated as follows:

% cytotoxicity=((RLU_sample−RLU medium)×100)/ (RLU_Positive control Triton−RLU medium).

RLU: Relative Light Units

Figure 14:
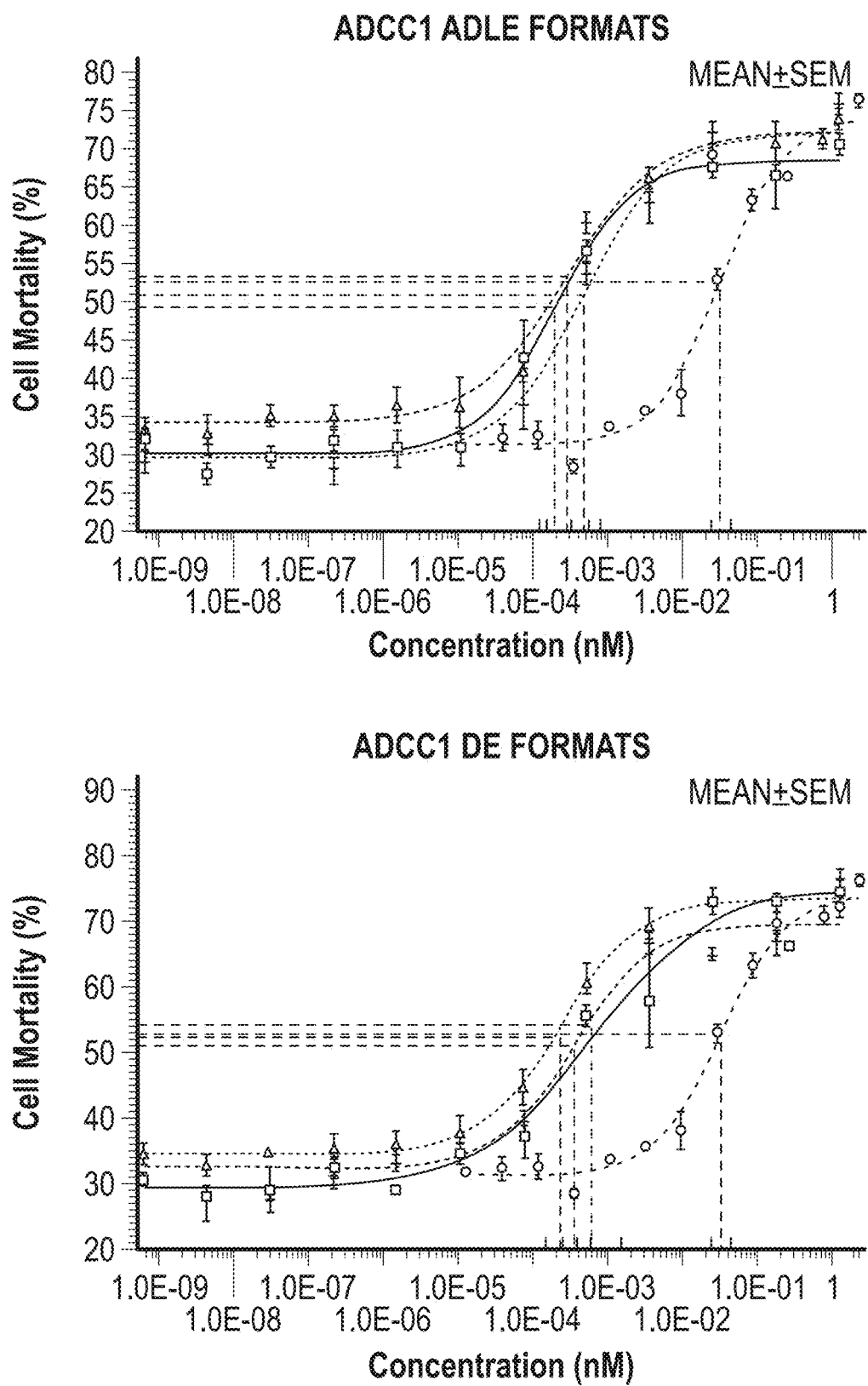
FIG. 14 depicts the ADCC activity of the ADLE variants, the DE variants, and ADE variants as compared to IgG1 wild-type for mAb1+/−ADLE, DE or ADE+/−L242C_K334C or R294C_V304C.
Figure 14:
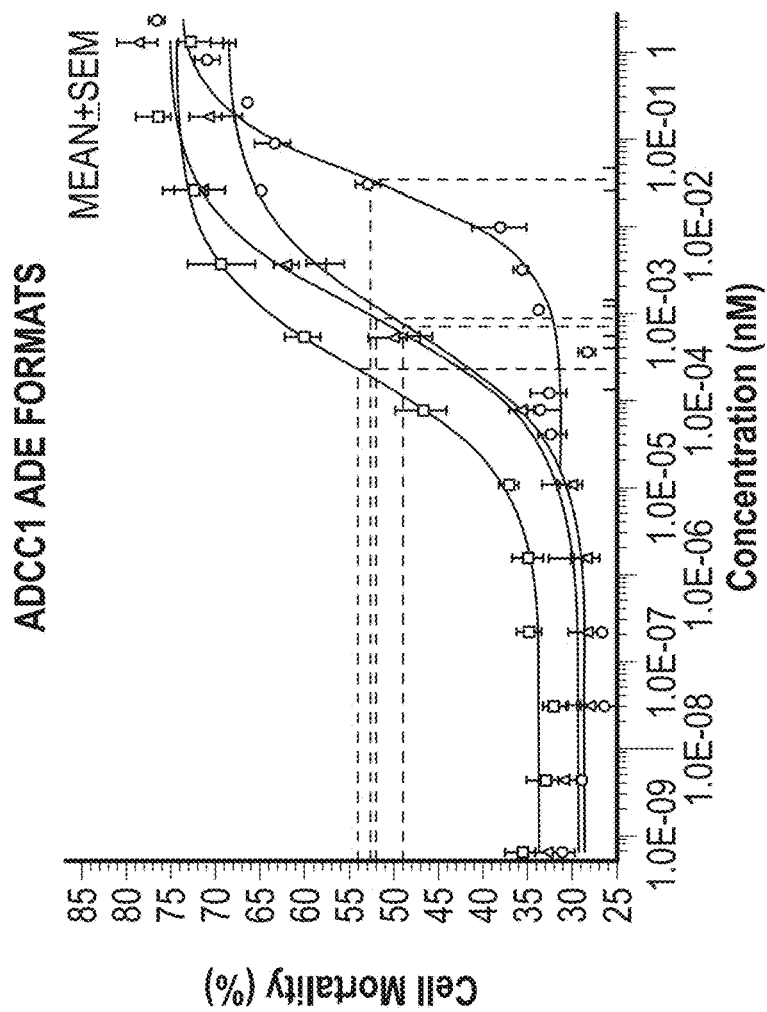
Figure 15:
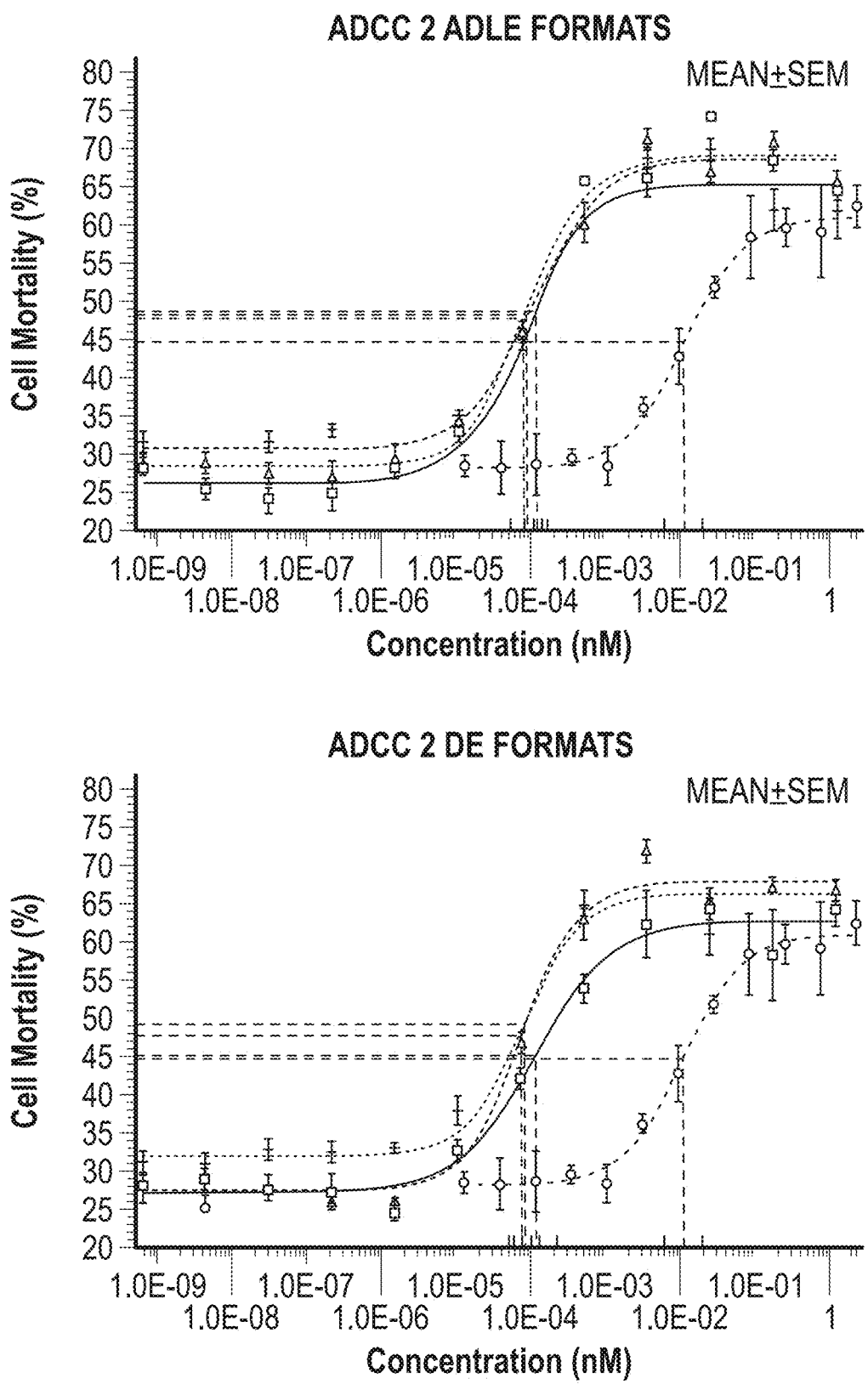
FIG. 15 depicts the ADCC activity of the ADLE variants, the DE variants, and ADE variants as compared to IgG1 wild-type for mAb1+/−ADLE, DE or ADE−/+DQ+/−R292C_V302C.
Figure 15:
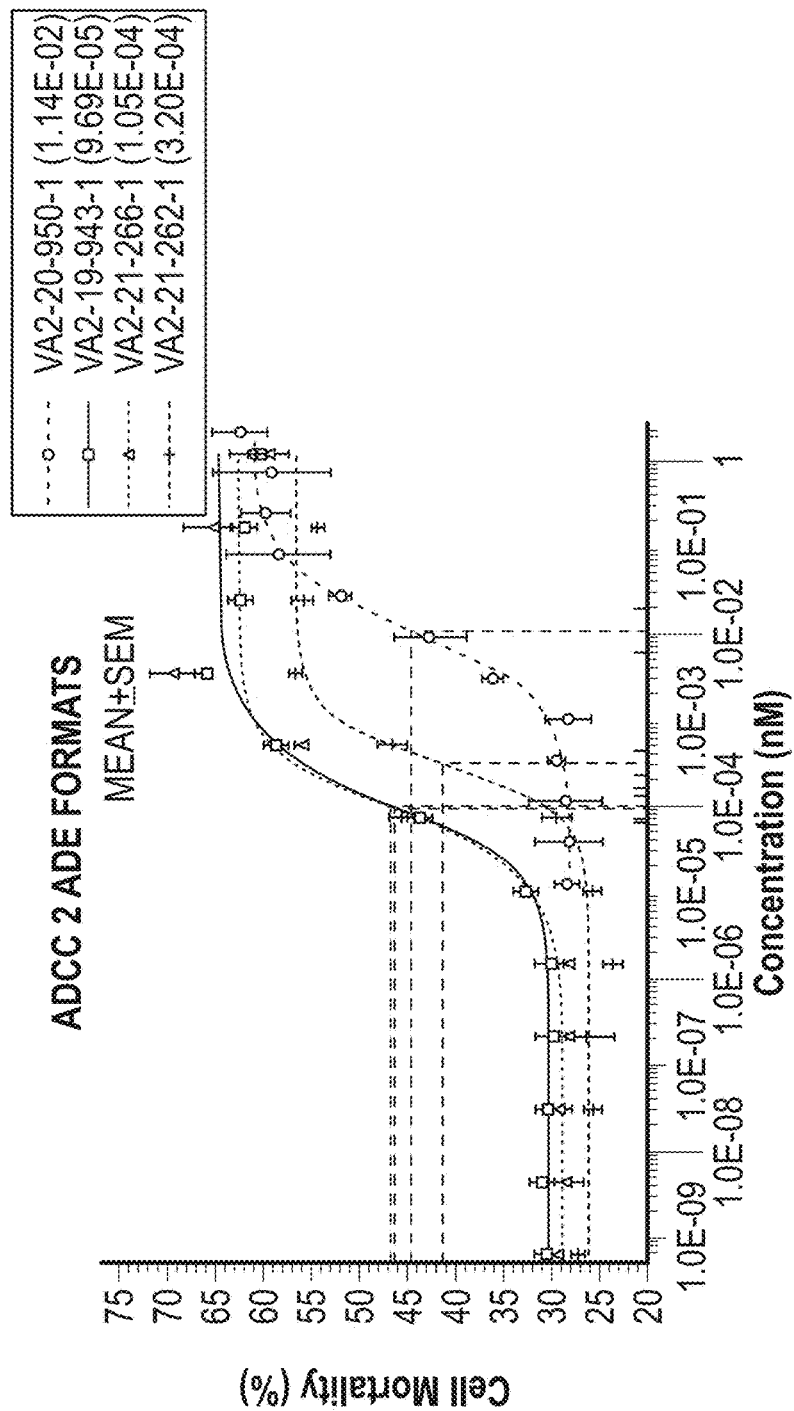
Figure 16:
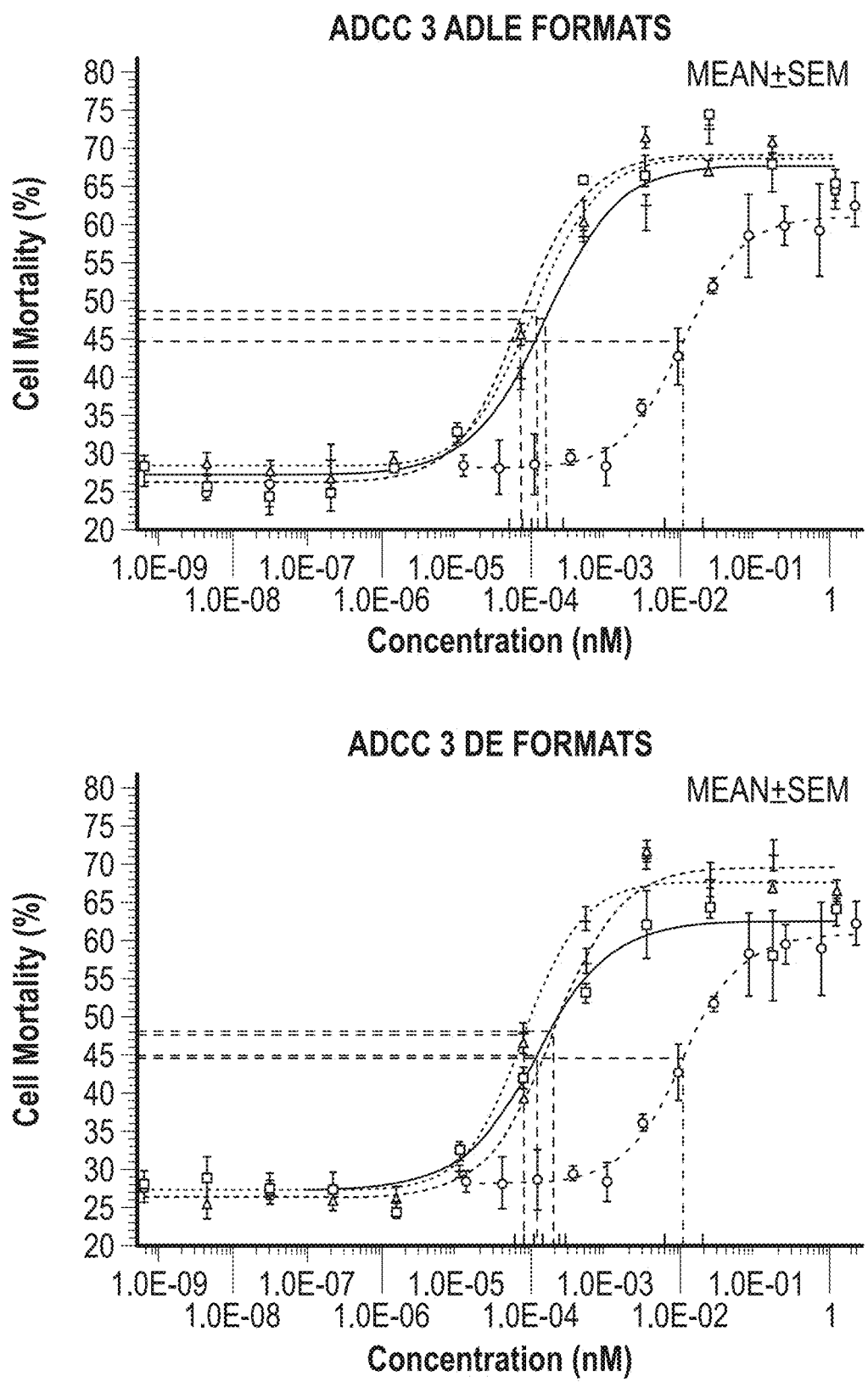
FIG. 16 depicts the ADCC activity of the ADLE variants, the DE variants, and ADE variants as compared to IgG1 wild-type for mAb1+/−ADLE, DE or ADE−/+DQ+/−DSB L242C_K334C.
Figure 16:
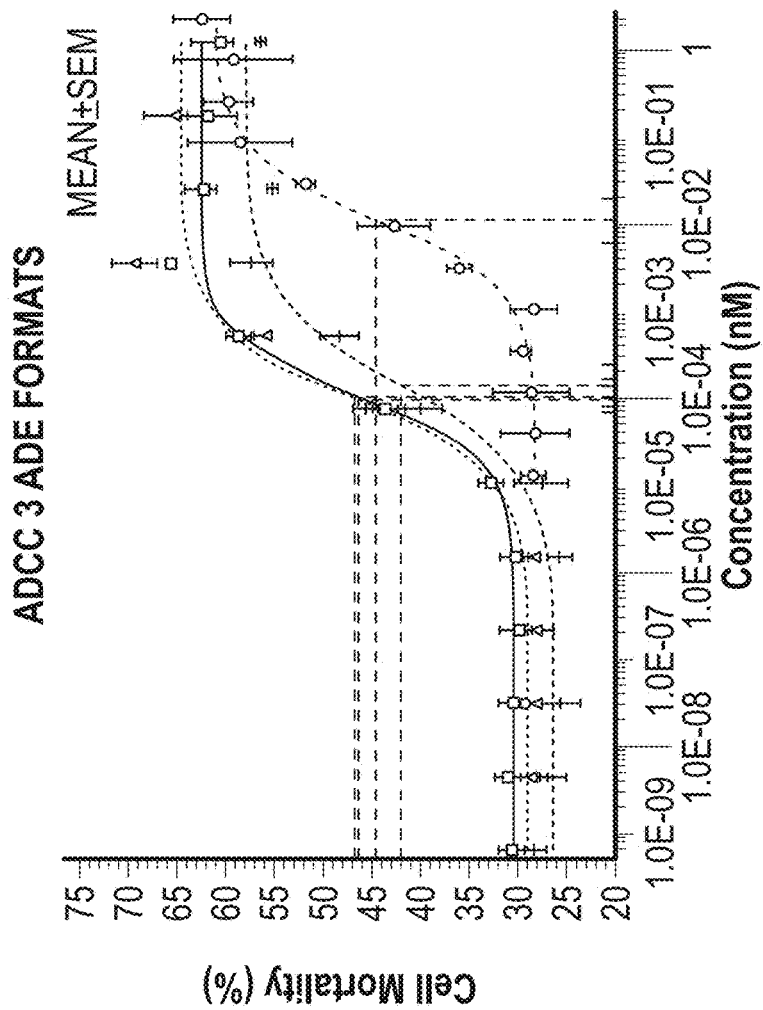

Data are a summary of at least three independent experiments. For each variant and each experiment, the IC50 value and the delta of the percentage of mortality were calculated. The reported results are the geometrical mean of IC50 values, CV and delta of mortality (Table 20), as well as a representative example of the ADCC activity of ADLE formats, ADE formats, and DE formats (FIG. 14-FIG. 16). Values were calculated using Biost@t-SPEED v2.4.

Results:

TABLE 20

ADCC Activity IC50 values for mAb1 +/− ADLE, DE or ADE +/− DSB (L242C_K33 C or R292C_V302C)

| | mAb1 IgG1 | | | | | | | | | |
|---|---|---|---|---|---|---|---|---|---|---|
| | iso ADLE | ADLE L242C_ K334C | ADLE R292C_ V302C | iso DE | DE R292C_ V302C | DE L242C_ K334C | iso ADE | ADE R292C_ V302C | ADE L242C_ K334C | WT control |
| | | | | | Batch | | | | | |
| Variable Region | VA2-20-034.2 | VA2-21-267-1 | VA2-21-268-1 | VA2-20-1117-1 | VA2-21-270-1 | VA2-21-269-1 | VA2-19-943-1 | VA2-21-260-1 | VA2-21-259-2 | VA2-20-950-1 |
| IC50 (nM) | 2.51E−04 | 4.08E−04 | 4.86E−04 | 4.51E−04 | 3.56E−04 | 4.01E−04 | 1.67E−04 | 5.41E−04 | 5.45E−04 | 1.76E−02 |
| IC50 [95% CI] | [1.65E−04; 3.84E−04] | [2.66E−04; 6.27E−04] | [2.92E−04; 8.07E−04] | [2.59E−04; 7.86E−04] | [2.41E−04; 5.27E−04] | [2.65E−04; 6.07E−04] | [1.09E−04; 2.56E−04] | [2.77E−04; 1.06E−03] | [3.51E−04; 8.48E−04] | [1.19E−02; 2.60E−002] |
| IC50 CV % | 20.91 | 19.91 | 24.01 | 25.10 | 19.01 | 19.61 | 20.58 | 30.43 | 21.72 | 19.16 |
| Delta (Top-Bottom) % | 48.18 | 43.52 | 47.05 | 53.71 | 45.51 | 48.73 | 44.70 | 45.26 | 47.63 | 51.23 |

NA: No fitting obtained.

The ADCC activity measured with the ADLE format was maintained in the same range when the DSB mutations either L242C_K334C or R292C_V302C were introduced in this format. Similarly, the ADCC activity measured with the DE and ADE format was maintained when these DSB mutations were introduced in these formats (Table 20 and FIG. 14).

TABLE 21

ADCC Activity IC50 values for mAb1 +/− ADLE, DE or ADE −/+ DQ +/− R292C_V302C

| | mAb1 IgG1 | | | | | | | | | |
|---|---|---|---|---|---|---|---|---|---|---|
| | iso ADLE | ADLE DQ | ADLE R292C_ V302C | iso DE | DE DQ | DE R292C_ V302C | iso ADE | ADE DQ | ADE R292C_ V302C | WT control |
| | | | | | Batch | | | | | |
| Variable Region | VA2-20-034.2 | VA2-20-952-1 | VA2-20-953-1 | VA2-20-1117-1 | VA2-20-955-1 | VA2-20-956-1 | VA2-19-943-1 | VA2-21-266-1 | VA2-21-262-1 | VA2-20-950-1 |
| IC50 (nM) | 8.11E−05 | 1.03E−04 | 1.71E−04 | 1.08E−04 | 9.01E−05 | 1.16E−04 | 1.13E−04 | 1.44E−04 | 2.97E−04 | 1.60E−02 |
| IC50 [95% CI] | [4.83E−05; 1.36E−04] | [6.58E−05; 1.63E−04] | [1.06E−04; 2.75E−04] | [6.54E−05; 1.79E−04] | [6.52E−05; 1.25E−04] | [7.21E−05; 1.86E−04] | [8.21E−05; 1.54E−04] | [9.12E−05; 2.28E−04] | [2.11E−04; 4.17E−04] | [9.58E−03; 2.67E−02] |
| IC50 CV % | 25.05 | 21.98 | 23.54 | 24.30 | 15.94 | 23.37 | 15.54 | 19.86 | 16.74 | 24.61 |
| Delta (Top-Bottom) % | 46.26 | 43.43 | 42.02 | 43.22 | 45.12 | 41.80 | 42.15 | 42.10 | 39.71 | 46.07 |

The ADCC activity measured with the ADLE format was maintained in the same range when the additional DQ mutation with or without the R292C_V302C were introduced in this format. Similarly, the ADCC activity measured with the DE & ADE formats were maintained when the additional DQ mutation with or without the R292C_V302C were introduced in these formats (Table 21 and FIG. 15).

TABLE 22

ADCC Activity IC50 values for mAb1 +/- ADLE, DE or ADE -/+ DQ +/- DSB L242C_K334C

| | mAb1 IgG1 | | | | | | | | | |
|---|---|---|---|---|---|---|---|---|---|---|
| | iso ADLE | ADLE DQ | ADLE L242C_K334C | iso DE | DE DQ | DE L242C_K334C | iso ADE | ADE DQ | ADE L242C_K334C | WT control |
| | | | | | Batch | | | | | |
| Variable Region | VA2-20-034.2 | VA2-20-952-1 | VA2-20-954-1 | VA2-20-1117-1 | VA2-20-955-1 | VA2-20-957-1 | VA2-19-943-1 | VA2-21-266-1 | VA2-21-261-1 | VA2-20-950-1 |
| IC50 (nM) | 8.11E−05 | 1.03E−04 | 1.54E−04 | 1.08E−04 | 9.01E−05 | 1.54E−04 | 1.13E−04 | 1.44E−04 | 1.62E−04 | 1.60E−02 |
| IC50 [95% CI] | [4.83-05; 1.36E−04] | [6.58E−05; 1.63E−04] | [1.00E−04; 2.37E−04] | [6.54E−05; 1.79E−04] | [6.52E−05; 1.25E−04] | [1.08E−04; 2.20E−04] | [8.21E−05; 1.54E−04] | [9.12E−05; 2.28E−04] | [1.07E−04; 2.46E−04] | [9.58E−03; 2.67E−02] |
| IC50 CV % | 25.05 | 21.98 | 20.60 | 24.30 | 15.94 | 17.45 | 15.54 | 19.86 | 19.53 | 24.61 |
| Delta (Top-Bottom) % | 46.26 | 43.43 | 46.62 | 43.22 | 45.12 | 44.93 | 42.15 | 42.10 | 39.20 | 46.07 |

The ADCC activity measured with the ADLE format was maintained in the same range when the additional DQ mutation with or without the L242C_K334C were introduced in this format. Similarly, the ADCC activity measured with the DE & ADE formats were maintained when the additional DQ mutation with or without the L242C_K334C were introduced in these formats (Table 22 and FIG. 16).

mAb3

Figure 17:
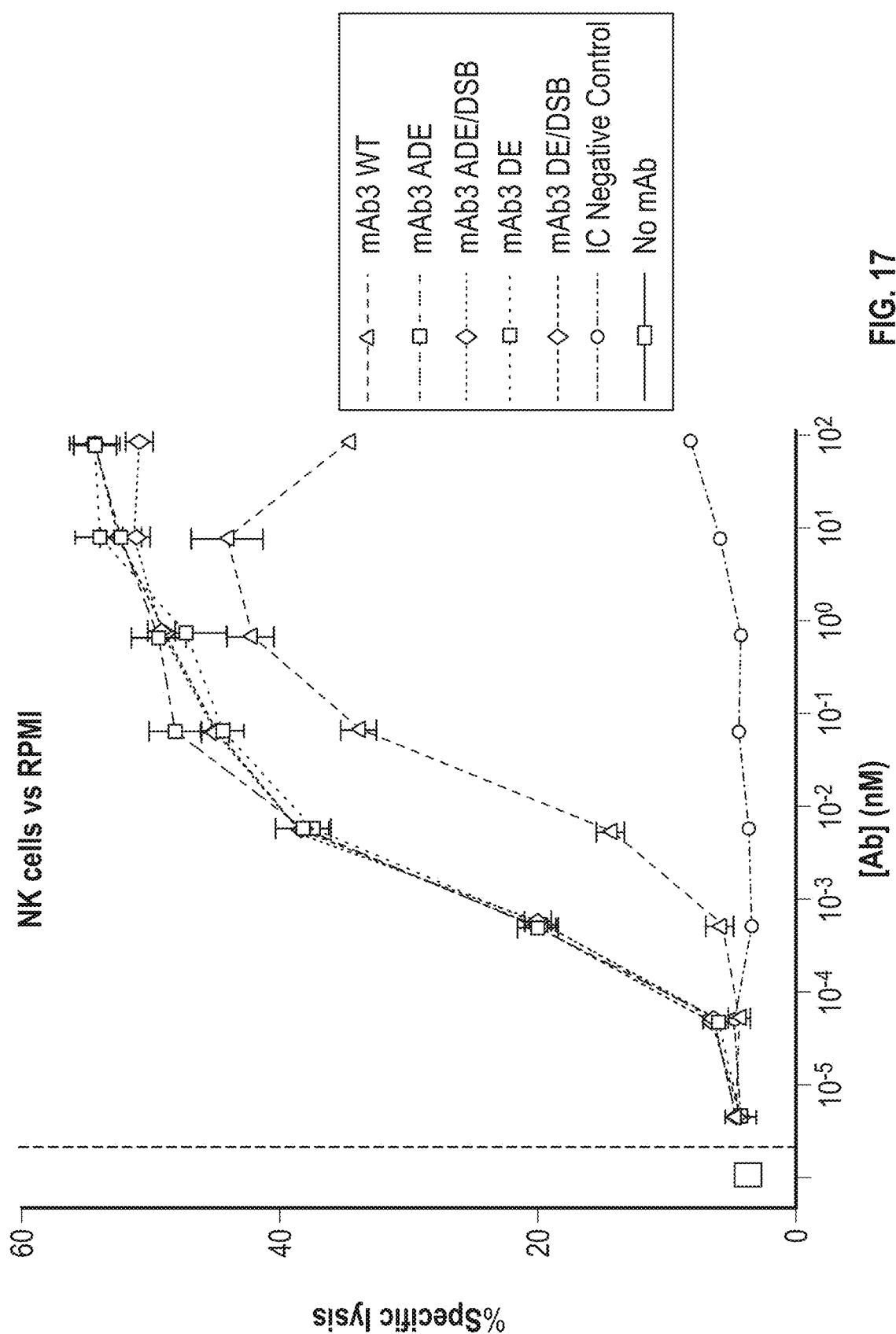
FIG. 17 depicts the cytotoxicity activity of the ADE variant and DE variant with or without the R292C-V3020 DSB substitution. Percent specific lysis is on the y axis with mAb3 concentration on the x axis in nM.

To demonstrate that the potency of antibodies with the DSB substitutions in combination with the ADE or DE substitutions was not lost, a cytotoxicity assay was performed with mAb3. As shown in FIG. 17, the inclusion of the DSB substitutions (R292C_V302C) did not impact the activity of mAb3, either in an ADE or DE background.

Example 7: PK Analysis of Disulfide Bond Stabilized Variants

This example describes the impact of DSB stabilized variant on PK profiles.

mAb1

Materials and Methods:

The mice experiments were performed in homozygous transgenic Tg32 (B6.Cg-Fcgrttm1Dcr Tg(FCGRT)32Dcr/DcrJ) mice derived from C57BL/6 mice and purchased from The Jackson Laboratory (Bar Harbor, Me.). FcRn-/- hFcRn (line 32) Tg mice carry a null mutation for the mouse gene and a transgene expressing the hFcRn α-chain transgene under the control of its natural human promoter.

All mice were treatment-naïve females between the ages of 8 and 12 weeks at study start. For dosing, the antibodies were prepared in DPBS 1× formulation buffer and administered as single intravenous doses of 1 mg/kg into the tail vein with a dose volume of 10 mL/kg. A total of 3 animals replicates were evaluated for each antibody utilizing a serial sampling approach (0.08, 4, 24, 72, 168, 240, 336, 504 and 672 hours) across the study duration of 28 days. Blood samples (around 20 μL) were collected by sampling time. Blood samples were centrifuged at 4° C. for 10 minutes at 1500 g and 6 μL of plasma samples were diluted in 60 μL of DPBS 1× before storage at −80° C. until analysis.

For mAb1 WT antibodies, the concentration of each antibody at each time point was determined by a bottom-up LC-MS/MS assay using the following generic method. After precipitation of a plasma aliquot, the plasma pellet was subjected to protein denaturation, reduction, alkylation, trypsin digestion, and solid-phase extraction prior to analysis of surrogate peptide. The surrogate peptide corresponding to a sequence of 17 amino acid residues belonging to the light chain of mAb1, was selected for each antibody for quantification, depending on its selectivity and response factor. Calibration standards were prepared by spiking the antibody into the plasma at 1, 2, 5, 10, 20, 50, 100, 200, and 400 μg/mL. Peptide separation was performed on a Waters Acquity UPLC system with a reverse phase XBridge BEH C18 column (2.1×150 mm, 3.5 μM, 300 Å, Waters) at a flow rate of 300 μL/min in a step-wise gradient of 0.1% formic acid in water and 0.1% formic acid in acetonitrile. For detection, a Sciex AP16500+ mass spectrometer was used in positive ion mode, with the source temperature at 700° C., the ionspray voltage at 5500 V, curtain and nebulizer gases at 40, and the collision gas at mid. Dwell time was 30 ms and the entrance potential was 10 V for each transition. Declustering potential was 90 V and collision energy was 26 V. The multiple reaction-monitoring transition (626.0 à 807.4 m/z) of the unique surrogate peptide of the antibodies was used for concentration determination relative to the standards and controls, using the peak area from the MQIII integration algorithm of the Analyst software.

For mAb1 variants (ADE, DE, ADLE, DE-DQ, and ADLE-DQ variants, the concentration of each antibody at each time point was determined by a generic immunoassay method using a Gyrolab platform (Gyros), it was a stepwise sandwich format. Samples (standards, quality controls and study samples) were diluted 100-fold in buffer and dispensed in a 96-well microtiter plate. The capture and detection reagents were dispensed in a second 96-well microtiter plate. Then the 96-well microtiter plates and the bioaffy CDs (CD200—containing 112 microstructured segments) were loaded on the Gyrolab platform. The following steps were triggered automatically by the Gyrolab platform: addition of biotinylated Donkey anti hu-IgG (capture) on the streptavidin bead columns within Gyrolab Bioaffy discs (CD200), then distribution of standards, quality controls and study samples and then addition of AlexaFluor-Goat anti hu-IgG (detection). The on-column fluorescence measurement (Aexc 633 nm, Aemm 650 nm) was performed in each microstructured segment using the photomultiplicator set at 1%. All analyses were performed in duplicate, and the range of quantification was 100 to 200 000 ng/mL.

PK parameters were determined from individual animal data, using non-compartmental analysis in Phoenix Win-Nonlin version 8.1 (Certara L.P.).

PK profiles from one animal administered with mAb1-ADLE_DQ_L242C_K334C that showed a sharp drop in concentration, typical of ADA interference, were excluded from PK calculations. One animal administered mAb1-DE_DQ_R292C_V302C was also excluded from PK analysis due to a dosing issue.

Results:

TABLE 23

Summary of PK parameters of the different antibodies tested in Tg32 mice (mean (CV %))

| mAb1 Compounds | C0 (μg/mL) | AUC (day*μg/mL) | CL (mL/day/kg) | Vss (mL/kg) | t1/2z (day) |
|---|---|---|---|---|---|
| ADLE-DQ | 22.9 | 42.6 | 23.5 | 97.3 | 3 |
| ADLE-DQ-L242C/K334C | 19.0 | 219 | 4.59 | 119 | 19 |
| ADLE-DQ-R292C/V302C | 18.1 | 244 | 4.49 | 136 | 23 |
| DE-DQ | 15.5 | 60.3 | 16.9 | 180 | 9 |
| DE-DQ-L242C/K334C | 13.5 | 150 | 6.89 | 152 | 16 |
| DE-DQ-R292C/V302C | 14.7 | 157 | 6.51 | 145 | 16 |
| WT | 19.7 | 127 | 7.88 | 163 | 16 |

Figure 18:
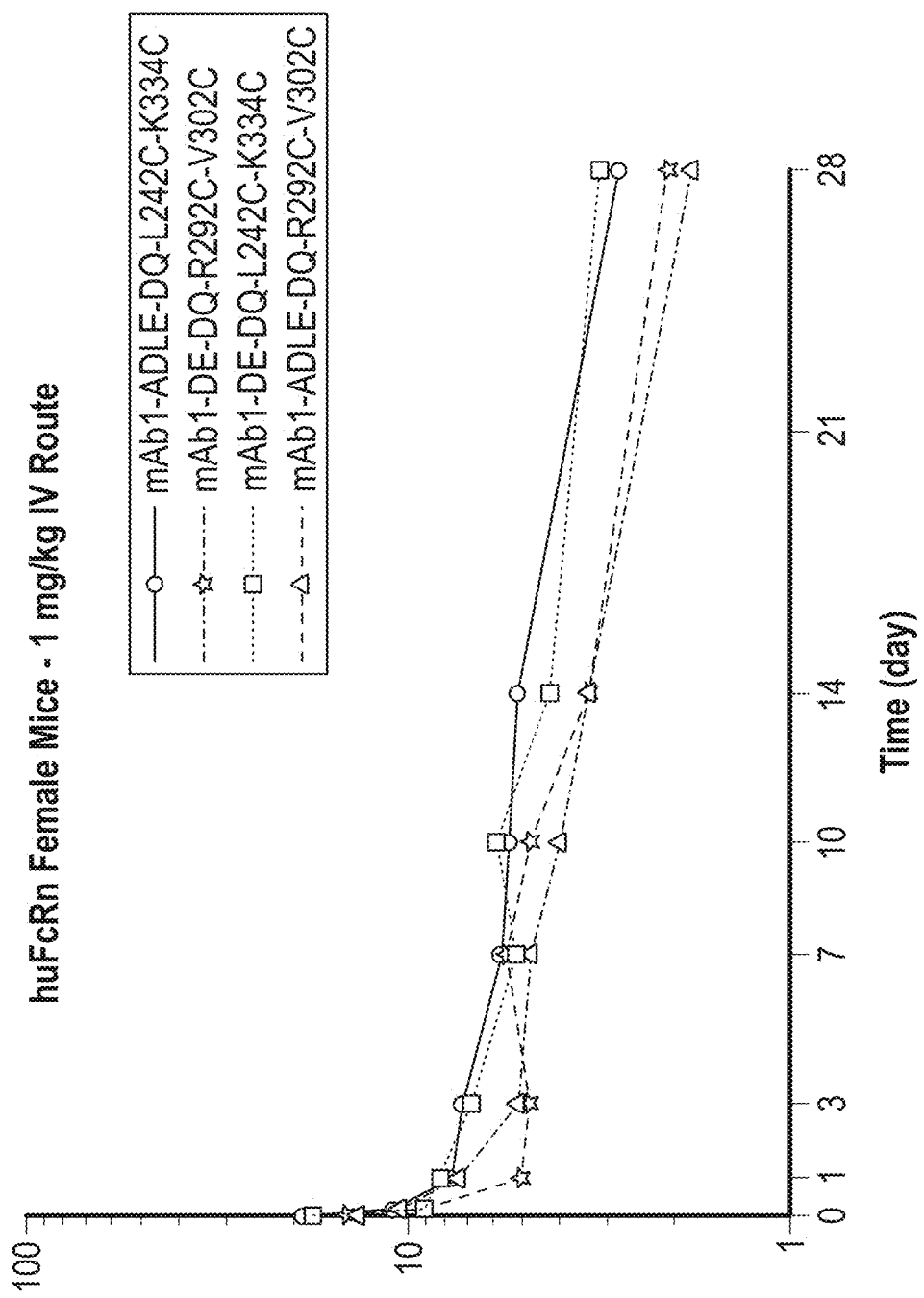
FIG. 18 depicts the mean PK profiles of mAb1 antibodies in Tg32 mice (log scale).
Figure 18:
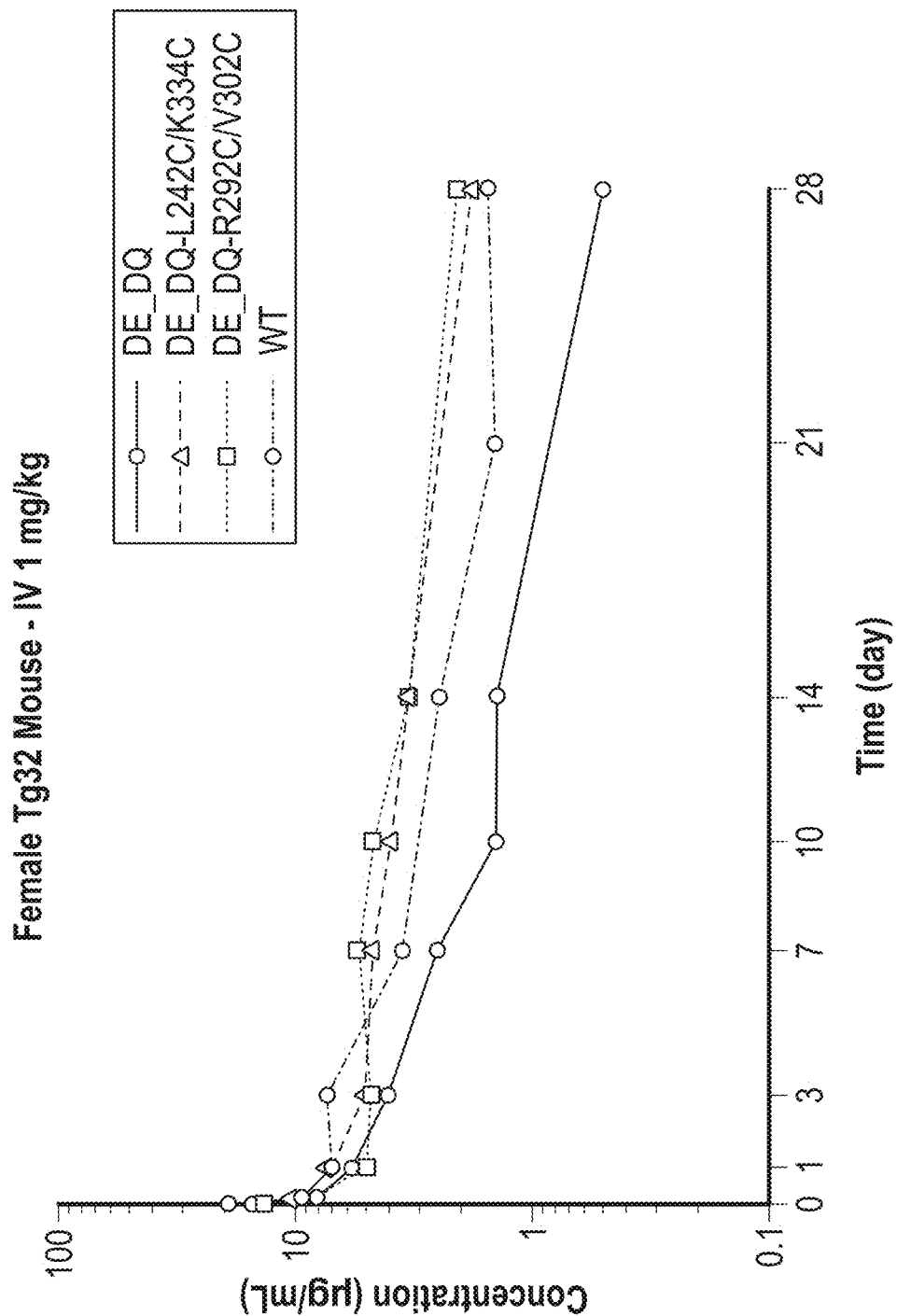
Figure 18:
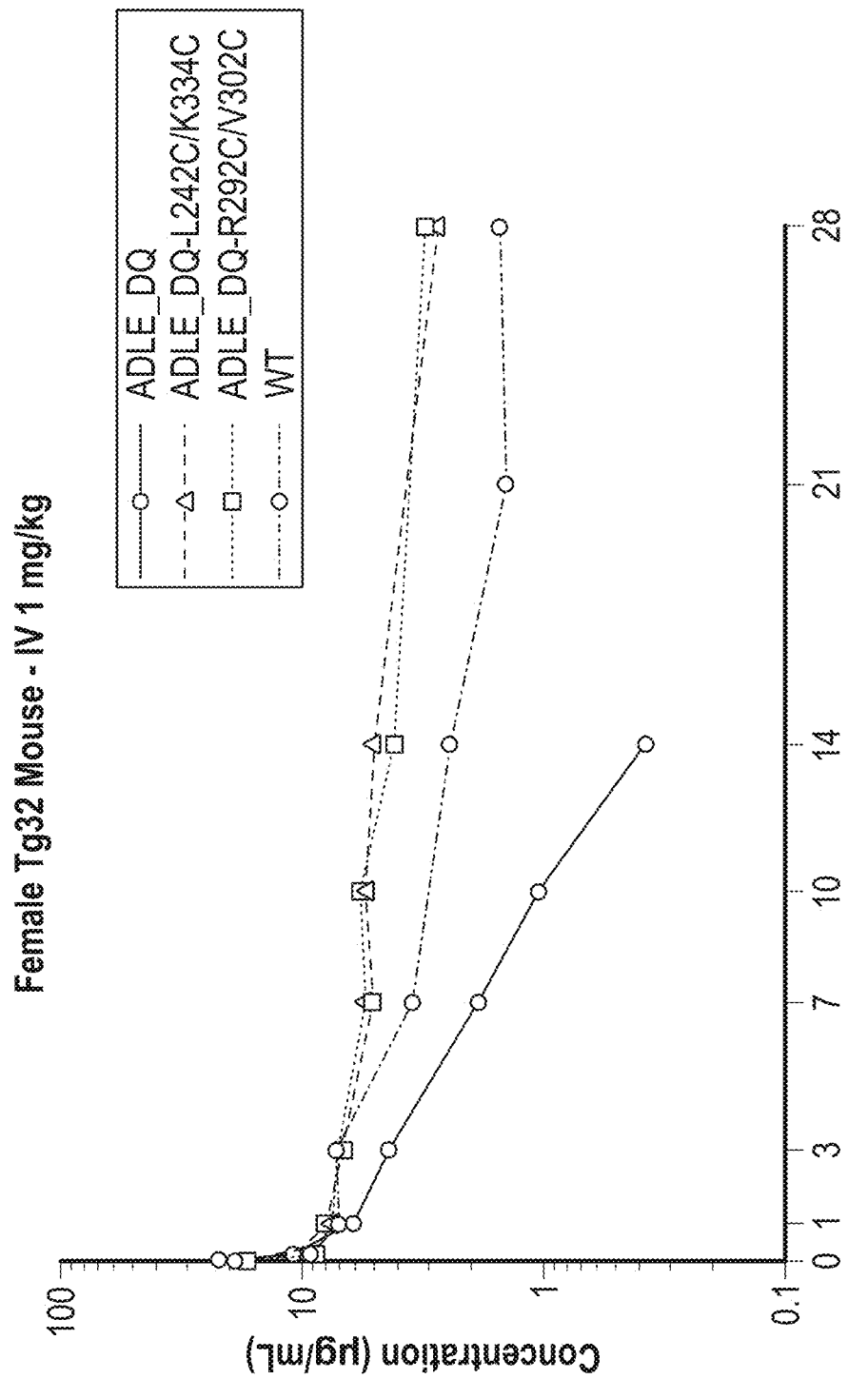

Similar PK profiles & parameters were observed with the two DSB positions (L242C-K334C and R292C-V3020) for DE_DQ and ADLE_DQ. DSB positions improved PK properties of DE_DQ & ADLE_DQ mutated constructs with elimination half-lives increased by 3 to 9-fold and clearance decreased by 4 to 10-fold. Elimination half-lives of ADLE_DQ_DSB were slightly longer than WT whereas t1/2z of DE_DQ_DSB were similar to the WT (FIG. 18).

Figure 19:
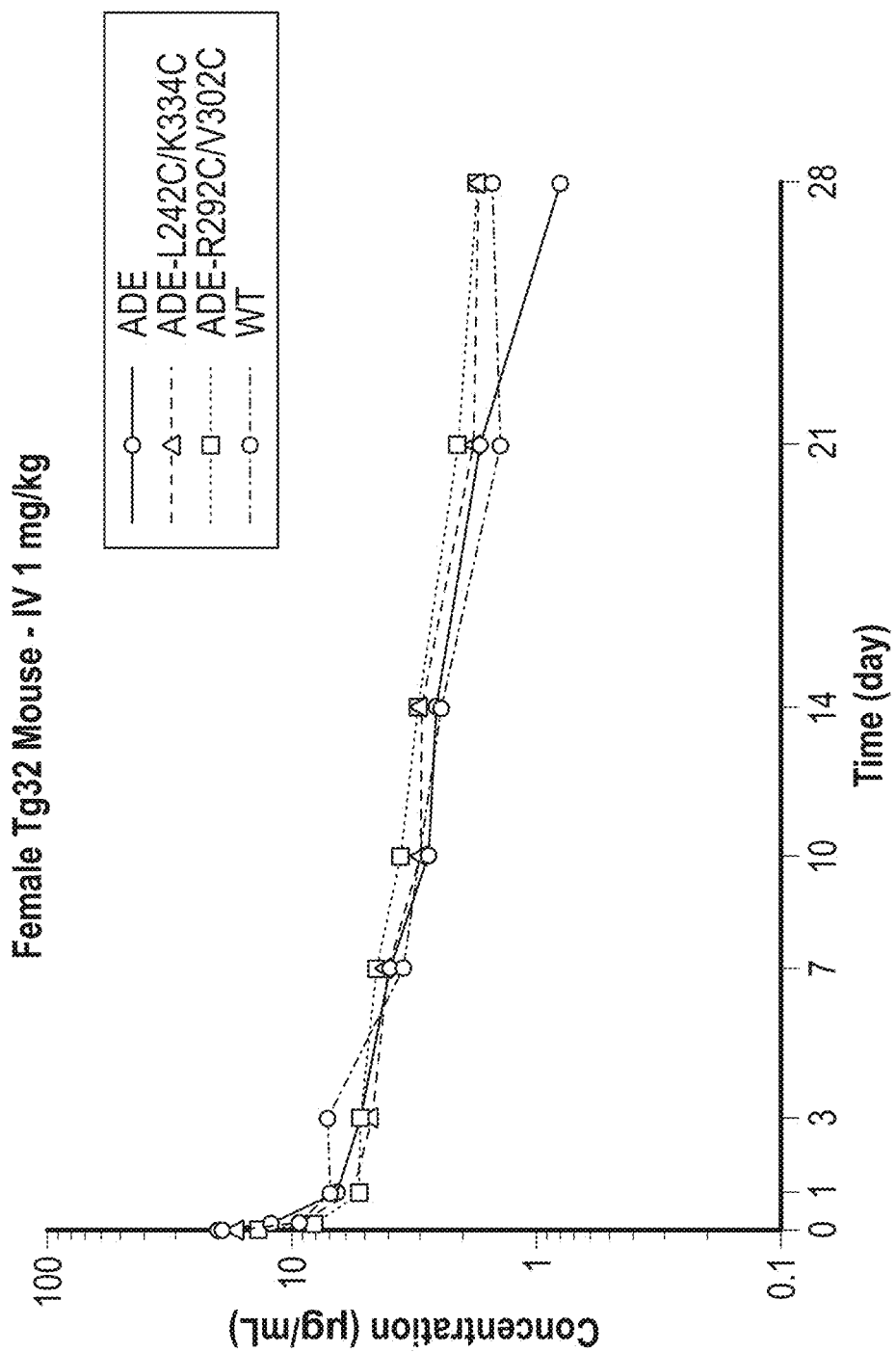
FIG. 19 depicts the mean PK profiles of additional mAb1 antibodies in Tg32 mice (log scale).
Figure 19:
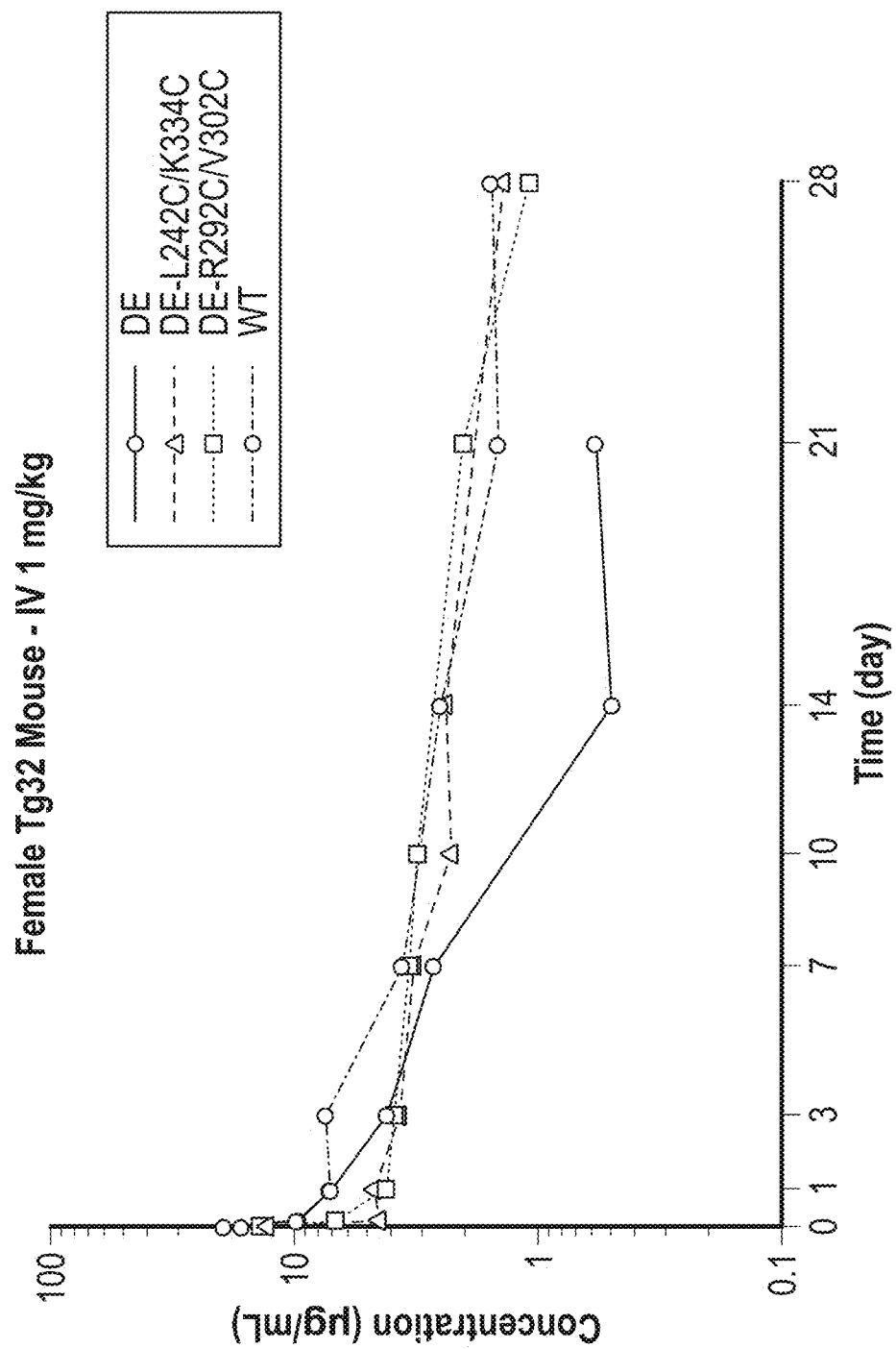
Figure 19:
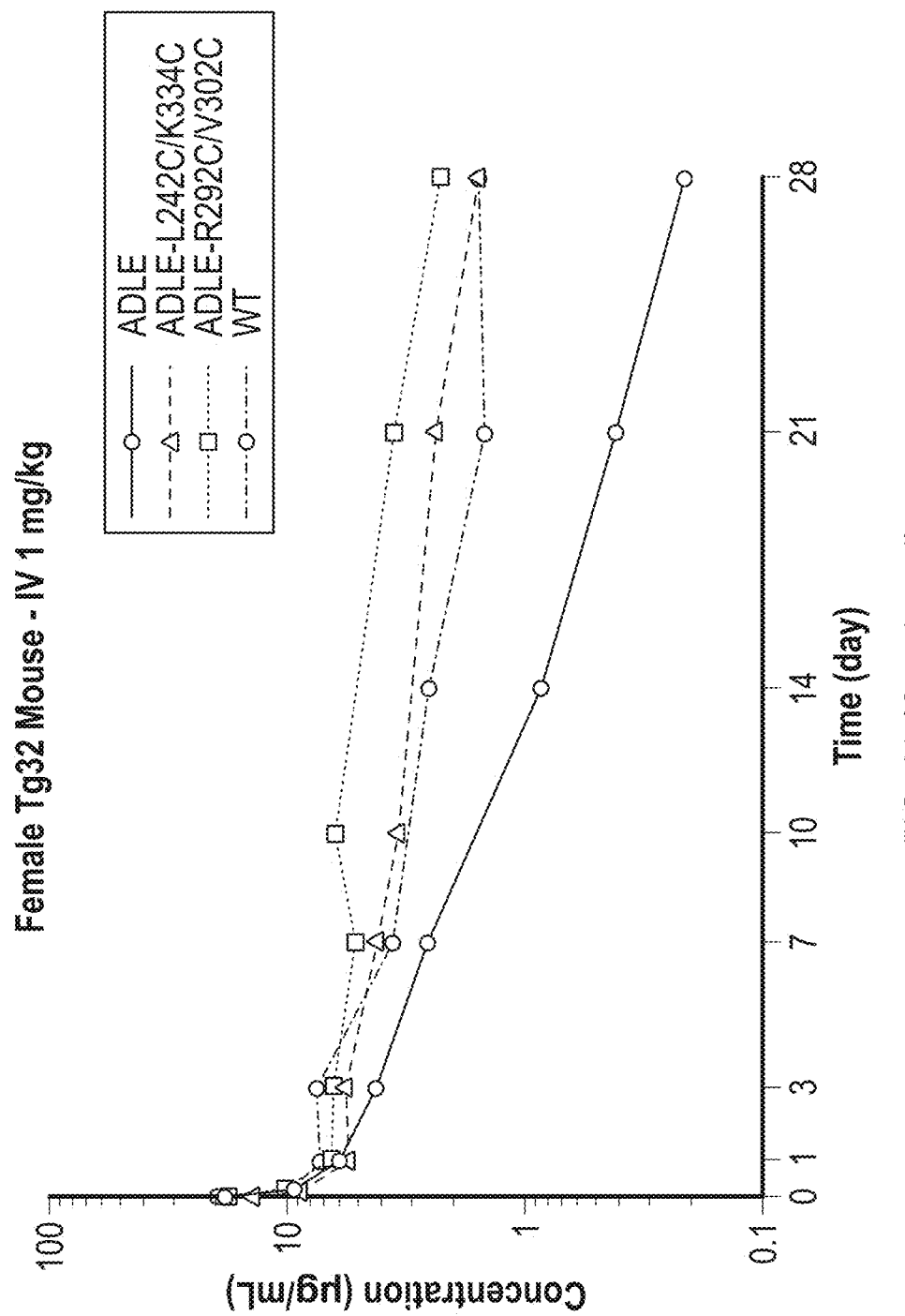

PK profiled were generated for mAb1 variants without the DQ substitution as well. The results are depicted in Table 24 and FIG. 19.

Similar PK profiles & parameters were observed with the two DSB positions (L242C-K334C and R292C-V3020), whatever the mutation (ADE, DE or ADLE). DSB positions clearly improved PK properties of DE & ADLE mutated constructs, with elimination half-lives increased by 2.5-3-fold and clearance decreased by 2.5-3-fold compared to DE & ADLE mutated constructs. The improvement of PK properties by adding DSB was less obvious for ADE mutated constructs. Nevertheless, PK parameters of all mutated constructs with DSB were like the WT construct, DSB stabilize mutated constructs in vivo.

TABLE 24

Summary of PK parameters of the different antibodies tested in Tg32 mice (mean (CV %))

| mAb1 Compound | C0 (μg/mL) | AUC (day*μg/mL) | CL (mL/day/kg) | Vss (mL/kg) | t1/2z (day) |
|---|---|---|---|---|---|
| ADE | 20.9 | 98.8 | 10.5 | 135 | 10 |
| ADE_L242C_K334C | 17.5 | 125 | 8.86 | 180 | 15 |
| ADE_R292C_V302C | 14.3 | 129 | 7.82 | 156 | 14 |
| ADLE | 17.9 | 51.9 | 19.3 | 137 | 6 |
| ADLE_L242C_K334C | 14.2 | 127 | 7.89 | 157 | 14 |
| ADLE_R292C_V302C | 18.1 | 186 | 5.39 | 114 | 15 |
| DE | 16.7 | 53.5 | 18.7 | 132 | 6 |
| DE_L242C_K334C | 13.2 | 108 | 9.29 | 243 | 19 |
| DE_R292C_V302C | 14.2 | 95.9 | 10.5 | 188 | 13 |
| WT | 19.7 | 127 | 7.88 | 163 | 16 | mAb3
Materials and Methods:

For mAb3 ADE and ADE-DSB (R292C/V302C) variants, the concentration at each time point was determined by a bottom-up LC-MS/MS assay using the following generic method: After precipitation of a plasma aliquot, the plasma pellet was subjected to protein denaturation, reduction, alkylation, trypsin digestion, and solid-phase extraction prior to analysis of surrogate peptide. The surrogate peptide VYACEVTHQGLSSPVTK (SEQ ID NO: 20), belonging to Fab regions (light chain), was selected for each antibody for quantification, depending on its selectivity and response factor. Calibration standards were prepared by spiking the antibody into the plasma at 1, 2.8, 7, 14, 40, 80 and 100 μg/mL. Peptide separation was performed on a Shimadzu UHPLC system with a reverse phase XBridge BEH C18 column (2.1×150 mm, 3.5 μM, 300 Å, Waters) at a flow rate of 600 μL/min in a stepwise gradient of 0.1% formic acid in water and 0.1% formic acid in acetonitrile. For detection, a Sciex AP16600 TripleTOF mass spectrometer was used in positive product ion mode, with the source temperature at 500° C., the ionspray voltage at 5500 V, curtain gas at 35 and nebulizer gases at 50. Dwell time was 15 ms for each experiment. Declustering Potential was 90 V and Collision Energy was 26 V. The 807.4098 m/z fragment of the 626.0 m/z parent ion of the unique surrogate peptide of the antibodies was used for concentration determination relative to the standards and controls, using the peak area from the MQ4 integration algorithm of the MultiQuant software.

For mAb3 WT antibodies, the concentration at each time point was determined by a generic immunoassay method using a Gyrolab platform (Gyros), it was a stepwise sandwich format. Samples (standards, quality controls and study samples) are diluted 100-fold in buffer and dispensed in a 96-well microtiter plate. The capture and detection reagents were dispensed in a second 96-well microtiter plate. Then the 96-well microtiter plates and the bioaffy CDs (CD200—containing 112 microstructured segments) were loaded on the Gyrolab platform. The following steps were triggered automatically by the Gyrolab platform: addition of biotinylated Donkey anti hu-IgG (capture) on the streptavidin bead columns within Gyrolab Bioaffy discs (CD200), then distribution of standards, quality controls and study samples and then addition of AlexaFluor-Goat anti hu-IgG (detection). The on-column fluorescence measurement (λexc 633 nm, λemm 650 nm) was performed in each microstructured segment using the photomultiplicator set at 1%. All analyses were performed in duplicate, and the range of quantification was 100 to 200 000 ng/mL.

Figure 20:
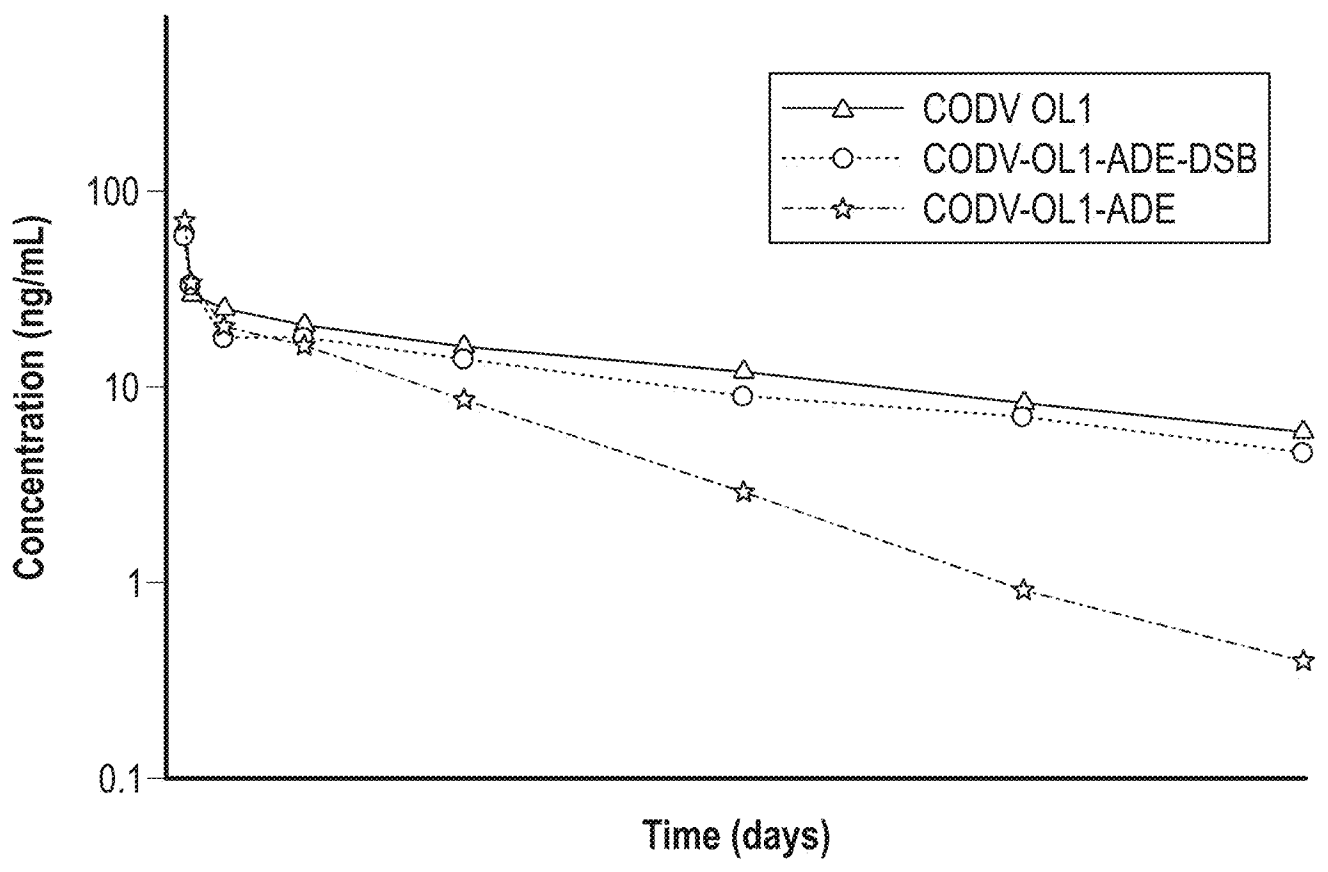

Similar PK studies were performed with mAb3. As shown in Table 25 and FIG. 20, ADE mutations on mAb3 led to a higher CL and a shorter elimination half-life compared to mAb3 WT. Addition of DSB (R292C/V302C) on the mAb3-ADE construct clearly improved PK properties of the compound. mAb3 WT and mAb3-ADE-DSB constructs exhibited similar clearance and elimination half-life.

TABLE 25

Summary of PK parameters of the different mAb3 antibodies tested in Tg32 mice (mean (CV %))

| Antibody | C0 (ug/mL) | AUC (day*ug/mL) | CL (mL/day/kg) | Vss (mL/kg) | t1/2z (day) |
|---|---|---|---|---|---|

```
                    275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 2
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 3
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Asp Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Gln Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

```
<210> SEQ ID NO 4
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Cys Phe Pro Pro
        115                 120                 125

Lys Pro Lys Asp Thr Leu Met Ile Ser Arg Asp Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Gln Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Cys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 5
<211> LENGTH: 329
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 5

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Asp Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Cys Glu
                165                 170                 175

Glu Gln Tyr Asn Ser Thr Tyr Arg Cys Val Ser Val Leu Gln Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 6
<211> LENGTH: 329
<212> TYPE: PRT
<213> ORGANISM: Artificial Sequence
<220> FEATURE:
<223> OTHER INFORMATION: Description of Artificial Sequence: Synthetic polypeptide

```
<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Cys Glu
                165                 170                 175

Glu Gln Tyr Asn Ser Thr Tyr Arg Cys Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 7
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Cys Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Cys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 8
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Ala Gly Pro Asp Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Glu Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 9
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Ala Gly Pro Asp Val Phe Leu Phe Pro Pro
                115                 120                 125

Lys Pro Lys Asp Thr Leu Met Ile Ser Arg Asp Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                    165                 170                 175

Glu Gln Tyr Asn Ser Thr Tyr Arg Val Val Ser Val Leu Gln Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp
    290                 295                 300

<210> SEQ ID NO 10
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Ala Gly Pro Asp Val Phe Leu Phe Pro Pro
            115                 120                 125
```

```
Lys Pro Lys Asp Thr Leu Met Ile Ser Arg Asp Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Cys Glu
                165                 170                 175

Glu Gln Tyr Asn Ser Thr Tyr Arg Cys Val Ser Val Leu Gln Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 11
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Ala Gly Pro Asp Val Phe Cys Phe Pro Pro
            115                 120                 125

Lys Pro Lys Asp Thr Leu Met Ile Ser Arg Asp Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Gln Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Glu Glu Cys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp
            290                 295                 300

<210> SEQ ID NO 12
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Ala Gly Pro Asp Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Cys Glu
            165                 170                 175

Glu Gln Tyr Asn Ser Thr Tyr Arg Cys Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Glu Glu Lys Thr Ile Ser Lys Ala Lys Gly
```

```
                210                 215                 220
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 13
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Ala Gly Pro Asp Val Phe Cys Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Glu Glu Cys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 14
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Ala Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

```
<210> SEQ ID NO 15
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Ala Gly Pro Asp Val Phe Leu Phe Pro Pro
        115                 120                 125

Lys Pro Lys Asp Thr Leu Met Ile Ser Arg Asp Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Gln Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn

```
                290                 295                 300
Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 16
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Ala Gly Pro Asp Val Phe Cys Phe Pro Pro
        115                 120                 125

Lys Pro Lys Asp Thr Leu Met Ile Ser Arg Asp Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Gln Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Cys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly
                325

<210> SEQ ID NO 17
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Ala Gly Pro Asp Val Phe Leu Phe Pro Pro
        115                 120                 125

Lys Pro Lys Asp Thr Leu Met Ile Ser Arg Asp Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Cys Glu
                165                 170                 175

Glu Gln Tyr Asn Ser Thr Tyr Arg Cys Val Ser Val Leu Gln Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 18
```

<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Ala Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Cys Glu
                165                 170                 175

Glu Gln Tyr Asn Ser Thr Tyr Arg Cys Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 19
<211> LENGTH: 329
<212> TYPE: PRT
<213> ORGANISM: Artificial Sequence
<220> FEATURE:
<223> OTHER INFORMATION: Description of Artificial Sequence: Synthetic

```
                    polypeptide

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Ala Gly Pro Asp Val Phe Cys Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Cys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 20
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 20

Val Tyr Ala Cys Glu Val Thr His Gln Gly Leu Ser Ser Pro Val Thr
1               5                   10                  15

Lys
```

The invention claimed is:

1. An isolated effector-competent polypeptide, comprising:
  a glycosylated Fc domain comprising a first heavy chain and a second heavy chain, wherein at least one heavy chain comprises an engineered intrachain disulfide bond mediated by a pair of cysteines (C) that substitute for:
  an arginine (R) at amino acid position 292 and a valine (V) at amino acid position 302;
  wherein the amino acid positions are according to EU numbering;
  wherein the glycosylated Fc domain is capable of interacting with an antibody effector molecule; and
  wherein the effector-competent polypeptide has enhanced thermal stability compared to an effector-competent polypeptide having a glycosylated Fc domain capable of interacting with an antibody effector molecule that does not comprise the engineered intrachain disulfide bond.

2. The isolated effector-competent polypeptide of claim 1, wherein
  the glycosylated Fc domain comprises a native glycan at amino acid position 297, according to EU numbering.

3. The isolated effector-competent polypeptide of claim 1, wherein the first heavy chain and/or the second heavy chain each comprise the pair of cysteines.

4. The isolated effector-competent polypeptide of claim 1, wherein
  the Fc domain is an IgG1Fc domain.

5. The isolated effector-competent polypeptide of claim 1, wherein
  the Fc domain further comprises a substitution at amino acid position 332, according to EU numbering.

6. The isolated effector-competent polypeptide of claim 1, wherein
  the Fc domain further comprises an aspartic acid (D) at amino acid position 239, and a glutamic acid (E) at amino acid position 332, according to EU numbering.

7. The isolated effector-competent polypeptide of claim 1, wherein the Fc domain further comprises a substitution at amino acid position 256 and/or 307, according to EU numbering.

8. An isolated effector-competent polypeptide, comprising:
  a glycosylated Fc domain comprising a first heavy chain and a second heavy chain, wherein at least one heavy chain comprises an engineered intrachain disulfide bond mediated by a pair of cysteines (C) that substitute for
  an arginine (R) at amino acid position 292 and a valine (V) at amino acid position 302;
  wherein the glycosylated Fc domain is capable of interacting with an antibody effector molecule and comprises a glutamic acid (E) at amino acid position 332;
  wherein the effector-competent polypeptide has enhanced thermal stability compared to an effector-competent polypeptide having a glycosylated Fc domain capable of interacting with an antibody effector molecule and comprising a glutamic acid (E) at amino acid position 332, that does not comprise the engineered intrachain disulfide bond; and
  wherein the amino acid positions are according to EU numbering.

9. The isolated effector-competent polypeptide of claim 8, further comprising, according to EU numbering.

10. The isolated effector-competent polypeptide of claim 9, wherein the one or more substitutions are on the same heavy chain as the engineered disulfide bond or the one or more substitutions are on a different heavy chain as the engineered disulfide bond.

11. The isolated effector-competent polypeptide of claim 8, wherein
  the isolated effector-competent polypeptide further comprises a binding domain.

12. An isolated nucleic acid molecule comprising a nucleic acid encoding the isolated effector-competent polypeptide of claim 1.

13. A vector comprising the isolated nucleic acid molecule of claim 12.

14. A host cell comprising the vector of claim 13.

15. A pharmaceutical composition comprising the isolated effector-competent polypeptide of claim 1.

16. A method of increasing yield of an isolated effector-competent polypeptide, comprising: expressing a glycosylated Fc domain comprising a first heavy chain and a second heavy chain, wherein at least one heavy chain comprises an engineered intrachain disulfide bond mediated by a pair of cysteines (C) that substitute for:
  an arginine (R) at amino acid position 292 and a valine (V) at amino acid position 302;
  wherein the amino acid positions are according to EU numbering;
  wherein the glycosylated Fc domain is capable of interacting with an antibody effector molecule; and
  wherein the effector-competent polypeptide has enhanced thermal stability compared to an effector-competent polypeptide having a glycosylated Fc domain capable of interacting with an antibody effector molecule that does not comprise the engineered intrachain disulfide bond; and
  purifying the effector-competent polypeptide, wherein yield of said polypeptide is increased compared to a polypeptide comprising a wild-type glycosylated Fc domain.

17. The method of claim 16, wherein the isolated effector-competent polypeptide is capable of depleting a target cell by antibody-dependent cellular cytotoxicity (ADCC) and/or complement-dependent cytotoxicity (CDC).

18. The isolated effector-competent polypeptide of claim 1, wherein the glycosylated Fc domain comprises an engineered or non-native glycan.

19. The isolated effector-competent polypeptide of claim 18, wherein the engineered or non-native glycan is a modified glycan that can be conjugated to a therapeutic molecule.

20. The isolated effector-competent polypeptide of claim 1, wherein the isolated effector-competent polypeptide is N-glycosylated.

21. The isolated effector-competent polypeptide of claim 1, wherein the antibody effector molecule is a FcRn.

22. The isolated effector-competent polypeptide of claim 21, wherein the isolated effector-competent polypeptide has enhanced binding affinity to the FcRn compared to a wild-type Fc domain.

23. The isolated effector-competent polypeptide of claim 1, wherein the antibody effector molecule is a FcγRIIIa.

24. The isolated effector-competent polypeptide of claim 23, wherein the isolated effector-competent polypeptide has enhanced binding affinity to the FcγRIIIa compared to a polypeptide comprising a wild-type Fc domain.

25. The isolated effector-competent polypeptide of claim 1, wherein the isolated effector-competent polypeptide has altered serum half-life compared to a wild-type Fc domain.

26. The isolated effector-competent polypeptide of claim 25, wherein the isolated effector-competent polypeptide has enhanced serum half-life compared to a wild-type Fc domain.

27. The isolated effector-competent polypeptide of claim 1, wherein the Fc domain is a human IgG1 Fc domain.

28. The isolated effector-competent polypeptide of claim 5, wherein the substitution at amino acid position 332 is a glutamic acid (E).

29. The isolated effector-competent polypeptide of claim 5, wherein the Fc domain further comprises one or more substitutions at amino acid positions 236, 239, or 330, according to EU numbering.

30. The isolated effector-competent polypeptide of claim 29, wherein the substitution at amino acid position 236 is an alanine (A), the substitution at amino acid position 239 is an aspartic acid (D), and/or the substitution at amino acid position 330 is a leucine (L).

31. The isolated effector-competent polypeptide of claim 1, wherein the Fc domain further comprises an alanine (A) at amino acid position 236, an aspartic acid (D) at amino acid position 239, and a glutamic acid (E) at amino acid position 332, according to EU numbering.

32. The isolated effector-competent polypeptide of claim 1, wherein the Fc domain further comprises an alanine (A) at amino acid position 236, an aspartic acid (D) at amino acid position 239, a leucine (L) at amino acid position 330, and a glutamic acid (E) at amino acid position 332, according to EU numbering.

33. The isolated effector-competent polypeptide of claim 7, wherein the substitution at amino acid position 256 is an aspartic acid (D) and/or the substitution at amino acid position 307 is a glutamine (Q).

34. The isolated effector-competent polypeptide of claim 8, further comprising an alanine (A) at amino acid position 236, according to EU numbering.

35. The isolated effector-competent polypeptide of claim 8, further comprising a leucine (L) at amino acid position 330, according to EU numbering.

36. The isolated effector-competent polypeptide of claim 8, further comprising an aspartic acid (D) at amino acid position 256, according to EU numbering.

37. The isolated effector-competent polypeptide of claim 8, further comprising a glutamine (Q) at amino acid position 307, according to EU numbering.

38. The isolated effector-competent polypeptide of claim 11, wherein the binding domain comprises one or more antigen binding domains.

39. The isolated effector-competent polypeptide of claim 38, wherein the one or more antigen binding domains specifically bind to a tumor antigen and/or an antigen on an immune cell.

40. The isolated effector-competent polypeptide of claim 8, wherein the polypeptide is an antibody.

41. The isolated effector-competent polypeptide of claim 40, wherein the antibody is a monoclonal antibody, a chimeric, humanized, or human antibody, a full-length antibody, a single-domain antibody, and/or a multi-specific antibody.

42. The vector of claim 13, wherein the vector is an expression vector.

43. The host cell of claim 14, wherein the host cell is of eukaryotic or prokaryotic origin.

* * * * *